US012419905B2

(12) United States Patent
Strittmatter et al.

(10) Patent No.: US 12,419,905 B2
(45) Date of Patent: Sep. 23, 2025

(54) METHODS AND COMPOSITIONS FOR THE TREATMENT OF AMYLOID-RELATED DISORDERS

(71) Applicant: YALE UNIVERSITY, New Haven, CT (US)

(72) Inventors: Stephen M. Strittmatter, Durham, CT (US); Erik Christian Gunther, Branford, CT (US); Levi M. Smith, Branford, CT (US)

(73) Assignee: YALE UNIVERSITY, New Haven, CT (US)

( * ) Notice: Subject to any disclaimer, the term of this patent is extended or adjusted under 35 U.S.C. 154(b) by 1079 days.

(21) Appl. No.: 17/258,357

(22) PCT Filed: Jul. 3, 2019

(86) PCT No.: PCT/US2019/040565
§ 371 (c)(1),
(2) Date: Jan. 6, 2021

(87) PCT Pub. No.: WO2020/010236
PCT Pub. Date: Jan. 9, 2020

(65) Prior Publication Data
US 2021/0268016 A1 Sep. 2, 2021

Related U.S. Application Data

(60) Provisional application No. 62/694,710, filed on Jul. 6, 2018.

(51) Int. Cl.
*A61K 31/795* (2006.01)
*A61K 31/155* (2006.01)
*A61K 31/195* (2006.01)
*A61K 31/198* (2006.01)
*A61K 31/64* (2006.01)
*A61K 31/78* (2006.01)
*A61K 31/785* (2006.01)
*A61K 31/787* (2006.01)
*A61K 31/80* (2006.01)
*A61K 36/16* (2006.01)
*A61K 38/26* (2006.01)
*A61K 38/28* (2006.01)
*A61K 45/06* (2006.01)
*A61P 25/28* (2006.01)

(52) U.S. Cl.
CPC .......... *A61K 31/795* (2013.01); *A61K 31/155* (2013.01); *A61K 31/195* (2013.01); *A61K 31/198* (2013.01); *A61K 31/64* (2013.01); *A61K 31/78* (2013.01); *A61K 31/785* (2013.01); *A61K 31/787* (2013.01); *A61K 31/80* (2013.01); *A61K 36/16* (2013.01); *A61K 38/26* (2013.01); *A61K 38/28* (2013.01); *A61K 45/06* (2013.01); *A61P 25/28* (2018.01)

(58) Field of Classification Search
None
See application file for complete search history.

(56) References Cited

U.S. PATENT DOCUMENTS

| 7,244,764 | B2 | 7/2007 | Kong et al. | |
|---|---|---|---|---|
| 7,754,761 | B2* | 7/2010 | Kisilevsky | ............ C07C 305/10 514/711 |
| 2007/0010573 | A1 | 1/2007 | Kong et al. | |
| 2007/0265334 | A1* | 11/2007 | Kisilevsky | ........... A61K 47/549 514/711 |
| 2010/0068301 | A1* | 3/2010 | Hutchinson | ............... A61P 3/00 514/564 |
| 2012/0238943 | A1* | 9/2012 | Zare | ..................... A61K 9/0009 604/20 |

FOREIGN PATENT DOCUMENTS

WO    WO-2020010236 A1    1/2020

OTHER PUBLICATIONS

Lanctot, K. et al. Therapy for Alzheimer's disease: how effective are current treatments?, Therapeutic Advances in Neurological Disorders 2009 2 [3] 163-180 (Year: 2009).*
Domingues et al., Therapies for Alzheimer's disease: a metabolic perspective, Molecular Genetics and Metabolism 132 (2021) 162-172 (Year: 2021).*
https://pubchem.ncbi.nlm.nih.gov/compound/Sodium-4-styrenesulfonate (accessed Jul. 12, 2024).*
Aguzzi, A., and Altmeyer, M., "Phase Separation: Linking Cellular Compartmentalization to Disease," Trends in Cell Biology 26(7):547-558, Elsevier Science Publishers, United Kingdom (Jul. 2016).
Aimi, T., et al., "Dextran Sulfate Sodium Inhibits Amyloid-β Oligomer Binding to Cellular Prion Protein," Journal of Neurochemistry 134(4):611-617, International Society for Neurochemistry, United Kingdom (Aug. 2015).
Baertschi, S.W., et al., "Isolation and Structure Elucidation of the Major Degradation Products of Cefaclor Formed Under Aqueous Acidic Conditions," Journal of Pharmaceutical Sciences 86(5):526-539, Elsevier, United States (May 1997).
Caughey, B., and Raymond, G.J., "Sulfated Polyanion Inhibition of Scrapie-associated PrP Accumulation in Cultured Cells," Journal of Virology 67(2):643-650, American Society for Microbiology, United States (Feb. 1993).

(Continued)

*Primary Examiner* — David J Blanchard
*Assistant Examiner* — Sarah J Chickos
(74) *Attorney, Agent, or Firm* — STERNE, KESSLER, GOLDSTEIN & FOX P.L.L.C.; Jeremiah Frueauf; Michael Gross

(57) ABSTRACT

The disclosure provides polymeric compounds that inhibit binding of an amyloid-β-oligomer to cellular prion protein, methods for identifying such compounds, and their therapeutic use. In particular, the present disclosure provides a collection of anionic polymers and methods of using these compounds to treat amyloid-related disorders, e.g., Alzheimer's disease.

19 Claims, 51 Drawing Sheets
Specification includes a Sequence Listing.

(56) References Cited

OTHER PUBLICATIONS

Chung, E., et al., "Anti-PRPC Monoclonal Antibody Infusion as a Novel Treatment for Cognitive Deficits in an Alzheimer's Disease Model Mouse," BMC Neuroscience 11:130, 1-11, Biomed Central, United States (Oct. 2010).

Citron, M., et al., "Mutant Presenilins of Alzheimer's Disease Increase Production of 42-residue Amyloid Beta-protein in Both Transfected Cells and Transgenic Mice," Nature Medicine 3(1):67-72, Nature Publishing Company, United States (Jan. 1997).

Cleary, J.P., et al., "Natural Oligomers of the Amyloid-beta Protein Specifically Disrupt Cognitive Function," Nature Neuroscience 8(1):79-84, Nature Publishing Group, United States (Jan. 2005).

Colby D.W., and Prusiner, S.B., "Prions," Cold Spring Harbor Perspectives in Biology 3(1):a006833, 1-23, Cold Spring Harbor Laboratory Press, United States (Jan. 2011).

Coligan, A.M., et al., (Eds.), "Antibody Detection and Preparation," Immunologic Studies in Humans, in Current Protocols in Immunology, Chapter 7, Unit 7.27, 198 pages, Wiley & Sons, Inc. (1991).

Drummond, E. and Wisniewski, T., "Alzheimer's Disease: Experimental Models and Reality," Acta Neuropathologica 133(2):155-175, Springer Verlag, Germany (Feb. 2017).

Ercanli, T. and Boyd, D.B., "Exploration of the Conformational Space of a Polymeric Material That Inhibits Human Immunodeficiency Virus," Journal of Chemical Information and Modeling 46(3):1321-1333, American Chemical Society, United States (May 2006).

Freir, D.B., et al, "Interaction Between Prion Protein and Toxic Amyloid B Assemblies Can Be Therapeutically Targeted at Multiple Sites," Nature Communications 2:336, pp. 1-9, Springer Nature, Germany (Jun. 2011).

Garcia-Alloza, M., et al., "Characterization of Amyloid Deposition in the APPswe/PS1dE9 Mouse Model of Alzheimer Disease," Neurobiology of Disease 24(3):516-524, Academic Press, United States (Dec. 2006).

Gimbel, D.A., et al., "Memory Impairment in Transgenic Alzheimer Mice Requires Cellular Prion Protein," The Journal of Neuroscience 30(18):6367-6374, Society for Neuroscience, United States (May 2010).

Glenner, G.G., et al., "The Amyloid Deposits in Alzheimer's Disease: Their Nature and Pathogenesis," Applied Pathology 2(6):357-369, Karger, Switzerland (Jan. 1984).

Haas, L.T. and Strittmatter, S.M., "Oligomers of Amyloid B Prevent Physiological Activation of the Cellular Prion Protein-metabotropic Glutamate Receptor 5 Complex by Glutamate in Alzheimer Disease," The Journal of Biological Chemistry 291(33):17112-1721, American Society for Biochemistry and Molecular Biology, United States (Aug. 2016).

Haas, L.T., et al., "Silent Allosteric Modulation of mGluR5 Maintains Glutamate Signaling While Rescuing Alzheimer's Mouse Phenotypes," Cell Reports 20(1):76-88, Cell Press, United States (Jul. 2017).

Haas, L.T., et al., "Metabotropic Glutamate Receptor 5 Couples Cellular Prion Protein to Intracellular Signaling in Alzheimer's Disease," Brain 139(Pt 2):526-546, Oxford University Press, United Kingdom (Feb. 2016).

Haas, L.T., et al, "Therapeutic Molecules and Endogenous Ligands Regulate the Interaction Between Brain Cellular Prion Protein (Prpc) and Metabotropic Glutamate Receptor 5 (MGLUR5)," The Journal of Biological Chemistry 289(41):28460-28477, American Society for Biochemistry and Molecular Biology, United States (Oct. 2014).

Hardy, J., and Selkoe, D.J., "The Amyloid Hypothesis of Alzheimer's Disease: Progress and Problems on the Road to Therapeutics," Science 297(5580):353-356, American Association for the Advancement of Science, United States (Jul. 2002).

Hobi, R., et al., "Anti-HIV-1 Activity in Vitro of Ceftazidime Degradation Products," Antiviral Chemistry & Chemotherapy 12(2):109-118, Sage Publications, United Kingdom (Mar. 2001).

Hyman, A.A., "Liquid-liquid Phase Separation in Biology," Annual Review of Cell and Developmental Biology 30:39-58, Annual Reviews, United States (Oct. 2014).

International Search Report and Written Opinion for International Application No. PCT/US2019/040565, International Search Authority, United States, mailed on Nov. 1, 2019, 10 pages.

Jankowsky, J.L., et al., "Mutant Presenilins Specifically Elevate the Levels of the 42 Residue Beta-amyloid Peptide in Vivo: Evidence for Augmentation of a 42-specific Gamma Secretase," Human Molecular Genetics 13(2):159-70, IRL Press at Oxford University Press, United Kingdom (Jan. 2004).

Janus, C., et al., "A beta Peptide Immunization Reduces Behavioural Impairment and Plaques in a Model of Alzheimer'S Disease," Nature 408(6815):979-982, Nature Publishing Group, United Kingdom (Dec. 2000).

Kaufman, A.C., et al., "Fyn Inhibition Rescues Established Memory and Synapse Loss in Alzheimer Mice," Annals of Neurology 77(6):953-971, Wiley-Liss, United States (Jun. 2015).

Klyubin, I., et al., "Peripheral Administration of a Humanized anti-PrP Antibody Blocks Alzheimer's Disease aβ synaptotoxicity," The Journal of Neuroscience 34(18):6140-6145, Society for Neuroscience, United States (Apr. 2014).

Kostylev, M.A., et al., "Prion-protein-interacting Amyloid-β Oligomers of High Molecular Weight Are Tightly Correlated With Memory Impairment in Multiple Alzheimer Mouse Models," The Journal of Biological Chemistry 290(28):17415-17438, American Society for Biochemistry and Molecular Biology, United States (Jul. 2015).

Lauren, J., et al., "Cellular Prion Protein Mediates Impairment of Synaptic Plasticity by Amyloid-beta Oligomers," Nature 457(7233):1128-1132, Nature Publishing Group, United Kingdom (Feb. 2009).

Lu, D., et al., "Biaryl Amides and Hydrazones as Therapeutics for Prion Disease in Transgenic Mice," The Journal of Pharmacology and Experimental Therapeutics 347(2):325-338, American Society for Pharmacology and Experimental Therapeutics, United States (Nov. 2013).

Miura, Y. and Fukuda, T., "Interaction and Aggregation of Amyloid Beta-Peptide with Multivalent Sulfonated Sugar," Sarantseva, S., editor, Amyloidosis—Mechanisms and Prospects for Therapy, 85-100, InTech, London, United Kingdom (2011).

Morgan, D., et al., "A beta Peptide Vaccination Prevents Memory Loss in an Animal Model of Alzheimer'S Disease," Nature 408(6815):982-985, Nature Publishing Group, United Kingdom (Dec. 2000).

Morris, R., "Developments of a Water-maze Procedure for Studying Spatial Learning in the Rat," Journal of Neuroscience Methods 11(1):47-60, Elsevier/North-Holland Biomedical Press, Netherlands (May 1984).

Ojha, B., et al., "Poly(4-styrenesulfonate) as an Inhibitor of Aβ40 Amyloid Fibril Formation," The Journal of Physical Chemistry. B 117(45):13975-13984, American Chemical Society, United States (Nov. 2013).

Price, D.L., et al., "Alzheimer's Disease: Genetic Studies and Transgenic Models," Annual Review of Genetics 32:461-493, Annual Reviews, United States (Dec. 1998).

Purro, S.A., et al., "Prion Protein as a Toxic Acceptor of Amyloid-β Oligomers," Biological Psychiatry 83(4):358-368, Elsevier, United States (Feb. 2018).

Salazar, S.V., et al., "Conditional Deletion of Prnp Rescues Behavioral and Synaptic Deficits After Disease Onset in Transgenic Alzheimer's Disease," The Journal of Neuroscience 37(38):9207-9221, Society for Neuroscience, United States (Sep. 2017).

Schneider, L.S., et al., "Clinical Trials and Late-stage Drug Development for Alzheimer's Disease: an Appraisal From 1984 to 2014," Journal of Internal Medicine 275(3):251-283, Blackwell Scientific Publications, United Kingdom (Mar. 2014).

Shankar, G.M., et al., "Amyloid-beta Protein Dimers Isolated Directly From Alzheimer's Brains Impair Synaptic Plasticity and Memory," Nature Medicine 14(8):837-842, Nature Publishing Company, United States (Aug. 2008).

Smetsers, T.F., et al., "Localization and Characterization of Melanoma-associated Glycosaminoglycans: Differential Expression of Chondroitin

(56) References Cited

OTHER PUBLICATIONS and Heparan Sulfate Epitopes in Melanoma," Cancer Research 63(11):2965-2670, American Association for Cancer Research, United States (Jun. 2003).

Smith, L.M., et al., "Binding Sites for Amyloid-β Oligomers and Synaptic Toxicity," Cold Spring Harbor Perspectives in Medicine 7(5):a024075, pp. 1-19, Cold Spring Harbor Laboratory Press, United States (May 2017).

Smith, L.M., et al., "Disease-modifying Benefit of Fyn Blockade Persists After Washout in Mouse Alzheimer's Model," Neuropharmacology 130:54-61, Pergamon Press, United Kingdom (Mar. 2018).

Sonati, T., et al., "The Toxicity of Antiprion Antibodies is Mediated by the Flexible Tail of the Prion Protein," Nature 501(7465):102-106, Nature Publishing Group, United Kingdom (Sep. 2013).

Um, J.W., et al., "Alzheimer Amyloid-β Oligomer Bound to Postsynaptic Prion Protein Activates Fyn to Impair Neurons," Nature Neuroscience 15(9):1227-1235, Nature Publishing Group, United States (Sep. 2012).

Um, J.W., "Metabotropic Glutamate Receptor 5 is a Coreceptor for Alzheimer aβ Oligomer Bound to Cellular Prion Protein," Neuron 79(5):887-902, Cell Press, United States (Sep. 2013).

Zahn, H., and Gattner, H.G., "Hair Sulfur Amino Acid Analysis," EXS 78:239-258, Birkhauser Verlag, Switzerland (Jan. 1997).

Zhang, X., et al., "RNA Stores Tau Reversibly in Complex Coacervates," Plos Biology 15(7):e2002183, 1-28, Public Library of Science, United States (Jul. 2017).

\* cited by examiner

| Element | MW | SEC purification % in Z 1A | % in Z 1B | AIE purification % in Z 2A | % in Z 2B | Avg. % sample Z | molar ratio | formula (1 sulfur) | formula (2 sulfurs) |
|---|---|---|---|---|---|---|---|---|---|
| C | 12.011 | 38.54 | 38.70 | 39.07 | 39.22 | 38.88 | 3.2 | 7.8 | 15.5 |
| H | 1.008 | 4.38 | 4.45 | 4.48 | 4.57 | 4.47 | 4.4 | 10.6 | 21.3 |
| N | 14.007 | 12.57 | 12.62 | 12.69 | 12.80 | 12.67 | 0.9 | 2.2 | 4.3 |
| S | 32.065 | 13.35 | 13.28 | 13.5 | - | 13.38 | 0.4 | 1.0 | 2.0 |
| O | 15.999 | - | - | - | - | 30.60 | 1.9 | 4.6 | 9.2 |
| Calculated MW | | | | | | | | 239.7 | 479.4 |

FIG. 48

| | Element | MW | monomer | theoretical % | molar ratio | formula (1 sulfur) | formula (2 sulfurs) |
|---|---|---|---|---|---|---|---|
| 1 | C | 12.011 | | 44.59 | 3.7 | 11 | - |
| | H | 1.008 | | 4.08 | 4.0 | 12 | - |
| | N | 14.007 | | 18.91 | 1.3 | 4 | - |
| | S | 32.065 | | 10.82 | 0.3 | 1 | - |
| | O | 15.999 | | 21.60 | 1.3 | 4 | - |
| | Calculated MW | | | | | 296.31 | |
| 2 | C | 12.011 | | 43.53 | 3.6 | - | 16 |
| | H | 1.008 | | 4.34 | 4.3 | - | 19 |
| | N | 14.007 | | 15.86 | 1.1 | - | 5 |
| | S | 32.065 | | 14.53 | 0.5 | - | 2 |
| | O | 15.999 | | 21.74 | 1.4 | - | 6 |
| | Calculated MW | | | | | | 441.49 |

FIG. 49

| Element | MW | avg % sample Z | molar ratio | formula (1 sulfur) | formula candidate 1 | formula (2 sulfurs) | formula candidate 2 |
|---|---|---|---|---|---|---|---|
| C | 12.011 | 36.56 | 3.0 | 7.6 | 11 | 15.2 | 16 |
| H | 1.008 | 4.26 | 4.2 | 10.6 | 12 | 21.1 | 19 |
| N | 14.007 | 12.03 | 0.9 | 2.1 | 4 | 4.3 | 4 |
| S | 32.065 | 12.49 | 0.4 | 1.0 | 2 | 2.0 | 2 |
| O | 15.999 | 18.75 | 1.2 | 2.9 | 4 | 5.9 | 6 |
| Na | 23.000 | 5.92 | 0.3 | - | - | - | - |
| H$_2$O | 18.016 | 18.75 | 0.6 | - | - | - | - |
| Calculated MW | | | | 211.04 | 296.31 (28.8% error) | 422.08 | 441.49 (4.4% error) |

FIG. 50

SEQUENCE LISTING

```
<160> NUMBER OF SEQ ID NOS: 3

<210> SEQ ID NO 1
<211> LENGTH: 42
<212> TYPE: PRT
<213> ORGANISM: Artificial Sequence
<220> FEATURE:
<223> OTHER INFORMATION: human Amyloid-beta peptide 1-42 (Swiss-Prot:
      P05067.3)

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 214
<212> TYPE: PRT
<213> ORGANISM: Artificial Sequence
<220> FEATURE:
<223> OTHER INFORMATION: human mature Cellular Prion Protein sequence
      (GenBank: AAH22532.1)

<400> SEQUENCE: 2

Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
            20                  25                  30

Gly Gly Trp Gly Gln Pro His Gly Gly Gly Trp Gly Gln Pro His Gly
        35                  40                  45

Gly Gly Trp Gly Gln Pro His Gly Gly Gly Trp Gly Gln Pro His Gly
    50                  55                  60

Gly Gly Trp Gly Gln Gly Gly Gly Thr His Ser Gln Trp Asn Lys Pro
65                  70                  75                  80

Ser Lys Pro Lys Thr Asn Met Lys His Met Ala Gly Ala Ala Ala Ala
                85                  90                  95

Gly Ala Val Val Gly Gly Leu Gly Gly Tyr Val Leu Gly Ser Ala Met
            100                 105                 110

Ser Arg Pro Ile Ile His Phe Gly Ser Asp Tyr Glu Asp Arg Tyr Tyr
        115                 120                 125
```

```
Arg Glu Asn Met His Arg Tyr Pro Asn Gln Val Tyr Tyr Arg Pro Met
        130                 135                 140

Asp Glu Tyr Ser Asn Gln Asn Asn Phe Val His Asp Cys Val Asn Ile
145                 150                 155                 160

Thr Ile Lys Gln His Thr Val Thr Thr Thr Lys Gly Glu Asn Phe
                165                 170                 175

Thr Glu Thr Asp Val Lys Met Met Glu Arg Val Val Glu Gln Met Cys
                180                 185                 190

Ile Thr Gln Tyr Glu Arg Glu Ser Gln Ala Tyr Tyr Lys Arg Gly Ser
            195                 200                 205

Ser Met Val Leu Phe Ser
    210
```

<210> SEQ ID NO 3
<211> LENGTH: 215
<212> TYPE: PRT
<213> ORGANISM: Artificial Sequence
<220> FEATURE:
<223> OTHER INFORMATION: mature mouse Cellular Prion Protein sequence
      (GenBank: AAA39996.1)

<400> SEQUENCE: 3

```
Lys Lys Arg Pro Lys Pro Gly Gly Trp Asn Thr Gly Gly Ser Arg Tyr
1               5                   10                  15

Pro Gly Gln Gly Ser Pro Gly Gly Asn Arg Tyr Pro Pro Gln Gly Gly
            20                  25                  30

Thr Trp Gly Gln Pro His Gly Gly Trp Gly Gln Pro His Gly Gly
        35                  40                  45

Ser Trp Gly Gln Pro His Gly Gly Ser Trp Gly Gln Pro His Gly Gly
    50                  55                  60

Gly Trp Gly Gln Gly Gly Gly Thr His Asn Gln Trp Asn Lys Pro Ser
65                  70                  75                  80

Lys Pro Lys Thr Asn Leu Lys His Val Ala Gly Ala Ala Ala Ala Gly
                85                  90                  95

Ala Val Val Gly Gly Leu Gly Gly Tyr Met Leu Gly Ser Ala Val Ser
            100                 105                 110

Arg Pro Met Ile His Phe Gly Asn Asp Trp Glu Asp Arg Tyr Tyr Arg
        115                 120                 125

Glu Asn Met Tyr Arg Tyr Pro Asn Gln Val Tyr Tyr Arg Pro Val Asp
        130                 135                 140

Gln Tyr Ser Asn Gln Asn Asn Phe Val His Asp Cys Val Asn Ile Thr
145                 150                 155                 160

Ile Lys Gln His Thr Val Thr Thr Thr Lys Gly Glu Asn Phe Thr
            165                 170                 175

Glu Thr Asp Val Lys Met Met Glu Arg Val Val Glu Gln Met Cys Val
            180                 185                 190

Thr Gln Tyr Gln Lys Glu Ser Gln Ala Tyr Tyr Asp Gly Arg Arg Ser
        195                 200                 205

Ser Ser Thr Val Leu Phe Ser
    210                 215
```

METHODS AND COMPOSITIONS FOR THE TREATMENT OF AMYLOID-RELATED DISORDERS

GOVERNMENT SUPPORT

This invention was made with government support under AG034924 awarded by National Institutes of Health. The government has certain rights in the invention

FIELD OF THE INVENTION

The disclosure provides methods of using anionic polymers that inhibit the binding of Aβ-oligomer to cellular prion protein to treat amyloid-related disorders, e.g., Alzheimer's disease.

BACKGROUND OF THE INVENTION

Alzheimer's disease (AD) currently afflicts over five million individuals in the United States, and the incidence of AD is expected to increase over the next several decades as the size of the elderly population increases. One prominent symptom of AD is memory loss. Memory loss is often an early symptom of the disease and is followed by global cognitive decline over time. Additional features of AD include a high density of amyloid plaques, neurofibrillary tangles, neuronal loss, and brain atrophy. The occurrence of neuronal loss and brain atrophy can, in certain instances, be prominent in the hippocampus, temporal cortex and associated areas.

A major constituent of extracellular plaque is amyloid-β (Aβ) peptide having 40-42 amino acids. Aβ peptide is produced in vivo by proteolytic cleavage Amyloid Precursor Protein (APP). Neurofibrillary tangles are intracellular, paired helical filaments composed principally of hyperphosphorylated forms of the microtubule-associated protein, Tau. The number of plaques and tangles are substantially elevated in subjects suffering from AD.

The "Amyloid Hypothesis" of AD postulates that Aβ peptide accumulates in AD patients and attributes to the development of AD. See, for example, Glenner et al. in *Appl. Pathol.* (1984) vol. 2, 357-369; and Hardy et al. in Science (2002) vol. 297, 353-356. Several observations support the Amyloid Hypothesis. One observation is that familial cases of early onset AD are caused by mutations in the APP gene containing the Aβ sequence, or in the presenilin genes that encode a component of the gamma-secretase enzyme necessary for the intramembranous cleavage of APP to release Aβ. See, for example, Price et al. in *Ann. Rev. Genet.* (1998) vol. 32, 461-493. Moreover, transgenic expression of these human disease-causing genes in mice produces the deposition of Aβ plaque and progressive spatial memory defects. Id. Immunization against Aβ peptide reverses memory deficits in the mouse models. See, for example, Morgan et al. in Nature (2000), vol. 408, 982-985; and Janus et al. in Nature (2000) vol. 408, 979-982. Further support for the Amyloid Hypothesis of AD is that certain Aβ species produce memory dysfunction when injected into brain tissue of otherwise healthy rodents. See, for example, Shankar et al. in *Nat. Med.* (2008) vol. 14, 837-842; and Cleary et al. in *Nat. Neurosci.* (2005) vol. 8, 79-84.

Despite the advances made in understanding and treating Alzheimer's disease, the need remains for more efficacious therapeutic options for treating amyloid-related disorders, such as Alzheimer's disease. The present disclosure addresses this need and provides other related advantages.

Cellular Prion Protein ($PrP^C$) was identified as an Aβ-oligomer (ADDL) receptor by expression cloning. See Lauren et al. in Nature (2009) vol. 457, 1128-1132. The pathway was discovered by searching for a brain-expressed gene capable of producing a protein that can capture amyloid-β oligomer on the surface of cells. In particular, in a brain slice assay that mimics memory formation in the brain, Prion Protein was essential for amyloid-β oligomer to exert its damaging effect. Thus, after production of amyloid-β oligomers, the first step in the AD process involves binding to neurons via Prion Protein. See FIG. 2. This result indicates that the mechanisms of neurodegeneration in AD and infectious Prion diseases, such as Creuzfeldt Jacob disease and "mad cow" disease, may share similar pathway components for neuronal degeneration, even if the inciting events are different.

Aβ-oligomers bind $PrP^C$ with nanomolar affinity. Moreover, it has been determined that anti-PrP antibodies prevent Aβ-oligomer binding to $PrP^C$ and rescue synaptic plasticity in hippocampal slices from oligomeric Aβ. These results indicate that $PrP^C$ is a mediator of Aß-oligomer-induced synaptic dysfunction, and that $PrP^C$-specific pharmaceuticals will have therapeutic potential for treating and preventing amyloid-related disorders, such as Alzheimer's disease.

The practice of the present disclosure employs, unless otherwise indicated, techniques of organic chemistry, pharmacology, molecular biology (including recombinant techniques), cell biology, biochemistry, and immunology. Such techniques are explained, for example, in "Comprehensive Organic Synthesis" (B. M. Trost & I. Fleming, eds., 1991-1992); "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety. Various aspects of the disclosure are set forth below in sections; however, aspects of the disclosure described in one particular section are not to be limited to any particular section.

Certain polymers inhibit the conversion of cellular PrP ($PrP^C$) to the scrapie conformation ($PrP^{Sc}$) responsible for transmissible spongiform encephalopathies (TSE). Specifically, dextran sulfate sodium (DSS) and pentosan polysulfate (PPS) exhibit anti-prion activity in vitro (Caughey and Raymond, 1993). DSS and PPS possess groups of relative charge and hydrophobicity, suggesting they may also possess Aßo/$PrP^C$ inhibitory activity. Indeed, DSS has been reported to be partially inhibitory of Aßo/$PrP^C$ interaction (Aimi et al., 2015). There exists a need for more potent $PrP^C$ competitive antagonists of the Aßo/$PrP^C$ interaction.

BRIEF SUMMARY OF THE INVENTION

The anionic polymers of the present disclosure are surprising potent inhibitors of the Aßo/$PrP^C$ interaction. For example, compound Z and PSCMA, see below, blocked $Prp^{Sc}$ propagation in N2A culture, with PSCMA exhibiting an $IC_{50}$ between 10 and 40 nM to clear $PrP^{Sc}$ from neuroblastoma cells. To the extent that the $PrP^C$ N-terminus Aβo-binding domains are required for interaction with these compounds, inhibition of $PrP^{Sc}$ propagation by these compounds implicates the N-terminus domains in the prion formation propensity of $PrP^C$. Moreover, BID oral administration of 40 mpk PSCMA yields approximately 40 nM PSCMA in mouse brain. Thus, PSCMA and the other polymers described herein may be used to inhibit TSE. Because all the biochemical assays described herein utilized human full length $PrP^C$, and the functional AD assays were in systems involving rodent $PrP^C$, these polymers act across species . . .

Thus, in one aspect, the disclosure provides methods of treating or preventing an amyloid-related disorder in a subject comprising administering to a subject in need thereof a therapeutically effective amount of an anionic polymer.

A variety of amyloid-related disorders can be treated or prevented using the methods described herein. For example, the amyloid-related disorder can be Alzheimer's disease, senile systemic amyloidosis, cerebral amyloid angiopathy, Parkinson's disease, rheumatoid arthritis, Huntington's disease, medullary thyroid cancer, cardiac arrhythmia (dysrhythmia), atherosclerosis, polactinoma, familial amyloid polyneuropathy, heredity non-neuropathic systemic amyloidosis (Ostertag type), Beta 2 microglobulin amyloidosis, Finnish type amyloidosis, lattice dystrophy, cerebral amyloid angiopathy (congophilic angiopathy), systemic AL amyloidosis, sporadic inclusion body myositis, phaeochromocytoma, osteomyelitis, multiple myeloma, type II diabetes, scrapie, bovine spongiform encephalitis, Creutzfeldt Jakob disease, Gerstmann Sträussler Scheinker syndrome, fatal familial insomnia, kuru, a prion protein related disorder, memory impairment, localized amyloidosis, or systemic amyloidosis.

Another aspect of the disclosure provides a method of blocking a cellular Prion Protein receptor. The method comprises exposing a cellular Prion Protein receptor to a polymer described herein to block the cellular Prior Protein receptor. In certain embodiments, the blocking inhibits binding of an amyloid-β-oligomer to the cellular Prion Protein receptor.

BRIEF DESCRIPTION OF FIGURES

FIG. 48 is a table showing the elemental analysis performed for compound Z purified from crude aged ceftazidime by size exclusion chromatography (SEC) or anion exchange chromatography (AIE).

FIG. 49 is a table showing the two prospective Z monomer subunit structures.

FIG. 50 is a table showing the elemental composition of the formulae for candidate 1 and 2 calculated by taking into account prospective water and sodium ion in the elemental analysis.

DETAILED DESCRIPTION OF THE INVENTION

Figure 1:
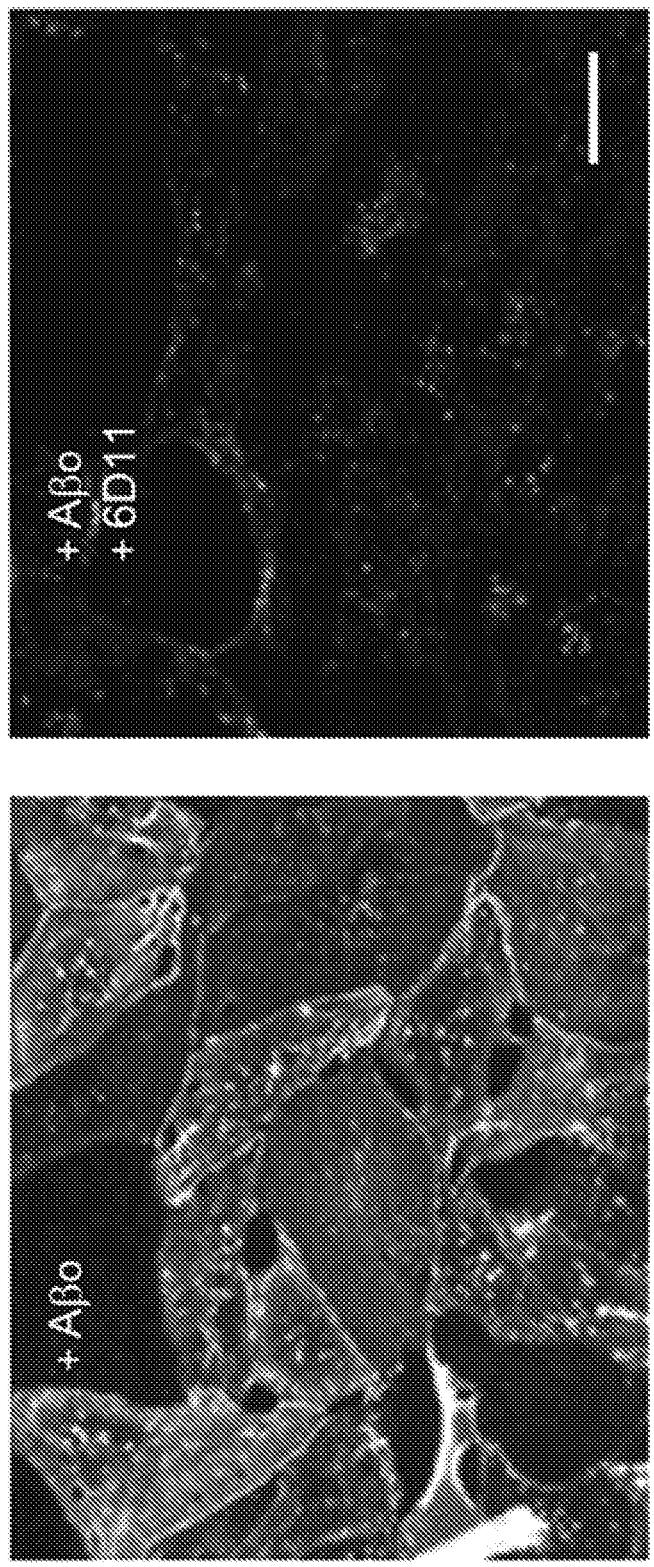
FIG. 1 is two illustrations showing that human stably $PrP^C$-transfected CV1 cells treated with biotinylated Aβo (~20 nM Aβo, 1 μM Aβ monomer equivalent) followed by 555-streptavidin exhibit signal that is inhibited by the 6D11 antibody (1 μg/ml) directed against the $PrP^C$ 90-111 Aβo-binding domain. Scale bar=5 μ.

In one embodiment, the disclosure provides anionic polymers for use in inhibiting binding of Aß-oligomer to cellular prion protein, methods of using these polymers to treat amyloid-related disorders or blocking the cellular prion protein receptor, and methods and kits for identifying compounds capable of inhibiting binding of Aß-oligomer to cellular prion protein. Binding of Aß-oligomer to cellular prion protein has been reported to contribute to the progress of various neurodegenerative disorders, e.g., Alzheimer's Disease. Anionic polymers are, inter alia, capable of blocking binding of Aß-oligomer to cellular prion protein, and thus provide a therapeutic benefit in the treatment and prevention of amyloid-related disorders.

I. Definitions

To facilitate an understanding of the present disclosure, a number of terms and phrases are defined below.

The terms "a," "an" and "the" as used herein mean "one or more" and include the plural unless the context is inappropriate.

The term "Aβ-oligomer" is an art-recognized term and refers to a covalent or non-covalent association of two or more (e.g., 10, 20, 50, 100 or the like) amyloid-beta polypeptide units. In certain preferred embodiments, the amyloid-beta polypeptide units comprise the primary amino acid sequence of human Amyloid-beta peptide 1-42 (daefrhdsgy evhhqklvff aedvgsnkga iiglmvggvv ia) (Swiss-Prot: P05067.3) (SEQ. ID No. 1), or comprise an amino acid sequence sharing at least 80% (85% or 90%) amino acid identity over at least 25 consecutive residues of human Amyloid-beta peptide 1-42. In certain further preferred embodiments, the Aβ-oligomer is characterized in that it remains soluble in water (e.g., does not sediment after 30 minutes of centrifugation at 100,000×g).

The term "cellular prion protein" is art-recognized and refers to the native prion protein molecule naturally expressed in mammals. In certain preferred embodiments, the cellular prion protein is a protein preparation comprising i) a polypeptide segment of at least 70% (or more preferably 80%, 85% or 90%) amino acid identity over at least 70 consecutive residues of the human mature Cellular Prion Protein sequence

```
                                          (SEQ. ID NO. 2)
(kkrpkpgg wntggsrypg qgspggnryp pqggggwgqp hgggwgqphg ggwgqphggg wgqphgggwg qgggthsqwn kpskpktnmk hmagaaaaga vvgglggyvl gsamsrpiih fgsdyedryy renmhrypnq vyyrpmdeys nqnnfvhdcv nitikqhtvt tttkgenfte tdvkmmervv eqmcitqyer esqayykrgs smvlfs) (GenBank: AAH22532.1),
``` or ii) a polypeptide segment of at least 70% (or more preferably 80%, 85% or 90%) amino acid identity over at least 70 consecutive residues of the mature mouse Cellular Prion sequence

```
                                          (SEQ. ID NO. 3)
(kkrpkpgg wntggsrypg qgspggnryp pqggtwgqph gggwgqphgg swgqphggsw gqphgggwgq gggthnqwnk pskpktnlkh vagaaaagav vgglggymlg savsrpmihf gndwedryyr enmyrypnqv yyrpvdqysn qnnfvhdcvn
```

```
itikqhtvtt ttkgenftet dvkmmervve qmcvtqyqke sqayydgrrs sstvlfs) (GenBank: AAA39996.1).
```

The term "treating" includes any effect, e.g., lessening, reducing, modulating, ameliorating or eliminating, that results in the improvement of the condition, disease, disorder, and the like, or ameliorating a symptom thereof.

The terms "individual," "patient," or "subject" are used interchangeably and include to any animal, including mammals, preferably mice, rats, other rodents, rabbits, dogs, cats, swine, cattle, sheep, horses, or primates, and most preferably humans. The anionic polymers of the disclosure can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

The term "therapeutically effective amount" means the amount of the subject compound that will elicit the biological or medical response of a tissue, system, animal or human that is being sought by the researcher, veterinarian, medical doctor or other clinician. The anionic polymers of the disclosure are administered in therapeutically effective amounts to treat a disease. Alternatively, a therapeutically effective amount of a compound is the quantity required to achieve a desired therapeutic and/or prophylactic effect, such as an amount which results in the prevention of or a decrease in the symptoms of an amyloid-related disorder.

The term "amyloid-related disorder" refers to medical disorders associated with the accumulation of amyloid which can either be restricted to one organ, "localized amyloidosis", or spread to several organs, "systemic amyloidosis." Secondary amyloidosis may be associated with chronic infection (such as tuberculosis) or chronic inflammation (such as rheumatoid arthritis), including a familial form of secondary amyloidosis which is also seen in Familial Mediterranean Fever (FMF) and another type of systemic amyloidosis found in long-term hemodialysis patients. Localized forms of amyloidosis include, without limitation, type II diabetes and any related disorders thereof, neurodegenerative diseases such as scrapie, transmissible spongiform encephalopathies (TSEs, also known as prion diseases, which in some circumstances may involve a Spiroplasma infection) (e.g., bovine spongiform encephalitis, Creutzfeldt-Jakob disease, Gerstmann-Sträussler-Scheinker syndrome, fatal familial insomnia, and kuru), Alzheimer's disease, senile systemic amyloidosis (SSA), Cerebral Amyloid Angiopathy, Parkinson's disease, prion protein related disorders (e.g., prion-related encephalopathies), rheumatoid arthritis, Huntington's disease, medullary thyroid cancer, cardiac arrhythmia (dysrhythmia), atherosclerosis, polactinoma, familial amyloid polyneuropathy (FAP or Corino de Andrade's disease, a form of Paramyloidosis), heredity non-neuropathic systemic amyloidosis (Ostertag-type), Beta-2-microglobulin amyloidosis, Finnish type amyloidosis, lattice dystrophy, cerebral amyloid angiopathy (congophilic angiopathy), systemic AL amyloidosis, sporadic inclusion body myositis (sIBM), phaeochromocytoma (PCC or pheochromocytoma), osteomyelitis, and multiple myeloma.

The phrases "block the cellular Prion Protein Receptor" or "blocking the cellular Prion Protein Receptor" refer to the condition where an organic compound described herein binds to the cellular Prion Protein Receptor such that in a population of cellular Prion Protein Receptors at least 30% of the cellular Prion Protein Receptors in the population are unable to bind amyloid-β oligomer due to binding of the organic compound to the cellular Prion Protein Receptor. In certain preferred embodiments, in a population of cellular Prion Protein Receptors at least 40%, 50%, 60%, 70%, 80%, 90% or 95% of the cellular Prion Protein Receptors in the population are unable to bind amyloid-β oligomer due to binding of the organic compound to the cellular Prion Protein Receptor.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

As used herein, the term "pharmaceutically acceptable salt" refers to any pharmaceutically acceptable salt (e.g., acid or base) of a compound of the present disclosure which, upon administration to a subject, is capable of providing a compound of this disclosure or an active metabolite or residue thereof. As is known to those of skill in the art, "salts" of the compounds of the present disclosure may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the disclosure and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present disclosure compounded with a suitable cation such as $Na^+$, $NH_4^+$, and $NW_4^+$ (wherein W is a $C_{1-4}$ alkyl group), and the like.

For therapeutic use, salts of the compounds of the present disclosure are contemplated as being pharmaceutically acceptable. However, salts of acids and bases that are non-pharmaceutically acceptable may also find use, for example, in the preparation or purification of a pharmaceutically acceptable compound.

II. Anionic Polymers

The term "polymer" as used herein refers to a molecule of high relative molecular mass comprising repeating units (monomers) derived from molecules of low relative molecular mass. The polymer may be a homopolymer or a heteropolymer.

The term "homopolymer" as used herein refers to a polymer derived from one species of monomer.

The term "heteropolymer" as used herein refers to a polymer derived from two or more species of monomer.

The term "anionic polymer" or "acidic polymer" as used herein refers to a polymer which has at least one constitutional repeating unit containing a sulphate, or a salt thereof; a sulphonate, or a salt thereof; a carboxylate, or a salt thereof; a phosphate, or a salt thereof; or borate group, or a salt thereof. Collectively, a sulphate, or a salt thereof; a sulphonate, or a salt thereof; a carboxylate, or a salt thereof; a phosphate, or a salt thereof; or borate group, or a salt thereof, are referred to herein as an "acidic group." In one embodiment, the anionic polymer has at least one constitutional repeating unit containing a sulphonate or carboxylate group, or a salt thereof.

The terms "constitutional repeating unit" or "monomer" as used herein refers to the minimal structural units of a polymer. Nonlimiting exemplary anionic constitutional repeating units include acrylic acid, or a salt thereof;

methacrylic acid, or a salt thereof;

maleic acid, or a salt thereof;

fumaric acid, or a salt thereof;

ethylsulphonic acid, or a salt thereof;

vinylsulphonic acid, or a salt thereof;

vinylsulphonic acid, or a salt thereof;

styrenesulphonic acid, or a salt thereof;

vinylphenylsulphuric acid, or a salt thereof;

2-methacryloyloxyethane sulphonic acid, or a salt thereof;

3-methacryloyloxy-2-hydroxypropanesulphonic acid, or a salt thereof;

3-methacryl amido-3-methylbutanoic acid, or a salt thereof;

acrylamidomethylpropanesulfonic acid, or a salt thereof;

vinylphosphoric acid, or a salt thereof;

4-vinylbenzoic acid, or a salt thereof;

3-vinyl oxypropane-1-sulphonic acid, or a salt thereof; or

N-vinylsuccinimidic acid, or a salt thereof.

The term "anionic heteropolymer" as used herein refers to anionic polymer comprising two or more different constitutional repeating units. In one embodiment, the acidic heteropolymer contains at least two constitutional repeating units containing an acidic group. In another embodiment, the acidic heteropolymer contains at least one constitutional repeating unit containing an acidic group and at least one constitutional repeating unit that does not contain an acidic group, e.g., a constitutional repeating group having an unsubstituted phenyl, e.g.,

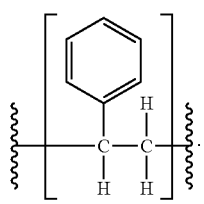

Thus, not every constitutional repeating unit has to comprise a sulphate, sulphonate, carboxylate, phosphate, or borate group, or a salt thereof. An exemplary anionic heteropolymer is poly (styrene-alt-maleic acid) sodium salt.

The term "anionic homopolymer" as used herein refers to acid polymer comprising a single constitutional repeating unit containing an acidic group.

In one embodiment, the polyanionic polymers of the disclosure comprise, on average, about 100 to about 20,000 monomers. In another embodiment, the polyanionic polymers of the disclosure comprise, on average, about 100 to about 10,000 monomers.

In one embodiment, the polyanionic polymers of the disclosure have a molecular weight, on average of about 3000 Da to about 200000 Da. In another embodiment, the polyanionic polymers of the disclosure have a molecular weight, on average of about 20000 Da to about 100000 Da. In another embodiment, the polyanionic polymer (e.g., PSCMA) has a narrow molecular weight average of 3000 Da±500 Da, or 4000 Da±500 Da, or 5000 Da±500 Da, or 6000 Da±500 Da, or 8000 Da±500 Da, or 10000 Da±500 Da, or 15000 Da±500 Da, or 20000 Da±500 Da or 30000 Da±1000 Da. In another embodiment, the polyanionic polymer (e.g., PSCMA) has a broad molecular weight of 3000 Da±2000 Da, or 4000 Da±3000 Da, or 5000 Da±3000 Da, or 6000 Da±4000 Da, or 8000 Da±5000 Da, or 10000 Da±6000 Da, or 15000 Da±10000 Da, or 20000 Da #15000 Da or 30000 Da±20000 Da. In another embodiment, the polyanionic polymer (e.g., PSCMA) has a molecular weight that is a combination or permutation of the above set of specified molecular weights.

III. Therapeutic Applications

The anionic polymers described above can be used to treat disease and disorders, or block the cellular Prion Protein Receptor. Exemplary non-limiting features of these contemplated uses are described below.

The anionic polymers described herein provide therapeutic benefits in treating or preventing amyloid-related disorders. Accordingly, in one embodiment, the disclosure provides a method of treating or preventing an amyloid-related disorder in a subject comprising administering to a subject in need thereof a therapeutically effective amount of an anionic polymer described herein.

In one embodiment, the anionic polymer is not dextran sulfate or dextran sulfate sodium.

In one embodiment, the anionic polymer is not pentosan polysulfate or pentosan polysulfate sodium.

In one embodiment, the anionic polymer is an anionic heteropolymer.

In another embodiment, the anionic polymer is an anionic homopolymer.

In another embodiment, the anionic polymer is selected from the group consisting of polystyrene sulfonic acid, or the sodium salt thereof; poly (styrene-co-maleic acid) partial isobutyl ester, or the sodium salt thereof; polystyrene sulfonic acid, or the sodium salt thereof; poly (2-acrylamido-2-methyl-1-propanesulfonic acid), or the sodium salt thereof; poly (styrene-alt-maleic acid), or the sodium salt thereof; and poly(4-styrenesulfonic acid-co-maleic acid), or the sodium salt thereof.

In another embodiment, the anionic polymer is selected from the group consisting of polystyrene sulfonic acid sodium salt, poly (styrene-co-maleic acid) partial isobutyl ester, polystyrene sulfonic acid sodium salt, poly (2-acrylamido-2-methyl-1-propanesulfonic acid), poly (styrene-alt-maleic acid) sodium salt, and poly(4-styrenesulfonic acid-co-maleic acid) sodium salt.

In another embodiment, the anionic polymer is polystyrene sulfonic acid sodium salt.

In another embodiment, the anionic polymer is poly (styrene-co-maleic acid) partial isobutyl ester.

In another embodiment, the anionic polymer is poly (2-acrylamido-2-methyl-1-propanesulfonic acid).

In another embodiment, the anionic polymer is poly (styrene-alt-maleic acid) sodium salt.

In another embodiment, the anionic polymer is poly (4-styrenesulfonic acid-co-maleic acid) sodium salt.

A wide variety of amyloid-related disorders can be treated or prevented using the anionic polymers described above. For example, the amyloid-related disorder can be Alzheimer's disease, senile systemic amyloidosis, cerebral amyloid angiopathy, Parkinson's disease, rheumatoid arthritis, Huntington's disease, medullary thyroid cancer, cardiac arrhythmia (dysrhythmia), atherosclerosis, polactinoma, familial amyloid polyneuropathy, heredity non-neuropathic systemic amyloidosis (Ostertag type), Beta 2 microglobulin amyloidosis, Finnish type amyloidosis, lattice dystrophy, cerebral amyloid angiopathy (congophilic angiopathy), systemic AL amyloidosis, sporadic inclusion body myositis, phaeochromocytoma, osteomyelitis, multiple myeloma, type II diabetes, scrapie, bovine spongiform encephalitis, Creutzfeldt Jakob disease, Gerstmann Sträussler Scheinker syndrome, fatal familial insomnia, kuru, a prion protein related disorder, memory impairment, localized amyloidosis, or systemic amyloidosis. In certain embodiments, the amyloid-related disorder is Alzheimer's disease.

The therapeutic methods described herein embrace combination therapy. For example, in certain embodiments, the method further comprises administering to the patient a therapeutically effective amount of a second therapeutic agent, such as a therapeutic agent selected from the group consisting of a cholinesterase inhibitor, an antioxidant Ginkobiloba extract, a nonsteroidal anti-inflammatory agent, a non-specific NMDA antagonist, carbidopa/levodopa, a dopamine agonist, a COMT inhibitor, an anticholinergic, a MAO inhibitor, a biguanide, a glucosidase inhibitor, insulin, a meglitinide, a sulfonylurea, a biguanide/glyburide combination, a thiozolidinedione, a PPAR-alpha agonist, a PPAR-gamma agonist, a PPAR alpha/gamma dual agonist, a SGLT2 inhibitor, an inhibitor of fatty acid binding protein (aP2), a glucagon-like peptide-1 (GLP-1), and a dipeptidyl peptidase IV (DP4) inhibitor.

In certain instances, when the disorder being treated or prevented is Alzheimer's disease, the antioxidant can be Ginko biloba extract, and the non-specific NMDA antagonist can be Ebixa® (Memantine). In the case of Parkinson's disease, the second therapeutic agent may be carbidopa/levodopa, which controls temor, bradykinesia, balance, and rigidity. Other therapies for Parkinson's disease include dopamine agonists, carbidopa/levodopa therapy, COMT inhibitors, anticholinergics, and MAO inhibitors such as selegiline/deprenyl. In the case of Type II diabetes, the second therapeutic agent may be a biguanide (e.g., metformin), glucosidase inhibitor (e.g., acarbose), insulin (including insulin secretagogues or insulin sensitizers), a meglitinide (e.g., repaglinide), a sulfonylurea (e.g., glimepiride, glyburide and glipizide), biguanide/glyburide combinations (e.g., glucovance), a thiozolidinedione (e.g., troglitazone, rosiglitazone and pioglitazone), a PPAR-alpha agonist, a PPAR-gamma agonist, a PPAR alpha/gamma dual agonist, a SGLT2 inhibitor, an inhibitor of fatty acid binding protein (aP2), a glucagon-like peptide-1 (GLP-1), and a dipeptidyl peptidase IV (DP4) inhibitor.

In certain embodiments, the subject is a human.

IV. Pharmaceutical Compositions and Dosing Considerations

In another aspect, the present disclosure provides pharmaceutically acceptable compositions which comprise a therapeutically-effective amount of one or more of the polymers described above, formulated together with one or more pharmaceutically acceptable carriers (additives) and/or diluents. As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) intrathecally; or (10) intracranially.

In one embodiment, the anionic polymer, or a pharmaceutically acceptable salt thereof, is administered to the subject as a pharmaceutical composition comprising one or more pharmaceutically acceptable carriers. In another embodiment, the pharmaceutical composition comprises hydroxypropyl methylcellulose. In another embodiment, the pharmaceutical composition comprises polysorbate 80. In another embodiment, the pharmaceutical composition comprises about 0.1% to about 1% w/v hydroxypropyl methylcellulose and about 0.05% to about 0.5% w/v polysorbate 80. In another embodiment, the pharmaceutical composition comprises about 0.5% w/v hydroxypropyl methylcellulose and about 0.1% w/v polysorbate 80.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present disclosure include those suitable for oral, nasal, topical (including buccal and sublingual), rectal, intrathecal, intracranial, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present disclosure comprises an excipient selected from the group consisting of phosphate buffered saline solution (PBS), cyclodextrins, celluloses, liposomes, micelle forming agents, e.g., bile acids, and polymeric carriers, e.g., polyesters and polyanhydrides; and a compound of the present disclosure. In certain embodiments, an aforementioned formulation renders orally bioavailable a compound of the present disclosure.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more compounds of the disclosure in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the disclosure include water, phosphate buffered saline solution (PBS), ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present disclosure are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present disclosure may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a polymer of the disclosure will be that amount of the compound which is the lowest dose effective to produce a therapeutic effect. Such an effective dose will generally depend upon the factors described above. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

If desired, the effective daily dose of the active compound may be administered as two, three, four, five, six or more sub-doses administered separately at appropriate intervals throughout the day, optionally, in unit dosage forms. Preferred dosing is one administration per day.

V. Particular Embodiments

In another aspect, the disclosure provides the following particular embodiments.

Embodiment 1. Use of an anionic polymer, or a pharmaceutically acceptable salt thereof, for the manufacture of a medicament for treating or preventing an amyloid-related disorder in a subject in need thereof, with the proviso that the anionic polymer is not dextran sulfate, dextran sulfate sodium, pentosan polysulfate, or pentosan polysulfate sodium.

Embodiment 2. The use of Embodiment 1, wherein the anionic polymer is an anionic heteropolymer, or a pharmaceutically acceptable salt thereof.

Embodiment 3. The use of Embodiment 2, wherein the constitutional repeating units of the anionic heteropolymer are any two or more of acrylic acid, or a salt thereof; methacrylic acid, or a salt thereof; maleic acid, or a salt thereof; fumaric acid, or a salt thereof; ethylsulphonic acid, or a salt thereof; vinylsulphonic acid, or a salt thereof; vinylsulphonic acid, or a salt thereof; styrenesulphonic acid, or a salt thereof; vinylphenylsulphuric acid, or a salt thereof; 2-methacryloyloxyethane sulphonic acid, or a salt thereof;

3-methacryloyloxy-2-hydroxypropanesulphonic acid, or a salt thereof; 3-methacryl amido-3-methylbutanoic acid, or a salt thereof; acrylamidomethylpropanesulfonic acid, or a salt thereof; vinylphosphoric acid, or a salt thereof; 4-vinylbenzoic acid, or a salt thereof; 3-vinyl oxypropane-1-sulphonic acid, or a salt thereof; or N-vinylsuccinimidic acid, or a salt thereof.

Embodiment 4. The use of Embodiment 1, wherein the anionic polymer is an anionic homopolymer, or a pharmaceutically acceptable salt thereof.

Embodiment 5. The use of Embodiment 4, wherein the constitutional repeating units of the anionic homopolymer are any one of acrylic acid, or a salt thereof; methacrylic acid, or a salt thereof; maleic acid, or a salt thereof; fumaric acid, or a salt thereof; ethylsulphonic acid, or a salt thereof; vinylsulphonic acid, or a salt thereof; vinylsulphonic acid, or a salt thereof; styrenesulphonic acid, or a salt thereof; vinylphenylsulphuric acid, or a salt thereof; 2-methacryloyloxyethane sulphonic acid, or a salt thereof; 3-methacryloyloxy-2-hydroxypropanesulphonic acid, or a salt thereof; 3-methacryl amido-3-methylbutanoic acid, or a salt thereof; acrylamidomethylpropanesulfonic acid, or a salt thereof; vinylphosphoric acid, or a salt thereof; 4-vinylbenzoic acid, or a salt thereof; 3-vinyl oxypropane-1-sulphonic acid, or a salt thereof; or N-vinylsuccinimidic acid, or a salt thereof.

Embodiment 6. The use of Embodiment 1, wherein the anionic polymer is selected from the group consisting of polystyrene sulfonic acid, or the sodium salt thereof; poly (styrene-co-maleic acid) partial isobutyl ester, or the sodium salt thereof; poly (2-acrylamido-2-methyl-1-propanesulfonic acid), or the sodium salt thereof; poly (styrene-alt-maleic acid), or the sodium salt thereof; and poly(4-styrenesulfonic acid-co-maleic acid), or the sodium salt thereof.

Embodiment 7. The use of any one of Embodiments 1-6, wherein anionic polymer comprises about 100 to about 20,000 constitutional repeating units.

Embodiment 8. The use of Embodiment 7, wherein anionic polymer comprises about 100 to about 10,000 constitutional repeating units.

Embodiment 9. The use of any one of Embodiments 1-8, wherein the amyloid-related disorder is Alzheimer's disease, senile systemic amyloidosis, cerebral amyloid angiopathy, Parkinson's disease, rheumatoid arthritis, Huntington's disease, medullary thyroid cancer, cardiac arrhythmia (dysrhythmia), atherosclerosis, polactinoma, familial amyloid polyneuropathy, heredity non-neuropathic systemic amyloidosis (Ostertag type), Beta 2 microglobulin amyloidosis, Finnish type amyloidosis, lattice dystrophy, cerebral amyloid angiopathy (congophilic angiopathy), systemic AL amyloidosis, sporadic inclusion body myositis, phaeochromocytoma, osteomyelitis, multiple myeloma, type II diabetes, scrapie, bovine spongiform encephalitis, Creutzfeldt Jakob disease, Gerstmann Sträussler Scheinker syndrome, fatal familial insomnia, kuru, a prion protein related disorder, memory impairment, localized amyloidosis, or systemic amyloidosis.

Embodiment 10. The use of Embodiment 9, wherein the amyloid-related disorder is Alzheimer's disease.

Embodiment 11. The use of any one of Embodiments 1-10, further comprising administering to the subject a therapeutically effective amount of a second therapeutic agent to the subject selected from the group consisting of a cholinesterase inhibitor, an antioxidant Ginkobiloba extract, a nonsteroidal anti-inflammatory agent, a non-specific NMDA antagonist, carbidopa/levodopa, a dopamine agonist, a COMT inhibitor, an anticholinergic, a MAO inhibitor, a biguanide, a glucosidase inhibitor, insulin, a meglitinide, a sulfonylurea, a biguanide/glyburide combination, a thiozolidinedione, a PPAR-alpha agonist, a PPAR-gamma agonist, a PPAR alpha/gamma dual agonist, a SGLT2 inhibitor, an inhibitor of fatty acid binding protein (aP2), a glucagon-like peptide-1 (GLP-1), and a dipeptidyl peptidase IV (DP4) inhibitor.

Embodiment 12. The use of any one of Embodiments 1-11, wherein the subject is a human.

Embodiment 13. The use of any one of Embodiments 1-12, wherein the anionic polymer, or a pharmaceutically acceptable salt thereof, is administered to the subject as a pharmaceutical composition comprising one or more pharmaceutically acceptable carriers.

Embodiment 14. The use of Embodiment 13, wherein the pharmaceutical composition comprises about 0.1% to about 1% w/v hydroxypropyl methylcellulose and about 0.05% to about 0.5% w/v polysorbate 80.

Embodiment 15. The use of Embodiment 14, wherein the pharmaceutical composition comprises about 0.5% w/v hydroxypropyl methylcellulose and about 0.1% w/v polysorbate 80.

In another aspect, the disclosure provides the following particular embodiments.

Embodiment I. An anionic polymer, or a pharmaceutically acceptable salt thereof, for use in treating or preventing an amyloid-related disorder in a subject in need thereof, with the proviso that the anionic polymer is not dextran sulfate, dextran sulfate sodium, pentosan polysulfate, or pentosan polysulfate sodium.

Embodiment II. The anionic polymer, or a pharmaceutically acceptable salt thereof, for use of Embodiment I, wherein the anionic polymer is an anionic heteropolymer, or a pharmaceutically acceptable salt thereof.

Embodiment III. The anionic polymer, or a pharmaceutically acceptable salt thereof, for use of Embodiment II, wherein the constitutional repeating units of the anionic heteropolymer are any two or more of acrylic acid, or a salt thereof; methacrylic acid, or a salt thereof; maleic acid, or a salt thereof; fumaric acid, or a salt thereof; ethylsulphonic acid, or a salt thereof; vinylsulphonic acid, or a salt thereof; vinylsulphonic acid, or a salt thereof; styrenesulphonic acid, or a salt thereof; vinylphenylsulphuric acid, or a salt thereof; 2-methacryloyloxyethane sulphonic acid, or a salt thereof; 3-methacryloyloxy-2-hydroxypropanesulphonic acid, or a salt thereof; 3-methacryl amido-3-methylbutanoic acid, or a salt thereof; acrylamidomethylpropanesulfonic acid, or a salt thereof; vinylphosphoric acid, or a salt thereof; 4-vinylbenzoic acid, or a salt thereof; 3-vinyl oxypropane-1-sulphonic acid, or a salt thereof; or N-vinylsuccinimidic acid, or a salt thereof.

Embodiment IV. The anionic polymer, or a pharmaceutically acceptable salt thereof, for use of Embodiment I, wherein the anionic polymer is an anionic homopolymer, or a pharmaceutically acceptable salt thereof.

Embodiment V. The anionic polymer, or a pharmaceutically acceptable salt thereof, for use of Embodiment IV, wherein the constitutional repeating units of the anionic homopolymer are any one of acrylic acid, or a salt thereof; methacrylic acid, or a salt thereof; maleic acid, or a salt thereof; fumaric acid, or a salt thereof; ethylsulphonic acid, or a salt thereof; vinylsulphonic acid, or a salt thereof; vinylsulphonic acid, or a salt thereof; styrenesulphonic acid, or a salt thereof; vinylphenylsulphuric acid, or a salt thereof; 2-methacryloyloxyethane sulphonic acid, or a salt thereof; 3-methacryloyloxy-2-hydroxypropanesulphonic acid, or a salt thereof; 3-methacryl amido-3-methylbutanoic acid, or a salt thereof; acrylamidomethylpropanesulfonic acid, or a salt thereof; vinylphosphoric acid, or a salt thereof; 4-vinylbenzoic acid, or a salt thereof; 3-vinyl oxypropane-1-sulphonic acid, or a salt thereof; or N-vinylsuccinimidic acid, or a salt thereof.

Embodiment VI. The anionic polymer, or a pharmaceutically acceptable salt thereof, for use of Embodiment I, wherein the anionic polymer is selected from the group consisting of polystyrene sulfonic acid, or the sodium salt thereof; poly (styrene-co-maleic acid) partial isobutyl ester, or the sodium salt thereof; poly (2-acrylamido-2-methyl-1-propanesulfonic acid), or the sodium salt thereof; poly (styrene-alt-maleic acid), or the sodium salt thereof; and poly(4-styrenesulfonic acid-co-maleic acid), or the sodium salt thereof.

Embodiment VII. The anionic polymer, or a pharmaceutically acceptable salt thereof, for use of any one of Embodiments I-VI, wherein anionic polymer comprises about 100 to about 20,000 constitutional repeating units.

Embodiment VIII. The anionic polymer, or a pharmaceutically acceptable salt thereof, for use of Embodiment VII, wherein anionic polymer comprises about 100 to about 10,000 constitutional repeating units.

Embodiment IX. The anionic polymer, or a pharmaceutically acceptable salt thereof, for use of any one of Embodiments I-VIII, wherein the amyloid-related disorder is Alzheimer's disease, senile systemic amyloidosis, cerebral amyloid angiopathy, Parkinson's disease, rheumatoid arthritis, Huntington's disease, medullary thyroid cancer, cardiac arrhythmia (dysrhythmia), atherosclerosis, polactinoma, familial amyloid polyneuropathy, heredity non-neuropathic systemic amyloidosis (Ostertag type), Beta 2 microglobulin amyloidosis, Finnish type amyloidosis, lattice dystrophy, cerebral amyloid angiopathy (congophilic angiopathy), systemic AL amyloidosis, sporadic inclusion body myositis, phaeochromocytoma, osteomyelitis, multiple myeloma, type II diabetes, scrapie, bovine spongiform encephalitis, Creutzfeldt Jakob disease, Gerstmann Sträussler Scheinker syndrome, fatal familial insomnia, kuru, a prion protein related disorder, memory impairment, localized amyloidosis, or systemic amyloidosis.

Embodiment X. The anionic polymer, or a pharmaceutically acceptable salt thereof, for use of Embodiment IX, wherein the amyloid-related disorder is Alzheimer's disease.

Embodiment XI. The anionic polymer, or a pharmaceutically acceptable salt thereof, for use of any one of Embodiments I-X, further comprising administering to the subject a therapeutically effective amount of a second therapeutic agent to the subject selected from the group consisting of a cholinesterase inhibitor, an antioxidant Ginkobiloba extract, a nonsteroidal anti-inflammatory agent, a non-specific NMDA antagonist, carbidopa/levodopa, a dopamine agonist, a COMT inhibitor, an anticholinergic, a MAO inhibitor, a biguanide, a glucosidase inhibitor, insulin, a meglitinide, a sulfonylurea, a biguanide/glyburide combination, a thiozolidinedione, a PPAR-alpha agonist, a PPAR-gamma agonist, a PPAR alpha/gamma dual agonist, a SGLT2 inhibitor, an inhibitor of fatty acid binding protein (aP2), a glucagon-like peptide-1 (GLP-1), and a dipeptidyl peptidase IV (DP4) inhibitor.

Embodiment XII. The anionic polymer, or a pharmaceutically acceptable salt thereof, for use of any one of Embodiments I-XI, wherein the subject is a human.

Embodiment XIII. The anionic polymer, or a pharmaceutically acceptable salt thereof, for use of any one of Embodiments I-XII, wherein the anionic polymer, or a pharmaceutically acceptable salt thereof, is administered to the subject as a pharmaceutical composition comprising one or more pharmaceutically acceptable carriers.

Embodiment XIV. The anionic polymer, or a pharmaceutically acceptable salt thereof, for use of Embodiment XIII, wherein the pharmaceutical composition comprises about 0.1% to about 1% w/v hydroxypropyl methylcellulose and about 0.05% to about 0.5% w/v polysorbate 80.

Embodiment XV. The anionic polymer, or a pharmaceutically acceptable salt thereof, for use of Embodiment XIV, wherein the pharmaceutical composition comprises about 0.5% w/v hydroxypropyl methylcellulose and about 0.1% w/v polysorbate 80.

In another aspect, the disclosure provides the following particular embodiments.

Embodiment 1. A therapeutic or prophylactic agent for an amyloid-related disorder, which comprises an anionic polymer, or a pharmaceutically acceptable salt thereof.

Embodiment 2. The therapeutic or prophylactic agent of Embodiment 1, wherein the anionic polymer is an anionic heteropolymer, or a pharmaceutically acceptable salt thereof.

Embodiment 3. The therapeutic or prophylactic agent of Embodiment 2, wherein the constitutional repeating units of the anionic heteropolymer are any two or more of acrylic acid, or a salt thereof; methacrylic acid, or a salt thereof; maleic acid, or a salt thereof; fumaric acid, or a salt thereof; ethylsulphonic acid, or a salt thereof; vinylsulphonic acid, or a salt thereof; vinylsulphonic acid, or a salt thereof; styrenesulphonic acid, or a salt thereof; vinylphenylsulphuric acid, or a salt thereof; 2-methacryloyloxyethane sulphonic acid, or a salt thereof; 3-methacryloyloxy-2-hydroxypropanesulphonic acid, or a salt thereof; 3-methacryl amido-3-methylbutanoic acid, or a salt thereof; acrylamidomethylpropanesulfonic acid, or a salt thereof; vinylphosphoric acid, or a salt thereof; 4-vinylbenzoic acid, or a salt thereof; 3-vinyl oxypropane-1-sulphonic acid, or a salt thereof; or N-vinylsuccinimidic acid, or a salt thereof.

Embodiment 4. The therapeutic or prophylactic agent of Embodiment 1, wherein the anionic polymer is an anionic homopolymer, or a pharmaceutically acceptable salt thereof.

Embodiment 5. The therapeutic or prophylactic agent of Embodiment 4, wherein the constitutional repeating units of the anionic homopolymer are any one of acrylic acid, or a salt thereof; methacrylic acid, or a salt thereof; maleic acid, or a salt thereof; fumaric acid, or a salt thereof; ethylsulphonic acid, or a salt thereof; vinylsulphonic acid, or a salt thereof; vinylsulphonic acid, or a salt thereof; styrenesulphonic acid, or a salt thereof; vinylphenylsulphuric acid, or a salt thereof; 2-methacryloyloxyethane sulphonic acid, or a salt thereof; 3-methacryloyloxy-2-hydroxypropanesulphonic acid, or a salt thereof; 3-methacryl amido-3-methylbutanoic acid, or a salt thereof; acrylamidomethylpropanesulfonic acid, or a salt thereof; vinylphosphoric acid, or a salt thereof; 4-vinylbenzoic acid, or a salt thereof; 3-vinyl oxypropane-1-sulphonic acid, or a salt thereof; or N-vinylsuccinimidic acid, or a salt thereof.

Embodiment 6. The therapeutic or prophylactic agent of Embodiment 1, wherein the anionic polymer is selected from the group consisting of polystyrene sulfonic acid, or the sodium salt thereof; poly (styrene-co-maleic acid) partial isobutyl ester, or the sodium salt thereof; poly (2-acrylamido-2-methyl-1-propanesulfonic acid), or the sodium salt thereof; poly (styrene-alt-maleic acid), or the sodium salt thereof; and poly(4-styrenesulfonic acid-co-maleic acid), or the sodium salt thereof.

Embodiment 7. The therapeutic or prophylactic agent of any one of Embodiments 1-6, wherein anionic polymer comprises about 100 to about 20,000 constitutional repeating units.

Embodiment 8. The therapeutic or prophylactic agent of Embodiment 7, wherein anionic polymer comprises about 100 to about 10,000 constitutional repeating units.

Embodiment 9. The therapeutic or prophylactic agent of any one of Embodiments 1-8, wherein the amyloid-related disorder is Alzheimer's disease, senile systemic amyloidosis, cerebral amyloid angiopathy, Parkinson's disease, rheumatoid arthritis, Huntington's disease, medullary thyroid cancer, cardiac arrhythmia (dysrhythmia), atherosclerosis, polactinoma, familial amyloid polyneuropathy, heredity non-neuropathic systemic amyloidosis (Ostertag type), Beta 2 microglobulin amyloidosis, Finnish type amyloidosis, lattice dystrophy, cerebral amyloid angiopathy (congophilic angiopathy), systemic AL amyloidosis, sporadic inclusion body myositis, phaeochromocytoma, osteomyelitis, multiple myeloma, type II diabetes, scrapie, bovine spongiform encephalitis, Creutzfeldt Jakob disease, Gerstmann Sträussler Scheinker syndrome, fatal familial insomnia, kuru, a prion protein related disorder, memory impairment, localized amyloidosis, or systemic amyloidosis.

Embodiment 10. The therapeutic or prophylactic agent of Embodiment 9, wherein the amyloid-related disorder is Alzheimer's disease.

Embodiment 11. The therapeutic or prophylactic agent of any one of Embodiments 1-10, further comprising administering to the subject a therapeutically effective amount of a second therapeutic agent to the subject selected from the group consisting of a cholinesterase inhibitor, an antioxidant Ginkobiloba extract, a nonsteroidal anti-inflammatory agent, a non-specific NMDA antagonist, carbidopa/levodopa, a dopamine agonist, a COMT inhibitor, an anticholinergic, a MAO inhibitor, a biguanide, a glucosidase inhibitor, insulin, a meglitinide, a sulfonylurea, a biguanide/glyburide combination, a thiozolidinedione, a PPAR-alpha agonist, a PPAR-gamma agonist, a PPAR alpha/gamma dual agonist, a SGLT2 inhibitor, an inhibitor of fatty acid binding protein (aP2), a glucagon-like peptide-1 (GLP-1), and a dipeptidyl peptidase IV (DP4) inhibitor.

Embodiment 12. The therapeutic or prophylactic agent of any one of Embodiments 1-11, wherein the subject is a human.

Embodiment 13. The therapeutic or prophylactic agent of any one of Embodiments 1-12, wherein the anionic polymer, or a pharmaceutically acceptable salt thereof, is administered to the subject as a pharmaceutical composition comprising one or more pharmaceutically acceptable carriers.

Embodiment 14. The therapeutic or prophylactic agent of Embodiment 13, wherein the pharmaceutical composition comprises about 0.1% to about 1% w/v hydroxypropyl methylcellulose and about 0.05% to about 0.5% w/v polysorbate 80.

Embodiment 15. The therapeutic or prophylactic agent of Embodiment 14, wherein the pharmaceutical composition comprises about 0.5% w/v hydroxypropyl methylcellulose and about 0.1% w/v polysorbate 80.

In another aspect, the disclosure provides the following particular embodiments.

Embodiment I. A pharmaceutical composition comprising an anionic polymer, or a pharmaceutically acceptable salt thereof, and one or more pharmaceutically acceptable carriers for use in treating or preventing an amyloid-related disorder in a subject in need thereof.

Embodiment II. The pharmaceutical composition of Embodiment I, wherein the anionic polymer is an anionic heteropolymer, or a pharmaceutically acceptable salt thereof.

Embodiment III. The pharmaceutical composition of Embodiment II, wherein the constitutional repeating units of the anionic heteropolymer are any two or more of acrylic acid, or a salt thereof; methacrylic acid, or a salt thereof; maleic acid, or a salt thereof; fumaric acid, or a salt thereof; ethylsulphonic acid, or a salt thereof; vinylsulphonic acid, or a salt thereof; vinylsulphonic acid, or a salt thereof; styrenesulphonic acid, or a salt thereof; vinylphenylsulphuric acid, or a salt thereof; 2-methacryloyloxyethane sulphonic acid, or a salt thereof; 3-methacryloyloxy-2-hydroxypropanesulphonic acid, or a salt thereof; 3-methacryl amido-3-methylbutanoic acid, or a salt thereof; acrylamidomethylpropanesulfonic acid, or a salt thereof; vinylphosphoric acid, or a salt thereof; 4-vinylbenzoic acid, or a salt thereof; 3-vinyl oxypropane-1-sulphonic acid, or a salt thereof; or N-vinylsuccinimidic acid, or a salt thereof.

Embodiment IV. The pharmaceutical composition of Embodiment I, wherein the anionic polymer is an anionic homopolymer, or a pharmaceutically acceptable salt thereof.

Embodiment V. The pharmaceutical composition of Embodiment IV, wherein the constitutional repeating units of the anionic homopolymer are any one of acrylic acid, or a salt thereof; methacrylic acid, or a salt thereof; maleic acid, or a salt thereof; fumaric acid, or a salt thereof; ethylsulphonic acid, or a salt thereof; vinylsulphonic acid, or a salt thereof; vinylsulphonic acid, or a salt thereof; styrenesulphonic acid, or a salt thereof; vinylphenylsulphuric acid, or a salt thereof; 2-methacryloyloxyethane sulphonic acid, or a salt thereof; 3-methacryloyloxy-2-hydroxypropanesulphonic acid, or a salt thereof; 3-methacryl amido-3-methylbutanoic acid, or a salt thereof; acrylamidomethylpropanesulfonic acid, or a salt thereof; vinylphosphoric acid, or a salt thereof; 4-vinylbenzoic acid, or a salt thereof; 3-vinyl oxypropane-1-sulphonic acid, or a salt thereof; or N-vinylsuccinimidic acid, or a salt thereof.

Embodiment VI. The pharmaceutical composition of Embodiment I, wherein the anionic polymer is selected from the group consisting of polystyrene sulfonic acid, or the sodium salt thereof; poly (styrene-co-maleic acid) partial isobutyl ester, or the sodium salt thereof; poly (2-acrylamido-2-methyl-1-propanesulfonic acid), or the sodium salt thereof; poly (styrene-alt-maleic acid), or the sodium salt thereof; and poly(4-styrenesulfonic acid-co-maleic acid), or the sodium salt thereof.

Embodiment VII. The pharmaceutical composition of any one of Embodiments I-VI, wherein anionic polymer comprises about 100 to about 20,000 constitutional repeating units.

Embodiment VIII. The pharmaceutical composition of Embodiment VII, wherein anionic polymer comprises about 100 to about 10,000 constitutional repeating units.

Embodiment IX. The pharmaceutical composition of any one of Embodiments I-VIII, wherein the amyloid-related disorder is Alzheimer's disease, senile systemic amyloidosis, cerebral amyloid angiopathy, Parkinson's disease, rheumatoid arthritis, Huntington's disease, medullary thyroid cancer, cardiac arrhythmia (dysrhythmia), atherosclerosis, polactinoma, familial amyloid polyneuropathy, heredity non-neuropathic systemic amyloidosis (Ostertag type), Beta 2 microglobulin amyloidosis, Finnish type amyloidosis, lattice dystrophy, cerebral amyloid angiopathy (congophilic angiopathy), systemic AL amyloidosis, sporadic inclusion body myositis, phaeochromocytoma, osteomyelitis, multiple myeloma, type II diabetes, scrapie, bovine spongiform encephalitis, Creutzfeldt Jakob disease, Gerstmann Sträussler Scheinker syndrome, fatal familial insomnia, kuru, a prion protein related disorder, memory impairment, localized amyloidosis, or systemic amyloidosis.

Embodiment X. The pharmaceutical composition of Embodiment IX, wherein the amyloid-related disorder is Alzheimer's disease.

Embodiment XI. The pharmaceutical composition of Embodiments I-X, further comprising administering to the subject a therapeutically effective amount of a second therapeutic agent to the subject selected from the group consisting of a cholinesterase inhibitor, an antioxidant Ginkobiloba extract, a nonsteroidal anti-inflammatory agent, a non-specific NMDA antagonist, carbidopa/levodopa, a dopamine agonist, a COMT inhibitor, an anticholinergic, a MAO inhibitor, a biguanide, a glucosidase inhibitor, insulin, a meglitinide, a sulfonylurea, a biguanide/glyburide combination, a thiozolidinedione, a PPAR-alpha agonist, a PPAR-gamma agonist, a PPAR alpha/gamma dual agonist, a SGLT2 inhibitor, an inhibitor of fatty acid binding protein (aP2), a glucagon-like peptide-1 (GLP-1), and a dipeptidyl peptidase IV (DP4) inhibitor.

Embodiment XII. The pharmaceutical composition of any one of Embodiments I-XI, wherein the subject is a human.

Embodiment XIII. The pharmaceutical composition of any one of Embodiments I-XII, comprising about 0.1% to about 1% w/v hydroxypropyl methylcellulose and about 0.05% to about 0.5% w/v polysorbate 80.

Embodiment XIV. The pharmaceutical composition of Embodiment XIII, comprising about 0.5% w/v hydroxypropyl methylcellulose and about 0.1% w/v polysorbate 80.

EXAMPLES

The disclosure now being generally described, will be more readily understood by reference to the following examples, which are included merely for purposes of illustration of certain aspects and embodiments of the present disclosure, and are not intended to limit the disclosure.

General Experimental and Method Details

Transgenic and Control Mouse Strains

Mice were cared for by the Yale Animal Resource Center and all experiments were approved by Yale's Institutional Animal Care and Use Committee and performed in accordance with the American Association for Accreditation of Laboratory Animal Care (AAALAC). Wild type and APPswe/PS1ΔE9 mice (APP/PS1) (Jankowsky et al., 2004) were purchased from Jackson Laboratory and maintained on a C57/B16J background as described previously (Gimbel et al., 2010; Um et al., 2012, 2013). All experiments were conducted in a blinded fashion with respect to genotype and treatment, and groups were matched for age and sex, and groups contained 45-55% of each sex.

Aβo Preparation

Biotinylated and unlabeled synthetic Aβ1-42 peptide were obtained as lyophilized powder from The ERI Amyloid Laboratory, LLC (Oxford, CT). Preparation and characterization of Aβ1-42 oligomers (Aβo) have been described previously (Um et al., 2012). AB monomer was dissolved at 10 mg/ml in HFIP and boiled in water bath 1 hr at 70 C, then cooled on ice, transferred to 2 ml microfuge and tubes spun 7 min at 12,000×g. Avoiding pellet, 50 µl (0.5 mg) was aliquoted in a 1.6 ml microfuge tube and allowed to evaporate completely in chemical hood (24 hrs), followed by 1+hr in speed vac. An observable clear film surrounded the inside tip of the tube. Closed tubes were stored at RT for later oligomer preparation. To prepare oligomers, add 40 µl DMSO to tube, allow to stand 20 min with occasional flicking/trituration to suspend peptide, wiping down tube sides to insure no un-dissolved peptide remains. Aliquot 20 µl/1.6 ml microfuge tube. Add 1 ml phenol red-free F12 (Atlanta Biologicals cat #M15350) to tubes for 0.25 mg/ml final conc. Let stand O/N at RT. Spin 15 min at 14000 rpm—there was usually no pellet; a large pellet indicates an unsuccessful prep. Aliquots can be frozen for later use. Binding assays showed consistent results over at least 72 hrs post F12 addition. Concentrations of Aβo are expressed in monomer equivalents, with 1 µM total Aβ1-42 peptide corresponding to approximately 10 nM oligomeric species (Lauren et al., 2009).

Cell-based Screen for small molecule inhibitors of Aβo/PrP$^C$ interaction

CV1 cells stably transfected with rat PrP were plated in 96 well tissue culture plates (Corning, 354461) 24 hr prior to application of small molecule library components dissolved at 10 mM in DMSO (10 µM final concentration) for 1 hr prior to addition of biotinylated Aβo (1 µM final concentration). Wells were fixed in 4% formaldehyde, washed twice with PBS, blocked 1 hr in PBS containing 5% goat serum (Gibco, 16210-064). 50 µl 1:1000 Eu-labeled streptavidin (PerkinElmer, 1244-360) in DELFIA assay buffer (PerkinElmer Life Sciences) was added per well for 30 min. After washing five times in PBST, 50 µl of DELFIA Enhancement Solution (PerkinElmer Life Sciences) was applied to each well, and time-resolved europium fluorescence was measured using a Victor 3 plate reader (PerkinElmer Life Sciences). Libraries screened were Enzo FDA Approved Drugs Library (Enzo), Microsource Pharm 1600 (Microsource) and Yale Small Molecule Discovery Center compound collection.

Immunocytochemistry

COS-7 cells were maintained in DMEM supplemented with 10% fetal bovine serum and 1% penicillin/streptomycin. COS-7 cells transfected 2 days earlier with PrP$^C$ expression vector were pre-incubated with inhibitor in F12 media at 22° C. for 30 min. Biotin-Aβ42 oligomers were added to a concentration of 500 nM monomer equivalent for 2 h. Cells were washed twice with PBS, fixed 25 min with 4% formaldehyde in PBS, washed twice with PBS, blocked 1 hr with 5% goat serum in PBS, incubated in 0.1% 488-streptavidin (Life technologies, S11223) in PBS 1 hr, washed twice and visualized on an ImageExpress Micro (Molecular Devices). Images were analyzed using Image J.

Size-Exclusion Chromatography (SEC)

Aged ceftazidime (as 14 day reconstituted Fortaz) was separated on a Superdex 75 10/300 GL gel filtration column (GE Healthcare Bio-Sciences) using AKTA purifier FPLC system (GE Healthcare). 200 µl of sample was injected at a flow rate of 0.75 ml/min. PBS, pH 7.4, was used as a mobile phase. Fractions of 0.5 ml were continuously collected throughout the run and analyzed for PLISA activity or selected for Z quantitation.

Z Concentration Measurement

The SEC fraction of aged Fortaz corresponding to 15 kDa was collected, exchanged into water through extensive washes with a 3 kilodalton filter (Amicon, UFC500396), and desiccated by speed vac. Weighed material (a light brown powder) was resolubilized in a measured volume of PBS and read for absorbance at 280 nm by spectrophotometry, enabling measurement of molarity in solution.

Anion-Exchange Chromatography

Aged ceftazidime (as 14 day reconstituted Fortaz) was separated on an XK 50/20 column (GE Healthcare Life Sciences) packed with Q Sepaharose Fast Flow (GE Healthcare, 17-0510-01) with a 0.5-2.0 M NaCl gradient. Fractions eluting at 100-120 millisiemens were used as Z.

Biolayer Interferometry

Figure 6:
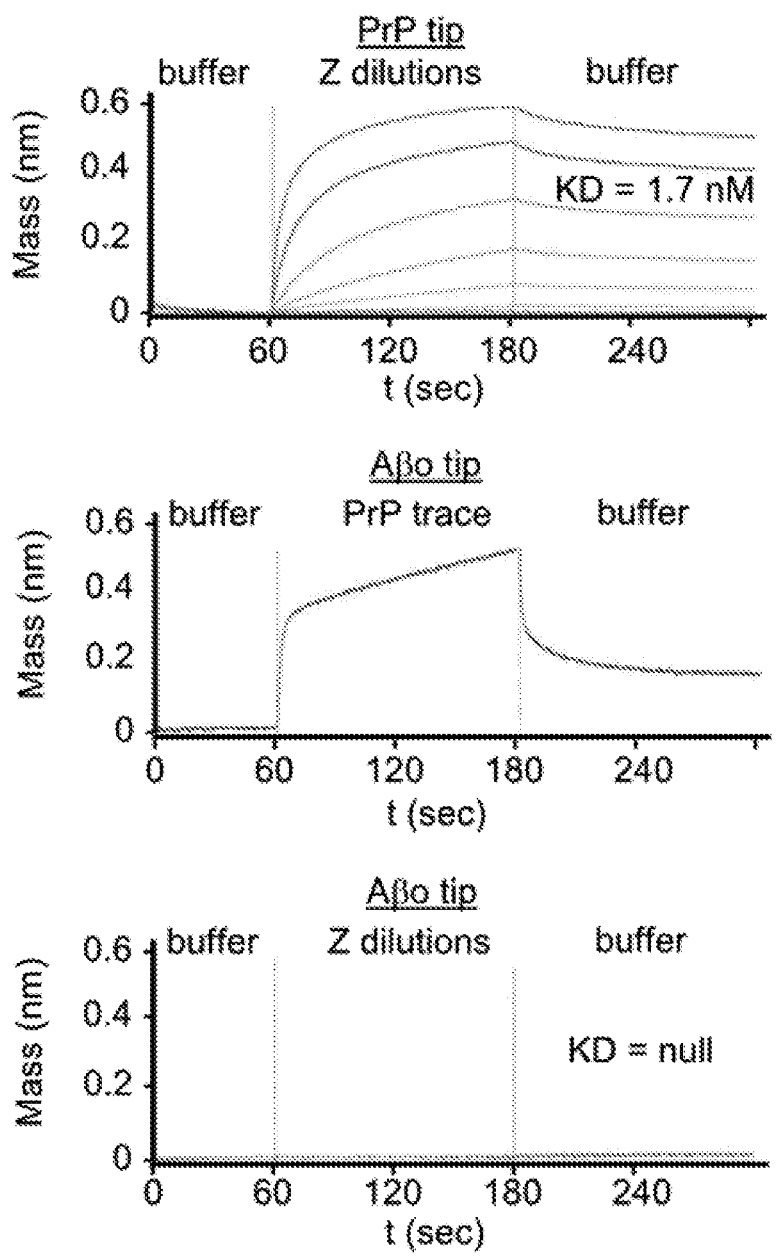
FIG. 6 is three line graphs showing biolayer interferometric association (60-180 sec) and dissociation (180-300 sec) traces of 10-20 kDa Z with $PrP^C$-coated sensor in four-fold dilution steps from 1 μM top concentration, indicating a dissociation constant of 1.7 nM (top graph). Aβo-coated sensor detects soluble full length $PrP^C$ interaction but not compound Z (middle and bottom graphs, respectively).
Figure 7:
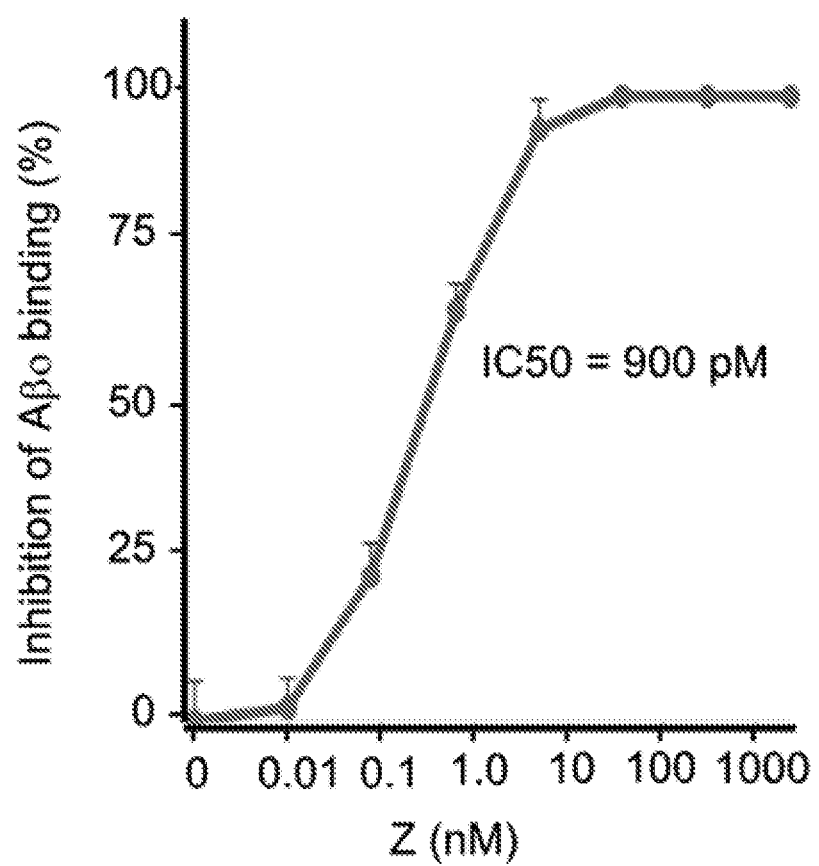
FIG. 7 is a line graph showing PLISA measurement of 10-20 kDa Z Aβo/$PrP^C$ inhibitory activity, indicating an $IC_{50}$ of 910 pM. Data are mean+/−SEM, n=3 replicates per sample.
Figure 8:
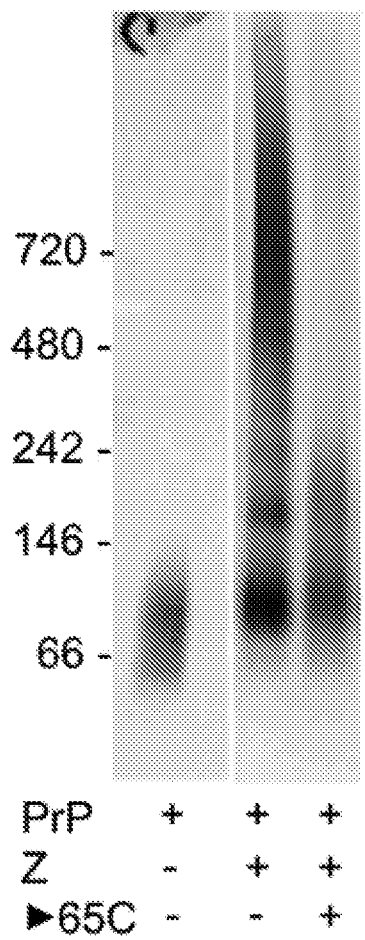
FIG. 8 is an illustration showing $PrP^C$ immunoblot of non-denaturing gel-shift assay of full length $PrP^C$ incubated with 10-40 kDa Z. Laddering indicates multiple $PrP^C$ molecules bound per Z molecule. Incubation at 65 C after co-incubation shows reversible association of Z and $PrP^C$.

Biotinylated Aβo or full-length human $PrP^C$ biotinylated by incubation in 2-fold molar excess biotin-NHS (Thermo Scientific, 21329) 2 hr in PBS at RT were coated onto streptavidin Biosensors (ForteBio, 18-5019) and exposed to dilution series of solutes as described in FIGS. 2A, 6A, 6B in PBS with 0.05% Tween 20 (Sigma, P7949) and 0.1% BSA. Association curves were detected and analyzed using an Octet biolayer interferometer (ForteBio).

Blue Native PAGE Shift Assay

Recombinant human $PrP^C$ (1 μM) was incubated in the presence or absence of 2 μM Z for 10 min in 0.25×PBS at room temperature. Following the incubation, the samples were loaded on 4-16% NOVEX Bis-Tris gel (ThermoFisher) and separated according to manufacturer's recommendations. To demonstrate the requirement of native $PrP^C$ structure for complexation with compound Z, some samples were heated in 65 C heatblock for 10 minutes prior to BN-PAGE separation to denature the protein. Following the BN-PAGE, the gels were transferred onto PVDF membranes using iBlot semi-dry transfer (ThermoFisher), the membranes were dried and the excess of Coomassie dye was removed by washing the membrane in methanol three times for 5 min to avoid interference with subsequent immunoblotting. The membranes were then washed 3× with water, blocked using fluorescent western blot blocking buffer (Rockland) and immunoblotted with 1:500 SAF-32 mouse anti-$PrP^C$ antibody (Cayman Chemical) in TBS-T followed by 800CW-conjugated donkey anti-mouse secondary antibody (LiCor). Immunoblots were imaged using LiCor Odyssey near-infrared scanner.

Assay for Aβo Binding to Immobilized $PrP^C$ (PLISA)

MaxiSorp 384 well white microplates (ThermoFisher Scientific, 460372) were coated overnight with 20 μl/well of 250 nM human full length PrP in 30 mM $Na_2CO_3$, 80 mM $NaHCO_3$, pH 9.6, at 4° C. After washing two times with PBST (PBS, 0.05% Tween 20), the plates were blocked with 100 μl/well protein-free T20 PBS blocking buffer (Pierce, 37573) for 1 hr at room temperature. After washing three times with PBST, 20 μl of samples diluted in PBST (PBS, 0.05% Tween 20) were applied to microplates in triplicate and incubated 1 hr at RT. 20 μl of synthetic biotinylated Aβo in PBSTB (5 nM monomer equivalent) was added per well for 2 h. Plates were then washed four times with PBST and incubated 1 hr with 20 μl 1:1000 Eu-labeled streptavidin (PerkinElmer, 1244-360) in DELFIA assay buffer (PerkinElmer Life Sciences). Finally, after washing five times in PBST, 20 μl of DELFIA Enhancement Solution (PerkinElmer Life Sciences) was applied to each well, and time-resolved europium fluorescence was measured using a Victor 3 plate reader (PerkinElmer Life Sciences).

Biochemical Small Molecule Screen

PLISA was used to screen 52,000 unique compounds not included in the initial cell-based screen. Libraries screened were MicroSource GenPlus (Microsource), Yale compound collection, and ChemDiv Diversity Library (ChemDiv). Small molecule library components are stored dissolved at 10 mM in DMSO (10 μM final concentration) and added in singlet to PrP-coated wells of a 384-well plate containing PBST for a final concentration of 10 μM. After 30 min, PBST containing biotinylated Aβo was added for a final Aβo concentration of 5 nM, incubated @ RT 2 hr and developed per PLISA protocol. Hits exceeding 50% signal inhibition were followed up with validation using fresh purified material.

Z-Binding PrP-Epitope Mapping

A MaxiSorp 384 well white microplate (ThermoFisher Scientific, 460372) was coated overnight with 20 μl/well of 250 nM human full length $PrP^C$ in 30 mM $Na_2CO_3$, 80 mM $NaHCO_3$, pH 9.6, at 4° C. After washing two times with PBST (PBS, 0.05% Tween 20), the plates were blocked with 100 μl/well protein-free T20 PBS blocking buffer (Pierce, 37573) for 1 hr at 23° C. After washing three times with PBST, 20 μl of anti-PrP antibodies (8B4, Santa Cruz Biotech, sc-47729; 5058, Millipore Sigma, AB5058; 8G8, Cayman chemical, 189760; 6D11, Covance, SIG-399810; Pri 308, Cayman Chemical, 189750; 8H4, abcam, ab61409; SAF70, Cayman Chemical, 189770) diluted 1:50 in PBST (PBS, 0.05% Tween 20) were applied to microplate wells in triplicate and incubated 1 hr at RT. 20 μl of 50 nM Z biotinylated by incubation in 10-fold molar excess biotin-NHS (Thermo Scientific, 21329) 2 hr in PBS at RT was added per well for 2 h. Plates were then washed four times with PBST and incubated 1 hr with 20 μl 1:1000 Eu-labeled streptavidin (PerkinElmer, 1244-360) in DELFIA assay buffer (PerkinElmer Life Sciences). Finally, after washing three times in PBST, 20 μl of DELFIA Enhancement Solution (PerkinElmer Life Sciences) was applied to each well, and time-resolved europium fluorescence was measured using a Victor 3V plate reader (PerkinElmer Life Sciences).

$PrP^{Sc}$ Propagation Assay

Chronically $PrP^{Sc}$-infected ScN2a cells were cultured in Delbucco's Modified Eagle Medium (DMEM) with L-glutamine and 4.5 g/L glucose plus 10% fetal bovine serum (FBS) and 50 U/ml penicillin, 50 μg/ml streptomycin. 10 mM and 5 mM stock solutions of polymers Z and PSCMA, respectively, were prepared in PBS and stored at 4° C. for no longer than 1 week prior to use. Compound stock solutions or PBS alone (vehicle control) were added to cell culture medium and working concentrations obtained via serial dilution. Trypsinized ScN2a cells were split 1:10 and allowed to adhere to plates in compound-free media for 12 h, at which point medium containing the treatment compound was added. Cells were grown for 3 days to confluence with a media exchange at 36 hours. Cells were trypsinized, split 1:10 and again allowed to adhere in compound-free media for 12 h, and then returned to compound-containing medium for an additional 3 days prior to processing. Cells were lysed in ice-cold lysis buffer (10 mM Tris pH 7.5, 150 mM NaCl, 0.5% w/v sodium deoxycholate, 0.5% v/v NP-40). Lysate was centrifuged at 2,100×g for 30 s to pellet DNA. 10% of the resulting supernatant was added to an equal volume of 2×SDS-PAGE loading buffer, boiled at 95° C. for 10 min and saved as the minus proteinase K (−PK) sample. To the remaining supernatant, PK was added to a final concentration of 20 μg/ml and samples were digested shaking at 37° C. for 30 min prior to quenching with the addition of phenylmethylsulfonyl fluoride (PMSF) to a final concentration of 5 mM. PK-digested samples were centrifuged at 100,000×g for 1 hour at 4° C. and the pellet was resuspended in equal volumes of lysis buffer and 2×SDS-PAGE loading buffer prior to boiling and analysis via SDS-PAGE and Western blot. Western blotting was carried out with GE8 primary antibody at 1:2000 and HRP-conjugated sheep anti-mouse secondary antibody at 1:5000.

Immunoblots

Proteins were electrophoresed through precast 4-20% tris-glycine gels (Bio-Rad) and transferred with an iBlot™

Gel Transfer Device (Novex-Life Technologies) onto nitrocellulose membranes (Invitrogen). Membranes were blocked in blocking buffer for fluorescent western blotting (Rockland MB-070-010) for 1 hour at room temperature and incubated overnight in primary antibodies at 4° C. The following primary antibodies were used: anti-Fyn (Cell Signaling Technology 4023; 1:1,000), anti-phospho-Src (Cell Signaling Technology 2101; 1:1,000). appropriate secondary antibodies were applied for 1 hr at room temperature (Odyssey donkey anti-mouse or donkey anti-rabbit conjugated to IRDye 680 or IRDye 800, LI-COR Biosciences) and proteins were visualized with a LI-COR Odyssey infrared imaging system. Quantification of band intensities was performed within a linear range of exposure.

Neuronal Culture and Aβo Binding

Brain cortices and hippocampi were dissected from embryonic day 13 pups removed from CO2-euthanized pregnant C57/B16 mice, dissociated by incubating in 0.25% trypsin 10 min at 37 C, followed by gentle trituration in Neurobasal A medium supplemented with 2% B27, 1% Glutamax, 1% sodium pyruvate, 1% pen/strep and 0.2% FBS, filtration through a 40 μm filter and plated at 30,000 cells/well in a polylysine-coated 96 well plate. After DIV 14, wells were treated with Z or PSCMA at the specified concentrations 30 min by adding to the conditioned media, followed by addition of biotinylated Aβo for 2 h, after which cells were washed once with PBS, fixed 25 min in 4% formaldehyde in PBS, washed 3 times with PBS, blocked 1 hr in PBST with 5% goat serum, incubated overnight at 4° C. with designated antibody in PBST (SV2a, Abcam 32942, 1:250; NeuN, Millipore, mab377, 1:500 or actin, Cell Signaling Technology, 4967S, 1:500), followed by washing twice with PBS and incubating 2 hr in cognate secondary antibodies, DAPI and 0.1% 555-streptavidin (Invitrogen, S32355) in PBST, followed by washing twice in PBS and imaging with an ImagExpress (Molecular Devices). Signal was quantitated with Image J.

Imaging of Dendritic Spine Stability (Z)

Hippocampal neurons of various genotype were obtained from E17-19 mouse embryos (Um et al., 2012). After hippocampal digestion with papain (37° C.; 5% $CO_2$ for 30 min), the neurons were transfected with myristoyl-GFP expression vector by Amaxa Nucleofector. Cells were plated at 100,000 cells per well on poly-D-lysine-coated glass 8 well plates (Lab-Tek Chambered Coverslip 155411). The culture medium was Neurobasal A supplemented with 1× penicillin/streptomycin, 1 mM Na-pyruvate, 2 mM GlutaMax, and B27 supplement with weekly replenishment. After 19-23 DIV, neurons were imaged with a 100× objective on a Nikon Eclipse Ti Spinning Disk Confocal Microscope using a 488 laser. A 10 μm Z-stack at 0.1 μm intervals was obtained every 15 min over 6 hours from multiple fixed locations per 8-well dish with an automated stage. 500 nM Aβ oligomer or F12 vehicle control were added after one hour of imaging and additional images collected over 5 hours. In some conditions, 50 nM Z or drug vehicle control were added immediately before Aβ or vehicle. Spine number in consecutive images for specific dendritic segments was measured using ImageJ software without knowledge of drug or genotype. For each condition, at least 4 segments with 30 spines at time zero were assessed.

LDH Release

Cell toxicity was quantitatively assessed by the measurement of Lactose dehydrogenase (LDH) activity in the medium. LDH activity in the culture medium was measured by Cytotoxicity Detection Kit (Roche) according to manufacturer's procedure. In brief, 60 μl of supernatant from each well was transferred to a 96 well plate and 60 μl of reconstituted substrate solution was added to each well and then the plates were incubated for 30 min. Total LDH release was achieved by adding 2% Triton X-100 solution to untreated control cells. The absorbance of the samples was measured at 490 nm using a VictorX3 Multilabel Plate Reader (PerkinElmer). The values were expressed as a percent of the total LDH release.

Animal Treatment

For Morris water maze, mice were randomly assigned to treatment groups and the experimenter was unaware of both genotype and treatment group. Groups were balanced for age, sex, and weight. Mice used were 12-14 months of age at experiment initiation. During treatment, the experimenter was blinded to genotype. For drug treated mice, Poly(4-styrenesulfonic acid co-maleic acid) was administered by twice daily oral gavage of 5.0 mg and 15.0 mg Poly(4-styrenesulfonic acid co-maleic acid) per kg body weight in a vehicle of 0.5% w/v hydroxypropyl methylcellulose and 0.1% w/v polysorbate 80 to APP/PS1 and WT mice, respectively. Vehicle treated animals were gavaged twice daily with vehicle. 500 mg ceftazidime as Fortaz was dissolved per manufacturer's instructions in 1.5 ml sterile milliQ $H_2O$ to obtain 333 mg/ml in sodium carbonate solution. Animals treated peripherally with fresh ceftazidime were injected directly after dissolution intraperitoneally with 100 mg ceftazidime per kg body weight in a vehicle of PBS. Animals treated centrally with aged ceftazidime were fitted with an intracerebroventricular cannula (Alzet brain infusion kit 0008663) and subcutaneous osmotic minipump (Alzet model 1004) loaded with aged ceftazidime diluted in PBS. All animals were treated for 4 weeks prior to the Morris water maze and throughout assessment.

Behavioral Testing

Morris water maze was performed as previously described (Morris, 1984; Smith et al., 2018). Throughout experimentation, the experimenter was blinded to treatment group, and genotype. Each animal was handled by the experimenter for five minutes each day for three consecutive days preceding the initiation of behavioral experiments to minimize animal stress on testing days. The testing pool was ~1 meter in diameter with four unique spatial cues placed evenly around the perimeter. For learning swims, a clear plastic platform was submerged 1 cm below the surface of the water and fixed to the bottom of the pool in the target quadrant. For each swim a mouse was placed in the water facing the pool wall opposite the target quadrant in one of four positions. The sequence of the entry positions was changed for each of the six trial blocks.

For a single trial block, each animal was swum four times. For each swim mice were given 60 seconds to locate the hidden platform. Mice were given a 60 s rest interval with access to a heating lamp between swims. Trial blocks were initiated every 12 hours over three consecutive days for a total of 6 trial blocks. If a mouse failed to locate the hidden platform in the allotted time during trial blocks one or two, the mouse was gently guided to the platform and placed there for 15 s. The reverse swim began the day after completion of the forward swims and followed the same protocol with the hidden platform placed in the quadrant opposite that of the forwards swims.

Twenty-four hours after the last learning trial block of the reverse swim, the platform was removed from the pool for the probe trial. During the probe trial, each animal was placed in the pool once and allowed to freely swim for 60 s. For all swims animals were tracked using SMART 3.0 software (Panlab, S. L.—Harvard Apparatus, Inc, Holliston, MA) with a JVC Everio G-series camcorder (Yokohama, Japan).

To account for differences in visual acuity, a marker that extended above the surface of the water was placed on the platform and mice we placed in the water facing the wall opposite the platform. Latency to reach the visible platform was recorded and any animals that did not reach the platform within two standard deviations of the mean were excluded from analysis. For analysis of the learning swims, a single mouse's latency to find the platform was averaged across four swims to generate a trial average.

Fluorescence Recovery After Photobleaching (FRAP)

COS-7 green monkey kidney cells (ATCC® CRL-1651) were passaged in high-glucose DMEM (ThermoFisher, 11965092) supplemented with sodium pyruvate, 10% Fetal Bovine Serum and Pen/Strep antibiotic mix. Trypsinized cells were seeded in 8-well chambered sterile coverglass slides (ThermoFisher, 155411) at 10000 cells/well in 250 μl of complete growth medium and cultured overnight. The following day, the cells were transfected with a total of 200 ng DNA/well using Lipofectamine 3000 lipid transfection reagent (ThermoFisher, L3000015) according to manufacturer's protocol.

For fluorescent labeling, cells expressing SNAP-PrP were incubated with 500 nM SNAP-Surface Alexa Fluor647 in complete medium for 30 min at 37° C. Cells were washed twice with PBS supplemented with calcium and magnesium (Sigma, D8662) to remove the excess labeling fluorophores and then incubated for 15 min in $PBS^{Ca,Mg}$ with 1 μM PSCMA or $PBS^{Ca,Mg}$ alone as a control. Aβo or PBS (vehicle) was subsequently applied to 1 μM final concentration for 1 h at 37° C. and cells were then imaged at room temperature.

All FRAP experiments were performed on UltraVIEW VOX (Perkin Elmer) SDC microscope equipped with Photo-Kinesis FRAP unit using 60× oil immersion objective. Images were collected every second for 7 s. before bleaching to measure the baseline fluorescence. Following the bleaching cycle, the imaging was performed with 1 s intervals for the first 30 seconds and with 4 s intervals for 220 additional sec. 640 nm laser was used for selective photobleaching of SNAP-PrP conjugated with Alexa 647. All the imaging was performed in the apical membrane of the cells and at least three 2×2 μm areas per cell were bleached to average the intrinsic variability in the protein mobility between the regions of the plasma membrane. Quantitation of fluorescence recovery was performed in Volocity software (PerkinElmer).

Immunohistology

Mice were euthanized by CO2 asphyxiation, perfused with cold PBS and brains were dissected and post-fixed in 4% paraformaldehyde for 72 hr at 4° C. Brains were sliced into 40 μm coronal brain sections using a Leica WT1000S vibratome. Sections were permeabilized in PBS+0.1% Triton X-100 for 15 min. All slices underwent an antigen retrieval step prior to exposure to primary antibody by incubating slices in 1× Reveal Decloaker buffer (RV1000M, Biocare Medical) for 15 min at 90 C in an oven. After antigen retrieval, sections were blocked in 10% normal horse serum (Jackson ImmunoResarch Laboratories) in PBS for 1 hour at room temperature and then incubated with primary antibodies for 24 hours at 4 C. The following primary antibodies were used: anti-GFAP (glial fibrillary acidic protein; Abcam ab4674; 1:500), anti-Iba1 (ionized calcium-binding adapter molecule 1; Wako 019-19741; 1:250), anti-PSD95 (postsynaptic density protein 95; Invitrogen 51-6900; 1:250), and anti-SV2a (synaptic vesicle glycoprotein 2A; Abcam 32942; 1:250). Sections were washed 3 times in PBS and incubated with secondary antibodies (donkey anti-rabbit or donkey anti-chicken fluorescent antibodies; Invitrogen Alexa Fluor; 1:500) for 1 hour at room temperature. After 3 washes in PBS, the sections were mounted onto glass slides (Superfrost Plus, Fisher Scientific) and coverslipped with Vectashield (Vector Laboratories H-1200) antifade aqueous mounting medium.

Imaging and Analysis of Immunohistochemistry

For imaging of synapse density stained by anti-SV2a and anti-PSD95 antibodies, a Zeiss 800 confocal microscope with a 63× 1.4 NA oil-immersion lens was used. The area occupied by immunoreactive synaptic puncta from the molecular layer of the dentate gyrus was measured as described previously (Gimbel et al., 2010). For imaging and analysis of the tissue stained for Iba1 and GFAP, a Zeiss 800 confocal microscope with a 20× 0.3 air-objective lens was used and a full tiled z stack of the hippocampus was taken. β-amyloid plaque load was imaged on a Zeiss AxioImager Z1 fluorescent microscope with a 4× air-objective lens (ASK LEVI). ImageJ software was used for quantification. Statistical analysis was based on separate mice.

Thioflavin S Aβ Plaque Staining

60 μm sections were incubated in pre-heated 10 mM sodium citrate with 0.05% Tween 20, pH 6 at 95° C. for 1 hour, rinsed twice with PBST and blocked with 10% donkey serum (Jackson ImmunoResearch 017-000-121) for 1 hour. Next, sections were incubated in 0.1% Thioflavin S (Sigma T1892) in 70% ethanol at room temperature for 15 minutes, washed twice with 70% ethanol, then twice with distilled water. Images of cortical Thioflavin S staining were collected from three slices for each animal and quantified using ImageJ. Three values for a single animal were averaged and graphed as a single data point per animal Mouse Pharmacokinetic (PK) Study Brain penetration of ~20 kDa PSCMA (Sigma, 434566) was characterized in six male C57BL/6 mice. Mice received drug at 40 mg/kg as a solution in 95% PEG400/5% Solutol (dose volume=5 mL/kg) by oral gavage. After 10 days of treatment, mice were euthanized by CO2 asphyxiation, perfused with ice-cold PBS for 60 seconds, and brains were rapidly dissected. Whole brains were Dounce homogenized in 1:10 w: v brain:PBS, followed by polyanion extraction using TRIzol™ reagent (Invitrogen, 15596026). 1 ml trizol per 100 mg tissue was added, vortexed, 0.2 ml chloroform per ml TRIzol added, vortexed, centrifuged 15 min at 12,000×g, aqueous phase transferred to a new tube, 0.5 ml isopropanol added per ml TRIzol used for lysis, incubated 15 min, centrifuged at 12,000×g, supernatant retrieved leaving RNA pellet, supernatant speed vacuumed overnight, resuspended in $H_2O$ and purified using Oasis® WAX cartridges (Waters, 186002489). Eluted extracted PSCMA was assayed for Aβo/$PrP^C$ inhibitory activity by PrP-ELISA or PLISA (Kostylev, 2014).

Analysis of Dendritic Spine Density (PSS)

For Aβo-induced spine loss, Aβo (1 μM monomer, 10 nM oligomer estimate), vehicle (veh), Aβo+PSS, or PSS alone were applied at the designated dose to GFP transfected neurons at DIV 17, replacing 50% culture medium with fresh Aβo+veh, Aβo+PSS, or Veh-containing conditioned culture medium every 24 hours for 4 days thereafter. Neurons were fixed and imaged with a 40× objective oil lens on a Nikon Eclipse Ti Spinning Disk Confocal Microscope driven by Volocity software (PerkinElmer). Images were obtained as a 1 µm Z-stack with 0.5 µm spacing using a 488 laser. All imaging and analyses were completed by an observer unaware of genotype or treatment group. Analysis and quantification of data were performed with Volocity software after max intensity projection. The number of dendritic spines were counted manually to estimate the density of primary or secondary dendritic branch by observer unaware of treatment. For each condition, at least 3 dendrites were measured from each neuron and 5-7 neurons were imaged per coverslip.

Quantification and Statistical Analysis

All results are presented as means±SEM. Microsoft Excel, Prism 6 software and IBM SPSS Statistics 1 were used for statistical analysis. Data were analyzed using one-way or two-way ANOVA, followed by post hoc Tukey's multiple comparisons test, as specified in the figure legends. Only two-sided tests were used, and all data analyzed met the assumption for the specific statistical test that was performed. Probability levels of $P<0.05$ were considered statistically significant.

| Reagent and Resourse Table | | |
|---|---|---|
| REAGENT or RESOURCE | SOURCE | IDENTIFIER |
| Antibodies | | |
| Thioflavin S | Sigma-Aldrich | Cat# 230456 |
| Eu-labeled streptavidin | PerkinElmer | Cat# 1244-360 |
| 488-streptavidin | Life technologies | Cat# S11223 |
| SAF32 mouse anti-PrP | Cayman Chemical | Cat# 189720-1 |
| IRDye 800CW Donkey anti-Mouse IgG (H + L) | Li-Cor | Cat# 925-32212 |
| 8B4 mouse anti-PrP | Santa Cruz Biotech | Cat# Sc-47729 |
| 5058 mouse anti-PrP | Millipore Sigma | Cat# AB5058 |
| 8G8 mouse anti-PrP | Cayman Chemical | Cat# 189760 |
| 6D11 mouse anti-PrP | Covance | Cat# SIG-399810 |
| Pri 308 mouse anti-PrP | Cayman Chemical | Cat# 189750 |
| 8H4 mouse anti-PrP | abcam | Cat# Ab61409 |
| SAF70 mouse anti-PrP | Cayman Chemical | Cat# 189770 |
| Rabbit anti-SV2A | Abcam | Cat# 32942 |
| Mouse anti-NeuN | Millipore | Cat# Mab377 |
| Rabit anti-actin | Cell Signaling Technology | Cat# 4967S |
| 555-streptavidin | invitrogen | Cat# S32355 |
| Rabbit anti-Fyn | Cell Signaling Technology | Cat# 4023 |
| Rabbit anti-phospho-Src | Cell Signaling Technology | Cat# 2101 |
| IRDye 680 CW Donkey anti-rabbit IgG (H + L) | Li-Cor | Cat# 925-68073 |
| Bacterial and Virus Strains | | |
| Chemicals, Peptides, and Recombinant Proteins | | |
| Aβ1-42: DAEFRHDSGYEVHHQKLVFFAEDVG SNKGAIIGLMVG GVVIA | The ERI Amyloid Laboratory, LLC | amyloid.peptides@att.net |
| Z | This paper | Z |
| Proteinase K | Roche Applied Science | Cat# 1373-196 |
| Sepharose Q fast-flow medium | GE Healthcare | Cat# 17051001 |
| DELFIA assay buffer | Perkin Elmer | Cat# 4002-0010 |
| phenol red-free F12 | Atlanta Biologicals | Cat#: M15350 |
| Goat serum | Life technologies | Cat# 16210-064 |
| DELFIA Enhancement Solution | Perkin Elmer | Cat# 4001-0010 |
| 1,1,1,3,3,3-Hexafluoro-2-propanol | Sigma-Aldrich | Cat#: 105228 |
| DMSO | Americanbio | Cat#: AB00435-00500 |
| Enzo FDA Approved Drugs Library | Enzo Life Sciences | SCREEN-WELL ® FDA approved drug library V2 |
| Microsource Pharm 1600 library | Microsource | Pharm 1600 |
| ChemDiv Targeted Diversity library | ChemDiv | Targeted Diversity library |
| Yale Small Molecule Discovery Center compound collection | This paper | Yale Small Molecule Discovery Center compound collection |
| Formaldehyde, 37% | J.T. Baker | Cat# 2106-01 |
| Ceftazidime (Fortaz) | GlaxoSmithKline | Cat# NDC 0173-0377-10 |
| biotin-NHS | Thermo Scientific | Cat# 21329 |
| Tween 20 | Sigma-Aldrich | Cat# P7949 |
| T20 PBS blocking buffer | Pierce | Cat# 37573 |

-continued

Reagent and Resourse Table

| REAGENT or RESOURCE | SOURCE | IDENTIFIER |
|---|---|---|
| ChemDiv Diversity Library | ChemDiv | Targeted Diversity Library |
| Trypsin 0.25% | Gibco | Cat# 25200-056 |
| GlutaMAX | Gibco | Cat# 35050-061 |
| Sodium pyruvate | Gibco | Cat# 11360-070 |
| Pen strep | Gibco | Cat# 15140-122 |
| Neurobasal media | Gibco | Cat# 10888-022 |
| Triton X-100 | American bioanalytical | Cat# AB02025-00500 |
| Lipofectamine 3000 | ThermoFisher | Cat# L3000015 |
| $PBS^{Ca,Mg}$ | Sigma Aldrich | Cat# D8662 |
| Polysorbate 80 | Sigma Aldrich | Cat# W291706 |
| SNAP-Surface Alexa Fluor 647 | New England Biolabs | Cat# S9136 |
| PBS, pH 7.4 10× | Americanbio | Cat# AB11072 |
| Papain | Sigma-Aldrich | Cat# P5306 |
| Polystyrene sulfonate (PSS) | PSS Polymer Standards Service GmbH | Cat# PSS-pss3.4K or PSS-pss17K |
| Poly(ethylene glycol) | Sigma-Aldrich | Cat# 94646 |
| Poly(4-styrenesulfonic acid-co-maleic acid) sodium salt (PSCMA) | Sigma-Aldrich | Cat# 434566 |
| Poly(acrylic acid) sodium salt | Sigma-Aldrich | Cat# 447013 |
| Poly(methacrylic acid) sodium salt | Sigma-Aldrich | Cat# 434507 |
| Poly(acrylic acid co-maleic acid) solution | Sigma-Aldrich | Cat# 416053 |
| Pentosan polysulfate sodium | BOC Sciences | Cat# 116001-96-8 |
| Poly-d-glutamic acid sodium salt | Sigma-Aldrich | Cat# P4033 |
| Dextran sulfate sodium salt | Sigma-Aldrich | Cat# D4911 |
| Poly (2-acrylamido-2-methyl-1-propanesulfonic acid) | Sigma-Aldrich | Cat# 191973 |
| Poly (styrene-co-maleic acid) partial isobutyl ester | Sigma-Aldrich | Cat# 435287 |
| Poly (styrene-alt-maleic acid) sodium salt | Sigma-Aldrich | Cat# 662631 |
| Critical Commercial Assays | | |
| Cytotoxicity Detection Kit | Roche | Cat# 11644793001 |
| Deposited Data | | |
| Experimental Models: Cell Lines | | |
| CV-1 cells | ATCC | Cat# CCL-70 |
| Green monkey: COS-7 kidney cells | ATCC | Cat# CCL-1651 |
| Experimental Models: Organisms/Strains | | |
| Oligonucleotides | | |
| Recombinant DNA | | |
| SNAP-PrP in pcDNA3.1 vector | This paper | SNAP-PrP |
| pSNAP-tag vector | New England Biolabs | Cat#: N9183 |
| Full-length $PrP^C$ (AA23-231) in pRSET A vector | (Zahn et al., 1997) | PrP, PrP-FL |
| Full-length $PrP^C$ in PCDNA3 | This paper | |
| Software and Algorithms | | |
| GraphPad Prism 7 | graphpad | Graphpad.com |
| volocity | PerkinElmer | Volocity 6.3 |
| imageJ | Imagej.nih.gov | imageJ |
| Image Studio | LiCor | www.licor.com/bi |
| Other | | |
| 3 kilodalton filter | Amicon | Cat# UFC500396 |
| XK 50/20 column | GE Healthcare Life Sciences | Cat# 9621706 |
| Q Sepaharose Fast Flow | GE Healthcare Life Sciences | Cat# 17-0510-01 |
| BLI streptavidin Biosensors | Forte Bio | Cat# 18-5019 |
| 4-16% NOVEX Bis-Tris gel | ThermoFisher | Cat# BN1002BOX |
| western blot blocking buffer | Rockland | Cat# MB-070-010TF |
| MaxiSorp 384 microplates | ThermoFisher | Cat# 460372 |
| D-lysine-coated glass 8 well coverslip | Lab-Tek | Cat# 155411 |
| intracerebroventricular cannula | Alzet | Cat# 0008663 |
| AKTApurifier 10 FPLC System | GE Healthcare | Cat# 28406264 |
| iBlot dry transfer system | Thermo Fisher Scientific | Cat# IB1001 |

Example 1

Degradation of Ceftazidime Produces a Potent Polymeric Inhibitor of Aßo/PrP$^C$ Interaction, Termed Compound "Z"

A high throughput cell-based screen using stably PrP$^C$-transfected CV-1 cells was used to find small molecule inhibitors of Aßo/PrP$^C$ interaction. Aßo prepared from biotinylated synthetic Aß peptide associates with these cells in a PrP$^C$-dependent fashion that can be blocked by an antibody (6D11) directed against the Aßo-binding domain at PrP$^C$ 90-111 (FIG. 1, 2). From a screen of 2,560 known drug and ~10,130 diverse small molecules stored in frozen DMSO, the cephalosporin antibiotic cefixime sample was found to be highly inhibitory.

Figure 3:
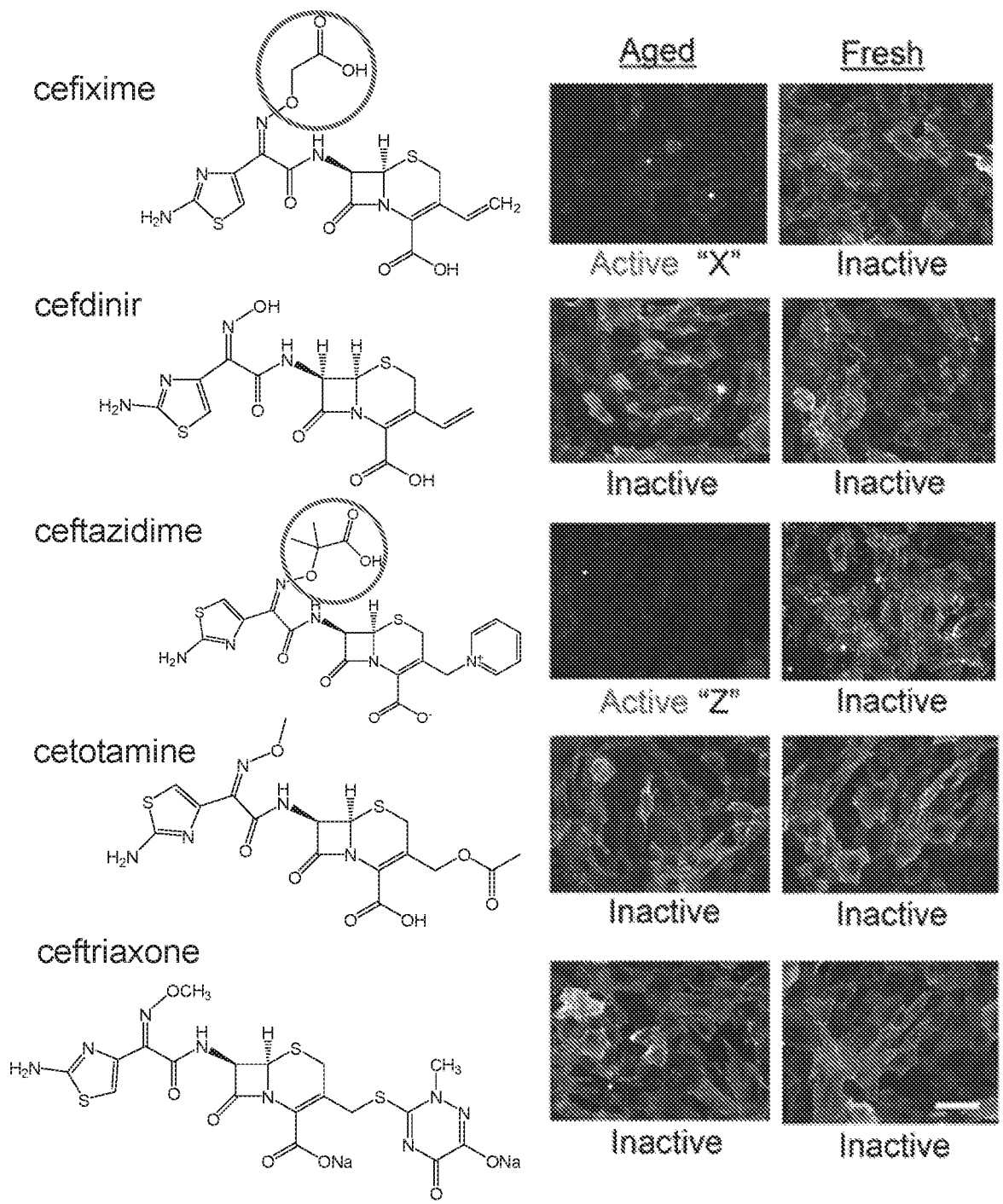
FIG. 3 is a series of illustrations showing Aβo/$PrP^C$ interaction-inhibiting activity of five cephalosporin antibiotics applied to stably $PrP^C$-transfected CV1 cells followed by treatment with biotinylated Aβo (500 nM monomer equivalent). "Fresh" column: 10 μM drug applied immediately upon dissolution. "Aged" column: 10 μM drug applied six days post dissolution. Circles: acid groups common to cephalosporins that acquire activity post-aging. Scale bar=5 μ.

Upon repurchase of material for validation, neither fresh cefixime nor a range of other cephalosporins were found to possess inhibitory activity, suggesting an impurity or degradation product of cefixime was responsible for the observed activity (compound "X"). To investigate this possibility, five different cephalosporins were allowed to stand in DMSO at RT for six days before re-testing. In addition to cefixime, ceftazidime exhibited activity resulting from prolonged incubation in solution (compound "Z"), while three other cephalosporins (cefdinir, cefotaxime and ceftriaxone) exhibited zero activity either freshly diluted or after six days in DMSO solution (FIG. 3).

Example 2

Compound Z Binds PrP$^C$ with Nanomolar Affinity

Figure 2:
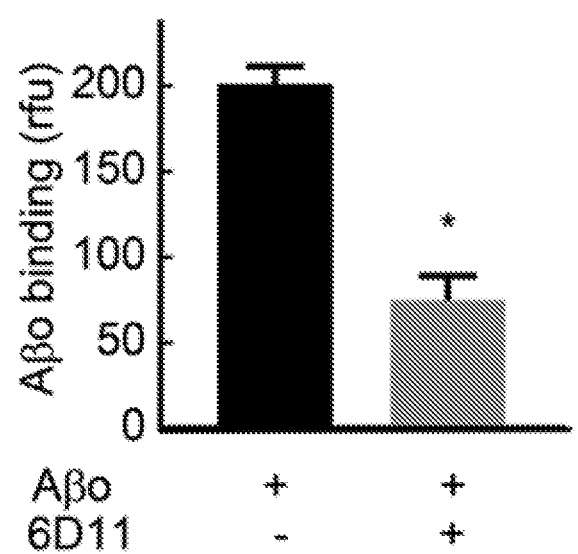
FIG. 2 is a bar graph showing the quantitation of Aβo-binding in FIG. 1, background subtracted. Data are mean+/−SEM, n=3 wells. (*, P<0.05, Student's 1-test).

The potency and rapid rate of generation from ceftazidime led to a focus on compound Z for additional studies. Fractionation by size exclusion chromatography (SEC) demonstrated broad high molecular weight of the activity (FIG. 4, 5), consistent with the reported polymerization of a negatively charged R group degradant of ceftazidime (Baertschi et al., 1997; Ercanli and Boyd, 2006). Both cefixime and ceftazidime possess a negatively charged R group, while other cephalosporins do not, consistent with this fragment being the source of the activity (FIG. 2). Elution of Z by high NaCl concentrations (100-130 millisiemens) in anion exchange chromatography confirmed that Z is highly negatively charged. Measurement of Aßo-binding inhibitory activity of the 20 kDa Z SEC fraction by PrP$^C$-Linked Immunosorbent Assay (PLISA) or PrP$^C$ binding affinity by biolayer interferometry (BLI), indicated an EC$_{50}$ of 3.4 nM and K$_D$ of 5.7 nM, respectively. Conversely, Z showed no affinity for Aßo by BLI (FIG. 6), indicating specificity of affinity for Prp$^C$.

Figure 9:
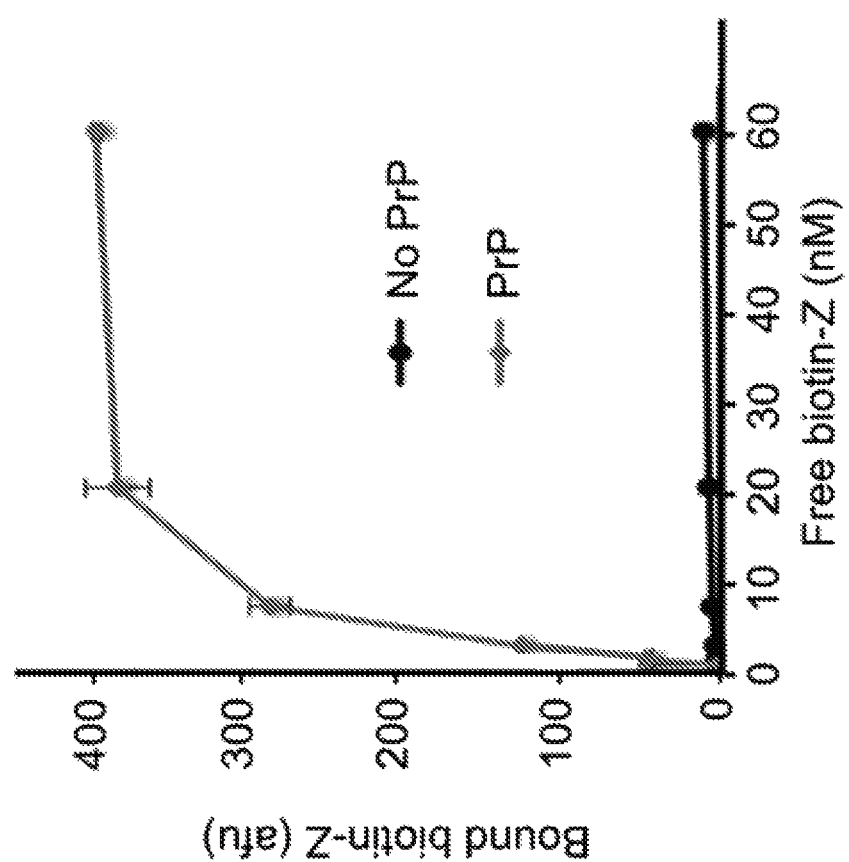
FIG. 9 is a line graph showing biotinylated 10-20 kDa Z binds full-length $PrP^C$-coated plate concentration-dependently. Data are mean+/−SEM, n=3 replicates per sample.
Figure 10:
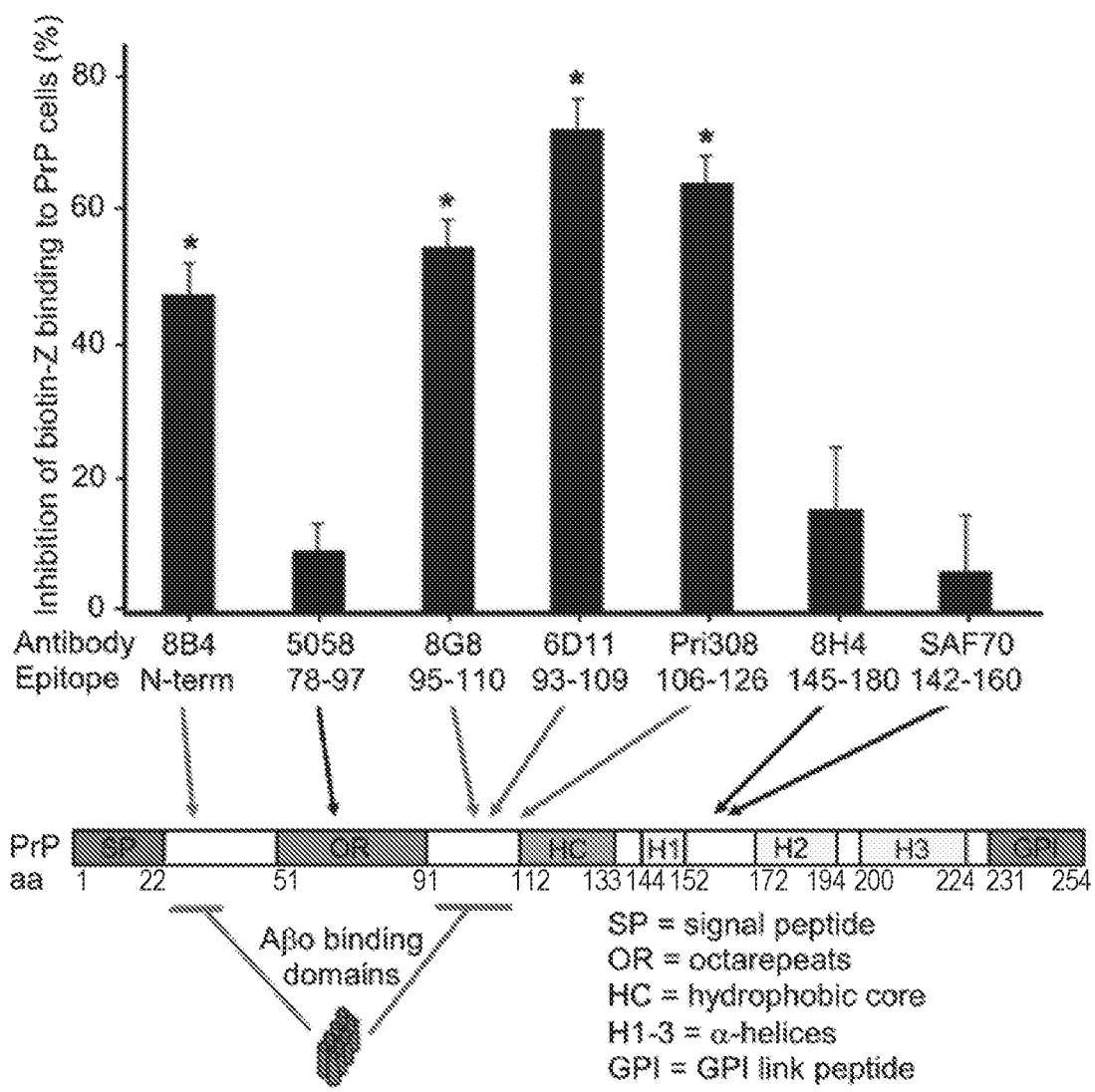
FIG. 10 is a bar graph showing binding of biotinylated Z to $PrP^C$-coated plate is inhibited by antibodies directed against either of the two Aβo-binding domains on $PrP^C$ and not by antibodies against other regions of PrP, indicating direct and selective Z interaction with $PrP^C$ Aβo-binding domains. Data are mean+/−SEM, n=3 replicates per sample. (*, P<0.05, student's t-test).

Aßo associates with two lysine-rich domains mapped to the PrP$^C$ N-terminus region: PrP 23-31 and 90-111. To determine whether Z directly associates with these epitopes, it was tested whether antibodies against specific PrP$^C$ epitopes could inhibit Z binding to PrP$^C$. Biotinylated Z exhibited unaltered PrP$^C$ affinity in a plate-based Z-Linked Immunosorbent Assay (ZLISA) (FIG. 9), enabling the evaluation of PrP$^C$-directed agents to compete with Z. Antibodies directed against PrP$^C$ in the 23-31 or 90-111 regions were able to block soluble biotin-Z binding to plate-bound PrP$^C$, while antibodies directed against other PrP$^C$ domains did not (FIG. 10), consistent with direct occupation of these sites by Z. PrP gel shift assay showed laddering of PrP$^C$ in the presence of Z that could be reversed by heating to 65 C, indicating non-covalent reversible binding between multivalent Z and PrP$^C$ (FIG. 3). Taken together, these data indicate Z is a PrP$^C$-binding reversible competitive antagonist of Aßo/PrP$^C$ interaction.

Example 3

Compound Z Blocks Aßo Action and PrP$^{Sc}$ Propagation In Vitro

Figure 11:
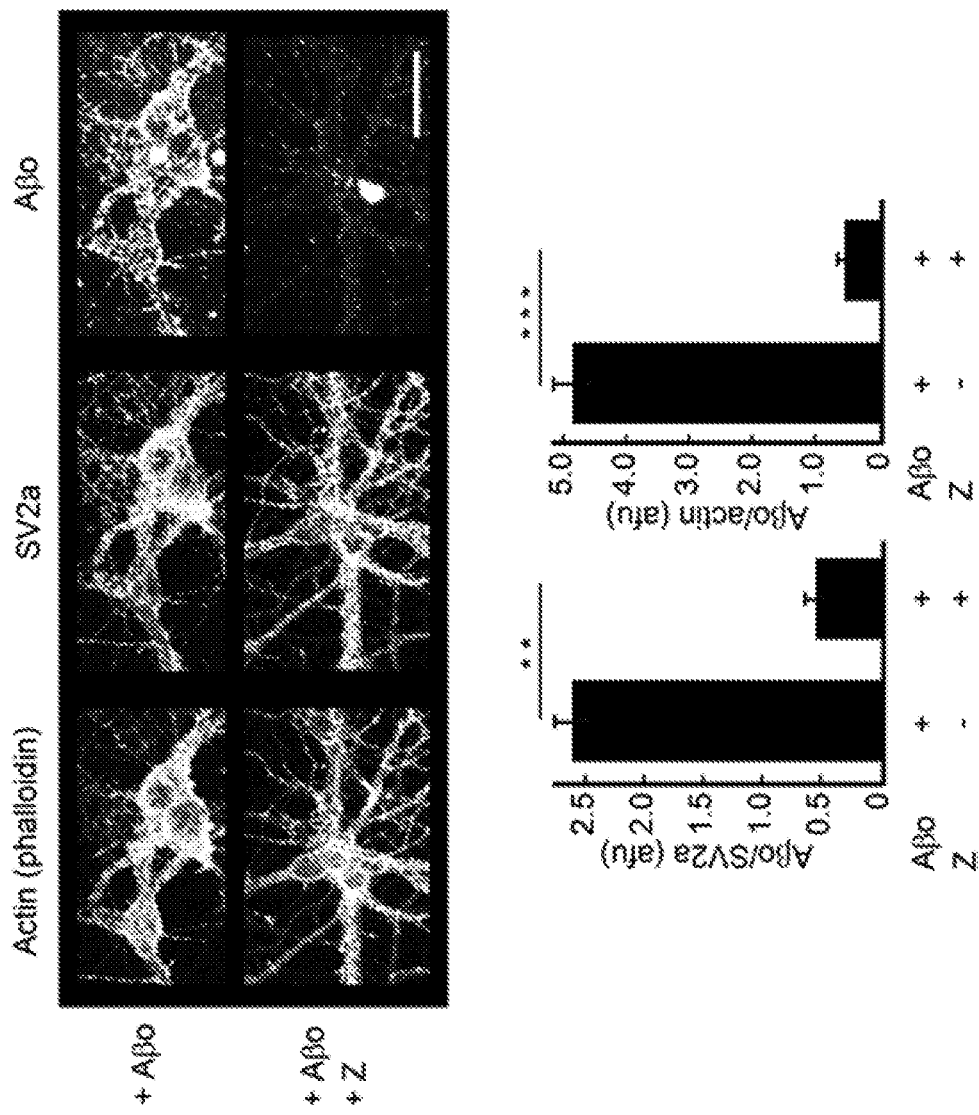
FIG. 11 is an illustration and two bar graphs showing Aβo (1 μM monomer equivalent) binding to DIV 19 mouse hippocampal neurons is blocked by 50 nM 10-20 kDa Z. 80% and 87% of neuronal Aβo binding is inhibited relative to the neuronal markers SV2a and actin, respectively. Scale bar=10 μM. Data are mean+/−SEM, n=3 wells. (, P<0.01; *, P<0.001 Student's 1-test).
Figure 12:
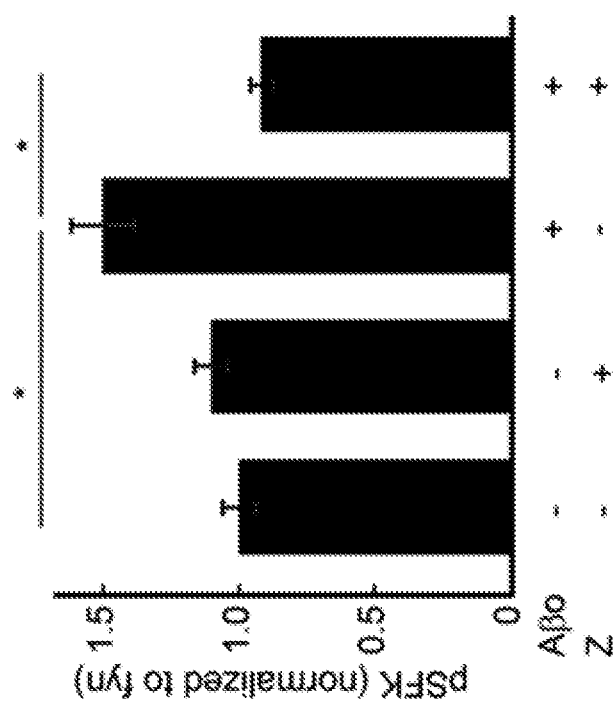
FIG. 12 is a bar graph showing induction of phospho-SFK (Src Family Kinase) in DIV 21 mouse cortical neurons by 30 min application of Aβo (1 μM) is blocked by 10-20 kDa Z (50 nM). Phospho-SFK is normalized to total Fyn which is the predominant neuronal SFK family member activated by Aβo (Um et al., 2012). Data are mean+/−SEM, n=3 wells. (*, P<0.05 by one-way ANOVA with Tukey's post hoc multiple comparisons test).
Figure 13:
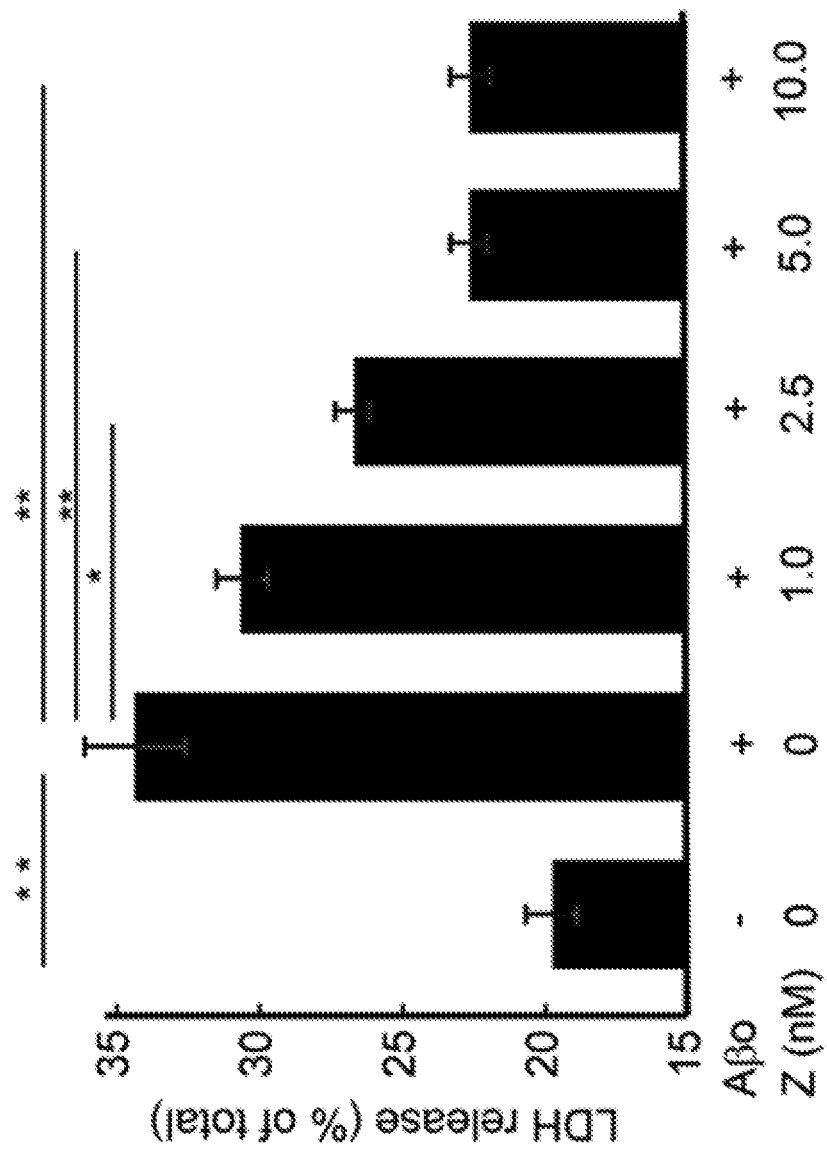
FIG. 13 is a bar graph showing neurotoxic action of 6 hr Aβo (3 μM) treatment of DIV 21 hippocampal neurons is blocked dose-dependently by 10-20 kDa Z, as indicated by LDH release, with maximal effect reached at 5 nM Z. (*, P<0.05 by one-way ANOVA with Tukey's post hoc multiple comparisons test).
Figure 14:
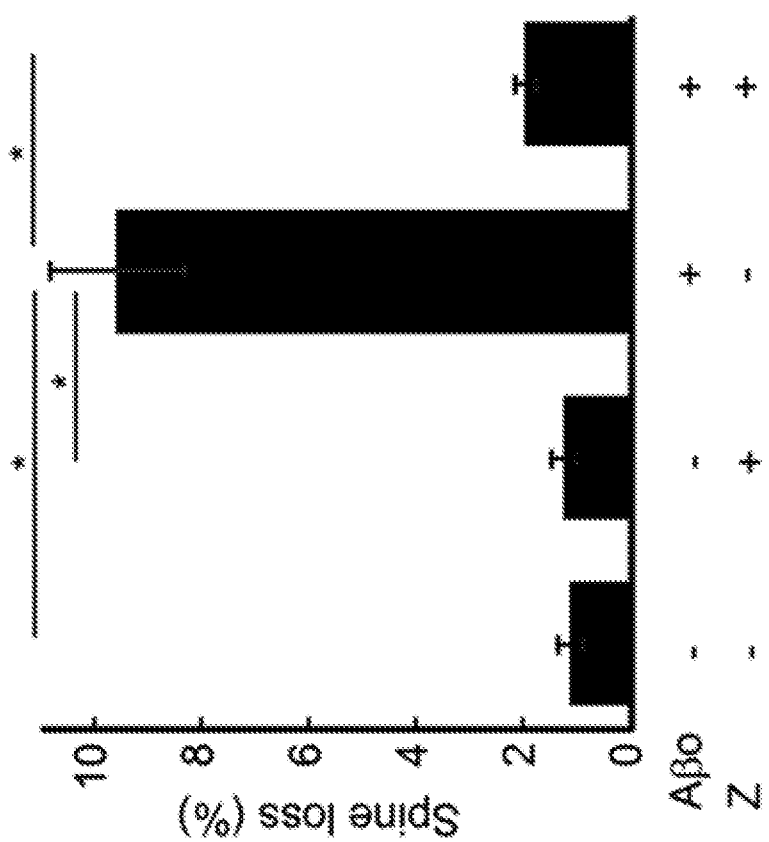
FIG. 14 is a bar graph showing induction of DIV 20 hippocampal neuronal dendritic spine loss by 6 hr application of Aβo (500 nM) is blocked by co-incubation with 10-20 kDa Z (100 nM). (*, P<0.05; **, P<0.01 by one-way ANOVA with Tukey's post hoc multiple comparisons test).
Figure 15:
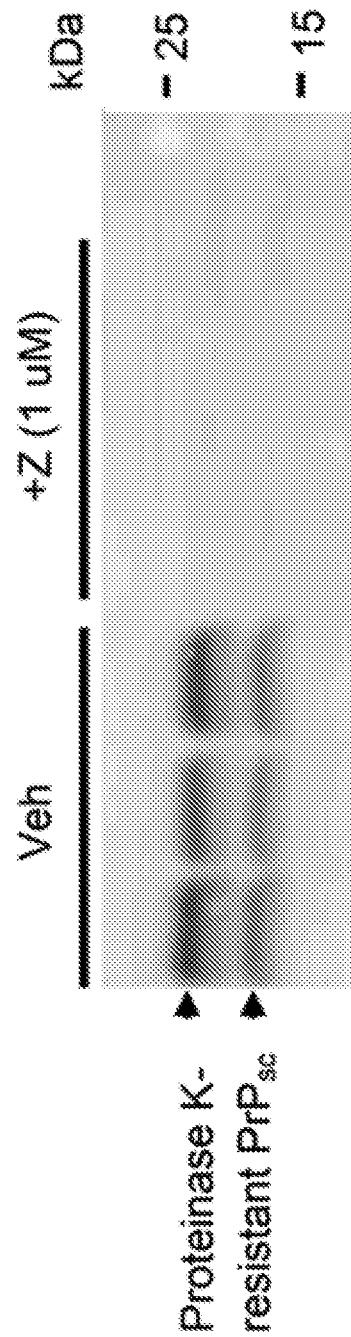
FIG. 15 is an illustration showing that propagation of proteinase K-resistant $PrP^{Sc}$ prion in N2a cell culture is blocked by 48 hr application of 10-20 kDa Z (1 μM) as revealed by anti-PrP immunoblot.

Functionally, Z blocks numerous metrics of Aßo action. Aßo association with DIV 19 mouse cortical neuronal cultures is reduced by more than 80% in the presence of Z (FIG. 11). In addition, co-incubation with Z fully blocks Aßo-induced Fyn activation in cortical neuron cultures detected with a phospho-specific anti-Fyn pY416 antibody (FIG. 12). The PrP$^C$-mediated synaptotoxic action of Aßo is evidenced in hippocampal neuronal culture by the induction of an eight-fold increase of dendritic spine loss (FIG. 14). Co-administration of 100 nM Z with 1 µM Aßo prevented 92% of Aßo-induced spine loss in hippocampal cultures (FIG. 14). Treatment of DIV 21 hippocampal neurons for 6 hr with a higher concentration of Aßo (3 µM) exerted a neurotoxic action evidenced by induction of LDH release. This Aßo-induced LDH release was blocked dose-dependently by Z, with an IC$_{50}$ of approximately 2.0 nM (FIG. 13). Given the efficacy of Z in vitro with regard to PrP$^C$-mediated Alzheimer's processes, we sought to determine whether Z could also affect the PrP$^C$-mediated prion propagation that underlies TSE. Indeed, in an N2A cell culture PrP$^{Sc}$ propagation assay, treatment with Z (1.0 µM) cleared PrP$^{Sc}$ infection as detected by the elimination of proteinase K resistant PrP (FIG. 15).

Example 4

Compound Z Rescues Transgenic APP/PS1 Mouse Memory Deficits

Figure 4:
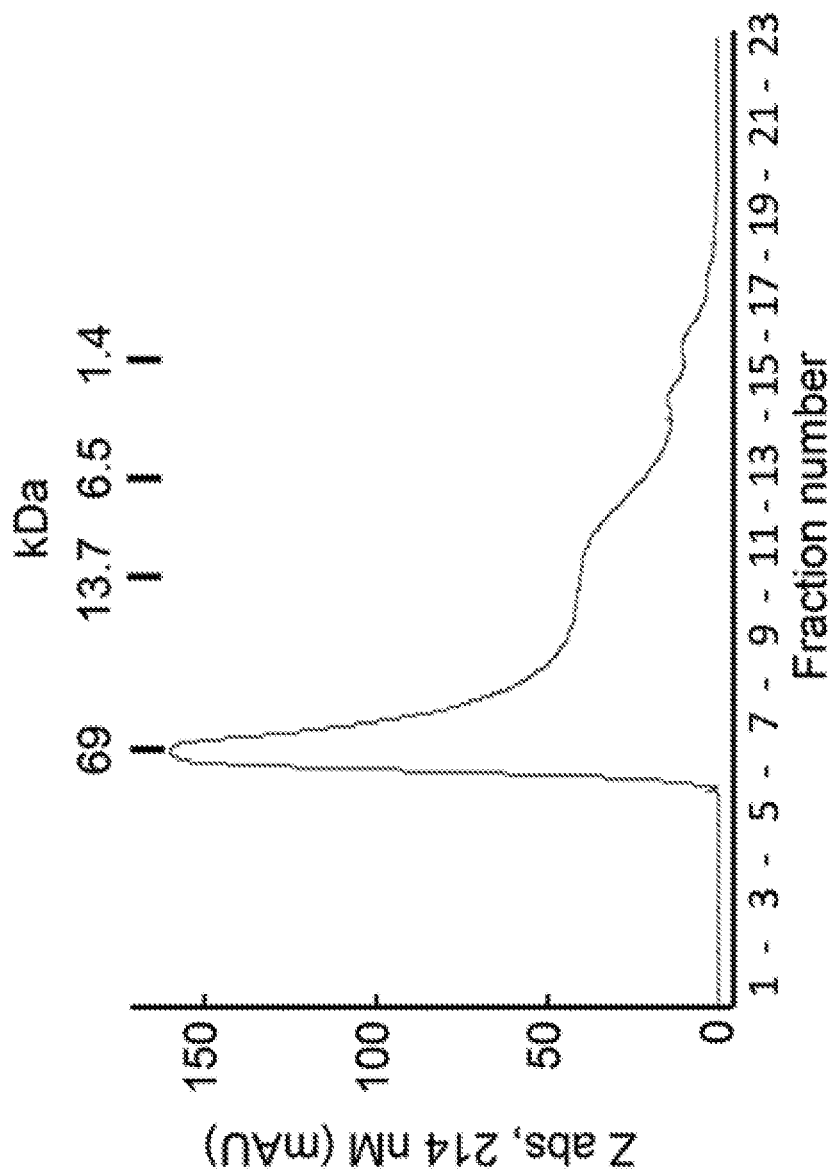
FIG. 4 is a line graph showing an absorbance trace from size exclusion chromatography (SEC) fractionation of aged ceftazidime activity (polymer "Z"). MW standards at top of graph.
Figure 5:
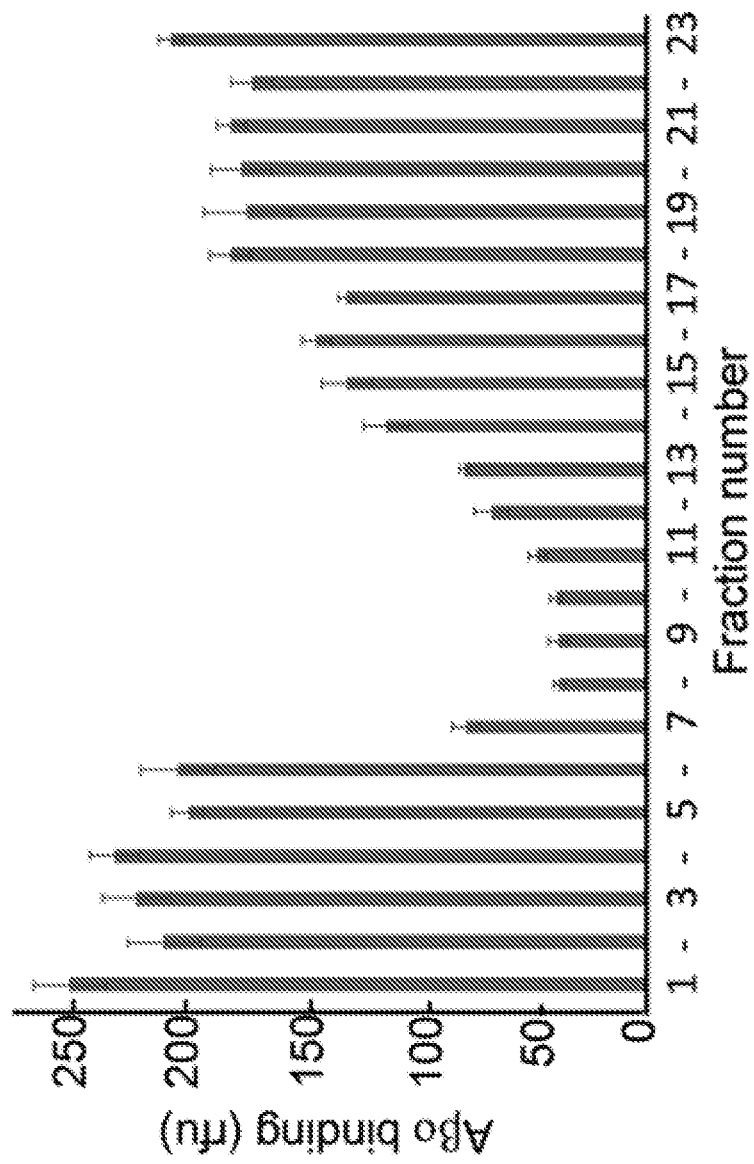
FIG. 5 is a line graph showing Aβo/$PrP^C$ interaction-inhibitory activity of SEC fractions from (D) as measured by PLISA biochemical assay. Maximal activity resides in the HMW fractions of aged ceftazidime.
Figure 16:
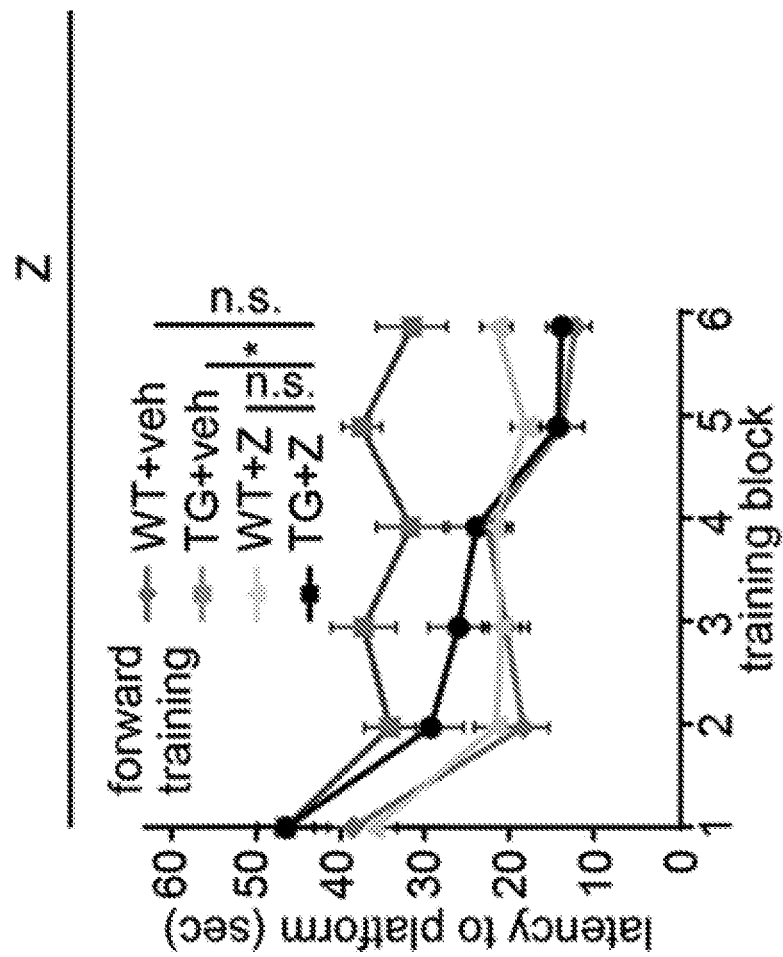
FIG. 16 is a line graph showing ceftazidime (as Fortaz®) was solubilized at 333 mg/ml in sodium carbonate per manufacturer's instructions and allowed to stand 14 days at room temperature to generate active compound Z. Z or vehicle (veh) was administered intracerebroventricularly (ICV) by osmotic minipump to 12-14 month-old wild type (WT) or APP/PS1 (TG) mice for four weeks at a rate of 10 nM 10-20 kDa Z activity-equivalent per day per 500 μl brain volume, before subjecting the mice to memory assessment by MWM. Data are mean+SEM of 9-11 mice/group. Performance was analyzed by two-way analysis of variance with RM-ANOVA over the last sixteen trials (four blocks) and showed a significant effect of genotype (*, P<0.05). The vehicle-treated APP/PS1 group differed significantly from all other groups by one-way RM-ANOVA over the last eight trials with Tukey's post hoc multiple comparisons test (*, P<0.05), whereas all other comparisons were not significantly different (P>0.05).
Figure 17:
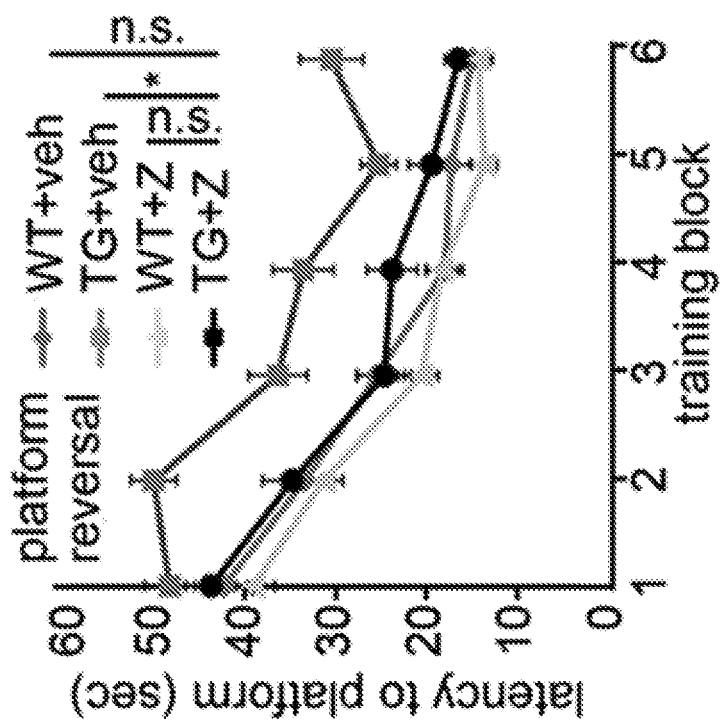
FIG. 17 is a line graph showing ceftazidime (as Fortaz®) was solubilized at 333 mg/ml in sodium carbonate per manufacturer's instructions and allowed to stand 14 days at room temperature to generate active Z (Z). Z or vehicle (veh) was administered intracerebroventricularly (ICV) by osmotic minipump to 12-14 month-old wild type (WT) or APP/PS1 (TG) mice for four weeks at a rate of 10 nM 10-20 kDa Z activity-equivalent per day per 500 µl brain volume, before subjecting the mice to memory assessment by MWM. Data are mean+SEM of 9-11 mice/group. Performance was analyzed by two-way analysis of variance with RM-ANOVA over the last sixteen trials (four blocks) and showed a significant effect of genotype (*, P<0.05). The vehicle-treated APP/PS1 group differed significantly from all other groups by one-way RM-ANOVA over the last eight trials with Tukey's post hoc multiple comparisons test (*, P<0.05), whereas all other comparisons were not significantly different (P>0.05).
Figure 18:
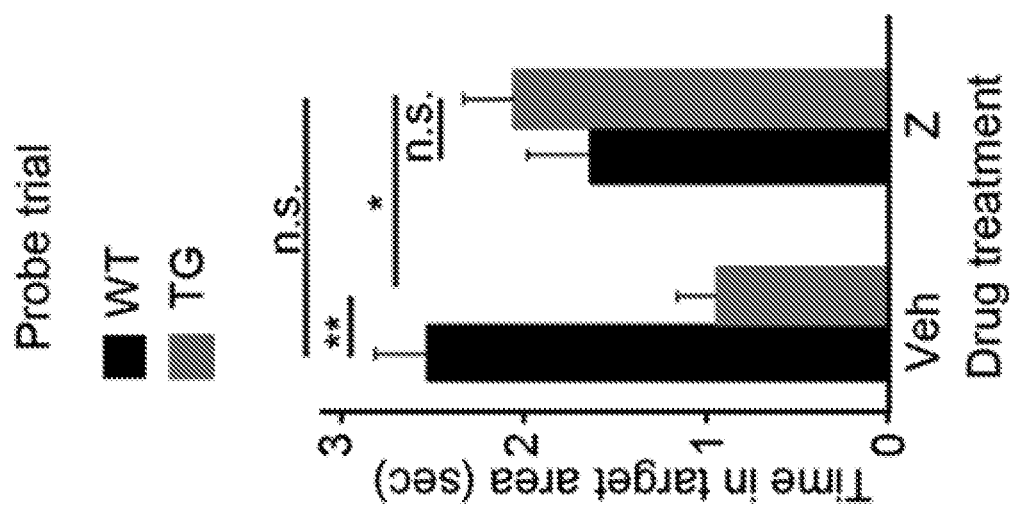
FIG. 18 is a bar graph showing a 60-s probe trial test was performed 24 hr after completion of platform reversal training in the MWM. Plotted is the time spent in the area where the platform was previously located (target area). Vehicle treated APP/PS1 transgenic Alzheimer's model (TG) mice spent significantly less time in the target area than WT mice, reflecting AD memory deficit. TG mice treated with Z underwent normalization of time spent in the target area relative to WT mice treated with Z, reflecting restored memory function. Data are mean+SEM of 9-12 mice/group. One-way ANOVA with Tukey's post-hoc comparisons.

Spatial memory performance by Morris water maze (MWM) of aged APP/PS1 mice was assessed after one month of treatment with Z (FIG. 4). The large size and negative charge characteristics of the molecule predicted inefficient transit across the blood brain barrier (BBB) such that polymerized compound might need to be administered centrally. Therefore, Z was delivered chronically by intracerebroventricular (ICV) minipump infusion beginning at 12-14 months (FIG. 16-18), when learning and memory deficits are established in this strain together with Aß accumulation (Gimbel et al., 2010; Haas et al., 2016; Kaufman et al., 2015; Kostylev et al., 2015; Salazar et al., 2017; Um et al., 2013). CNS administration rescued mice from phenotypic memory impairment across six twice-daily blocks of two learning trials to a hidden platform (FIG. 4A), and during reversal trials to a new location (FIG. 17). Memory performance during a probe trial performed 24 hours after the learning trials was impaired in vehicle-treated APP/PS1 mice compared to WT, and restored by ICV Z treatment (FIG. 18).

Figure 19:
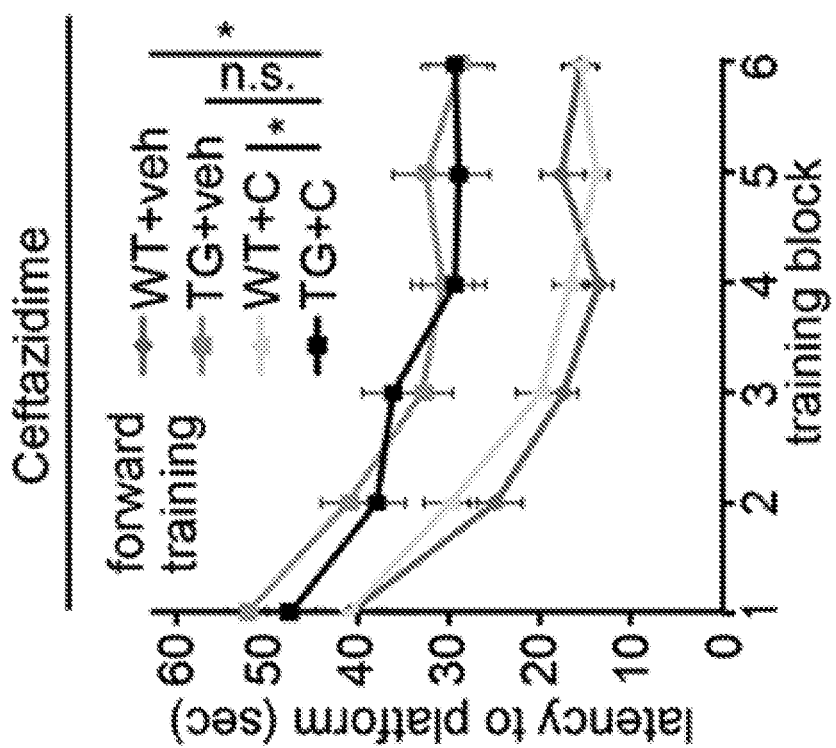
FIG. 19 is a line graph showing 100 mg/kg ceftazidime (as Fortaz® freshly solubilized at 333 mg/ml in sodium carbonate) or vehicle (veh) was administered by intraperitoneal (IP) injection BID for 6 weeks to 12-14 month-old wild type (WT) or APP/PS1 transgenic Alzheimer's model (TG) mice. Four weeks post-treatment initiation, spatial memory was assayed by Morris water maze (MWM) and plotted as the latency to locate a hidden platform. Data are mean+SEM of 10-12 mice/group. Performance was analyzed by two-way analysis of variance with RM-ANOVA over the last sixteen trials (four blocks) and showed a significant effect of genotype (*, P<0.05), but not of treatment in the initial (forward) set of training blocks.
Figure 20:
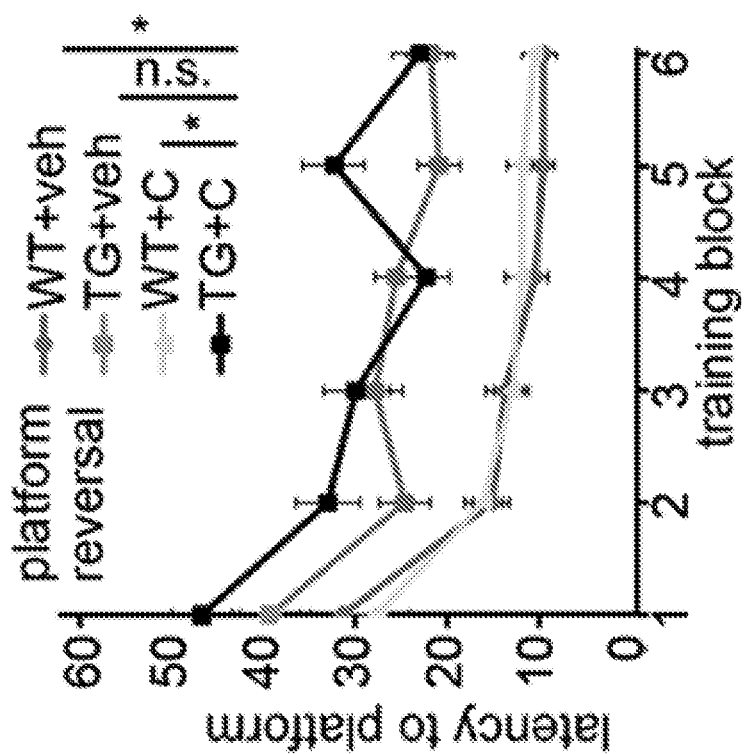
FIG. 20 is a line graph showing 100 mg/kg ceftazidime (as Fortaz® freshly solubilized at 333 mg/ml in sodium carbonate) or vehicle (veh) was administered by intraperitoneal (IP) injection BID for 6 weeks to 12-14 month-old wild type (WT) or APP/PS1 transgenic Alzheimer's model (TG) mice. Four weeks post-treatment initiation, spatial memory was assayed by Morris water maze (MWM) and plotted as the latency to locate a hidden platform. Data are mean+SEM of 10-12 mice/group. Performance was analyzed by two-way analysis of variance with RM-ANOVA over the last sixteen trials (four blocks) and showed a significant effect of genotype (*, P<0.05), but not of treatment in the set of training blocks post-platform relocation (reversal).

There is a possibility that fresh ceftazidime (as Fortaz®) might polymerize in vivo and be distributed from the periphery across the BBB. Intraperitoneal (IP) twice-daily (BID) administration of fresh non-polymerized ceftazidime (as Fortaz®) to APP/PS1 mice had no detectable effect on learning trials of spatial memory testing (FIG. 19, 20). Similarly, IP BID administration of aged 100 mg/kg Fortaz® containing pre-polymerized active Z did not rescue APP/PS1 mouse memory deficit (not shown). Thus, antagonism of PrP$^C$ and APP/PS1 behavioral deficits by Z requires central administration for efficacy.

Example 5

Acidic Polymers as Competitive Inhibitors of Aßo/PrP$^C$ Interaction

The activities of Z provide proof-of-principle that Aßo/PrP$^C$ interaction can be pharmaceutically targeted with non-biologic agents. Because inability to cross the BBB constrains the utility of a drug targeting AD, an expanded PLISA screen of 52,000 small molecules was conducted for Aßo/PrP$^C$ inhibitory activity in an effort to identify molecules with greater potential to transit the BBB, followed by extensive medicinal chemical optimization of 121 candidates. Although numerous activities were developed, none achieved an IC$_{50}$ below 1 µM, and thus were deemed insufficiently potent for development.

A polymeric degradation product of ceftazidime has been reported to possess anti-HIV activity (Hobi et al., 2001) with a hypothetical structure containing repeating acidic polar subunits (Baertschi et al., 1997; Ercanli and Boyd, 2006). This polymeric degradation product, referred to herein as "compound Z" or "Z" was purified from aged ceftazidime by either size exclusion or anion exchange chromatography, followed by replicated elemental analysis of each. Elemental analysis of Z did not conform precisely to the published predicted structure but does largely agree with an alternate structure when water and sodium adduct are assumed.

The chemical structure of parent compound of Z (the cephalosporin antibiotic ceftazidime) is:

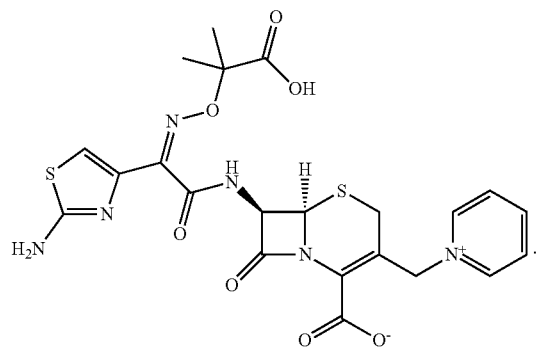 [SMILES: CC(C)(O/N=C(\C(=O)N[C@@H]1C(=O)N2C(C(=O)[O-])=C(C[n+]3ccccc3)CS[C@H]12)c1csc(N)n1)C(=O)O]

Elemental analysis was performed for compound Z purified from crude aged ceftazidime by size exclusion chromatography (SEC) or anion exchange chromatography (AIE). SEC and AIE elemental percentages matched closely, leading to the depicted formula and molecular weights (MW), assuming one or two sulfur constituents of prospective monomer. (FIG. 48).

Two prospective Z monomer subunit structures yield respective formulae and MW. As shown in FIG. 49, Structure 1 corresponds to previously published structure for the polymeric degradation product of ceftazidime; structure 2 corresponds to an alternative structure. The calculated MW of candidate 1, containing one sulfur and candidate 2, containing two sulfurs, do not correspond closely to the calculated MWs for formulae containing one or two sulfurs in (B).

The formulae for candidate 1 and 2, see FIG. 49, are calculated taking into account prospective water and sodium ion in the elemental analysis. The calculated MW of candidate 1 is substantially different (28.8%) from the monomer composition under these assumptions; the calculated MW of candidate 2 is substantially similar (4.4% difference) to the monomer composition taking into account water and sodium. Thus, candidate 2 is considered to be the likely structure of Z monomer. (FIG. 50).

Figure 21:
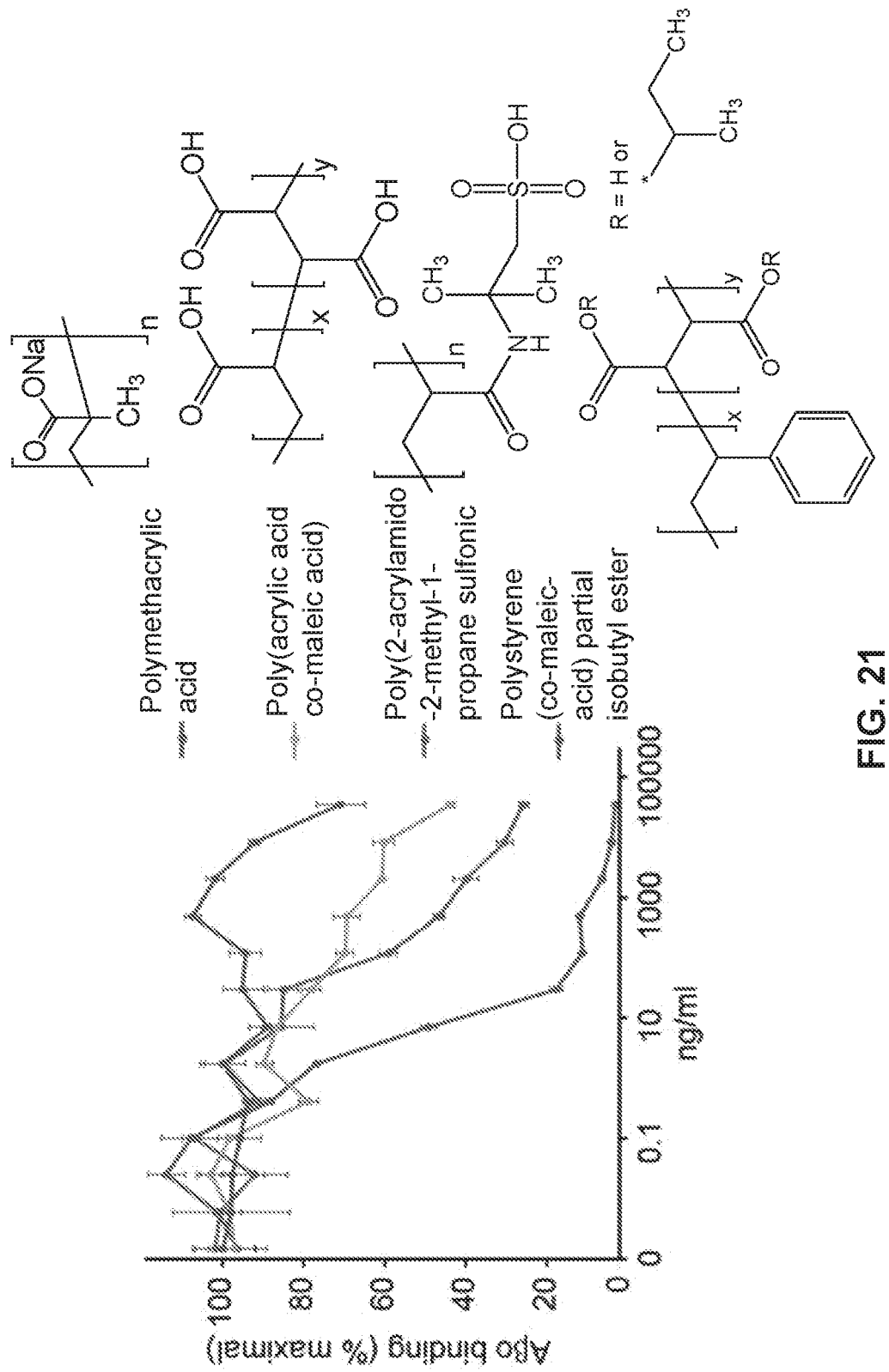
FIG. 21 is a line graph showing a series of anionic polymer activities were assayed by PLISA. Presence of the hydrophobic phenyl group in polar polystyrene co-maleic acid correlates with the high activity of the polymer. Data are mean+/−SEM, n=3 replicates per sample.
Figure 23:
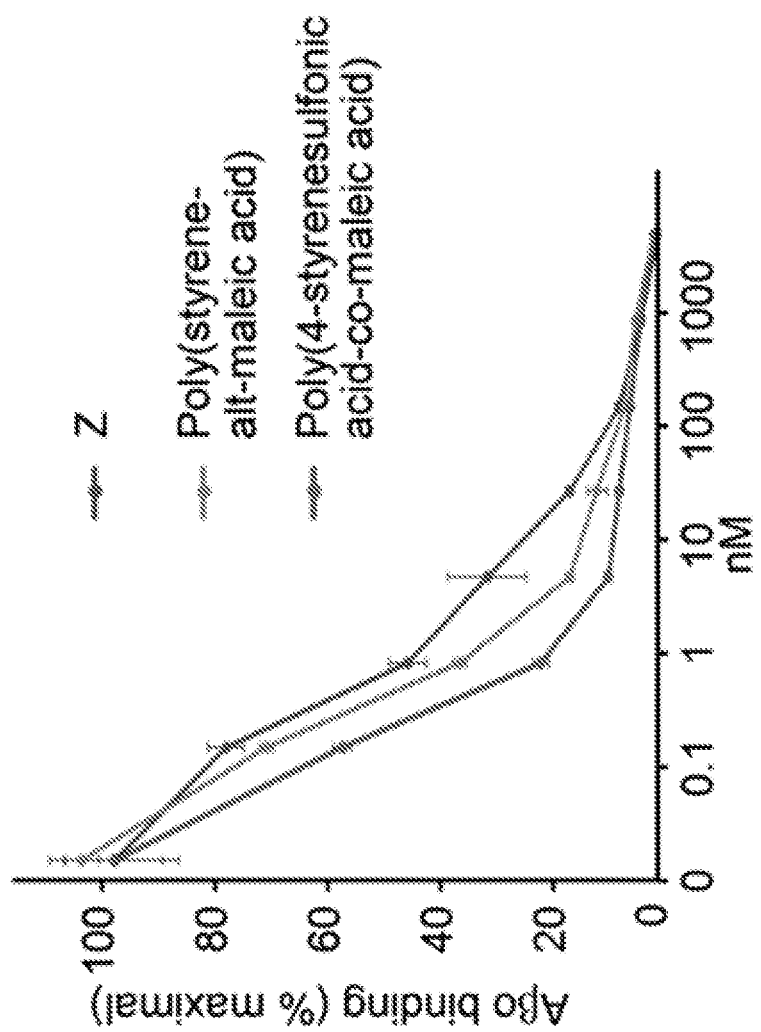
FIG. 23 is a line graph showing Aβo/PrP$^C$ inhibitory activity of selected anionic polymers exceed the activity of Z as assayed by PLISA. IC$_{50}$s=900 pM, 700 PM and 300 pM for Z, polystyrene co-maleic acid, and poly (4-styrenesulfonic acid-co-maleic acid) (PSCMA), respectively. Data are mean+/−SEM, n=3 replicates per sample.
Figure 24:
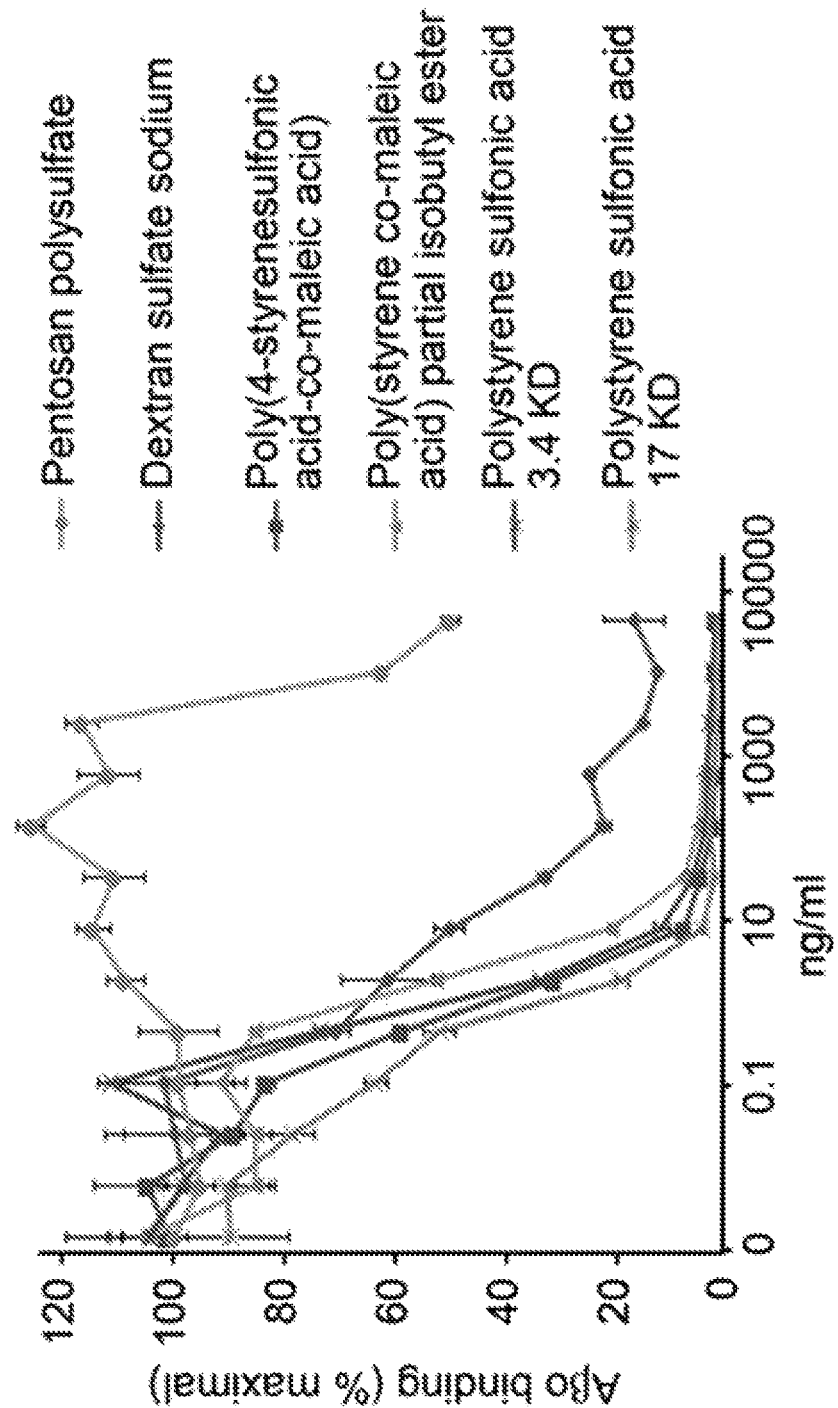
FIG. 24 is a line graph showing known PrP$^{Sc}$ inhibitors, pentosan polysulfate and dextran sulfate, exhibit much weaker PLISA activity than identified polar anionic polymers. Data are mean+/−SEM, n=3 replicates per sample.

Both potential structures of Z allow for repeating acidic polar subunits. Based on these general features, structurally related polymers were tested to derive a structure-activity relationship (SAR) for polymer activity. Simple polyanionic structures, such as polyacrylic acid co-maleic acid, were minimally inhibitory, while the inclusion of a hydrophobic moiety, such as in poly (styrene co-maleic acid) partial isobutyl ester, dramatically increased Aßo/PrP$^C$ inhibitory activity (FIG. 21). A range of polymers featuring acidic groups proximal to cyclic hydrophobic groups exhibit low nM activity, comparable or superior to Z (FIG. 22-24 and Table A), indicating that polar acidic/hydrophobic polymers are selectively active against PrP$^C$.

TABLE A

| Polymer | MW (Da) | IC$_{50}$ (nM) |
|---|---|---|
| Polyethylene glycol | 35000 | >10000 |
| Poly( acrylic acid) sodium salt | 5100 | >10000 |
| Poly(methacrylic acid) sodium salt | 5400 | >10000 |
| Poly( acrylic acid co-maleic acid) soln | 3000 | 10000 |
| Pentosan polysulfate sodium | 5000 | 7000 |
| Poly-d-glutamic acid sodium salt | 30000 | >1000 |
| Dextran sulfate sodium salt | 8000 | 6 |
| Polystyrene sulfonic acid sodium salt | 3400 | 6 |
| Melanin | 20000 | 5 |
| Neuromelanin (norepinephrine monor equivalent) | 0.169 | 19 |
| Poly (styrene-co-maleic acid) partial isobutyl ester | 65000 | 5 |
| Compound Z | 15000 | 0.9 |
| Polystyrene sulfonic acid sodium salt | 17000 | 0.9 |
| Poly (2-acrylamido-2-methyl-1-propanesulfonic acid) | 2000000 | 0.9 |
| Poly (styrene-alt-maleic acid) sodium salt soln | 350000 | 0.8 |
| Poly(4-styrenesulfonic acid-co-maleic acid) sodium salt | 20000 | 0.3 |

Figure 22:
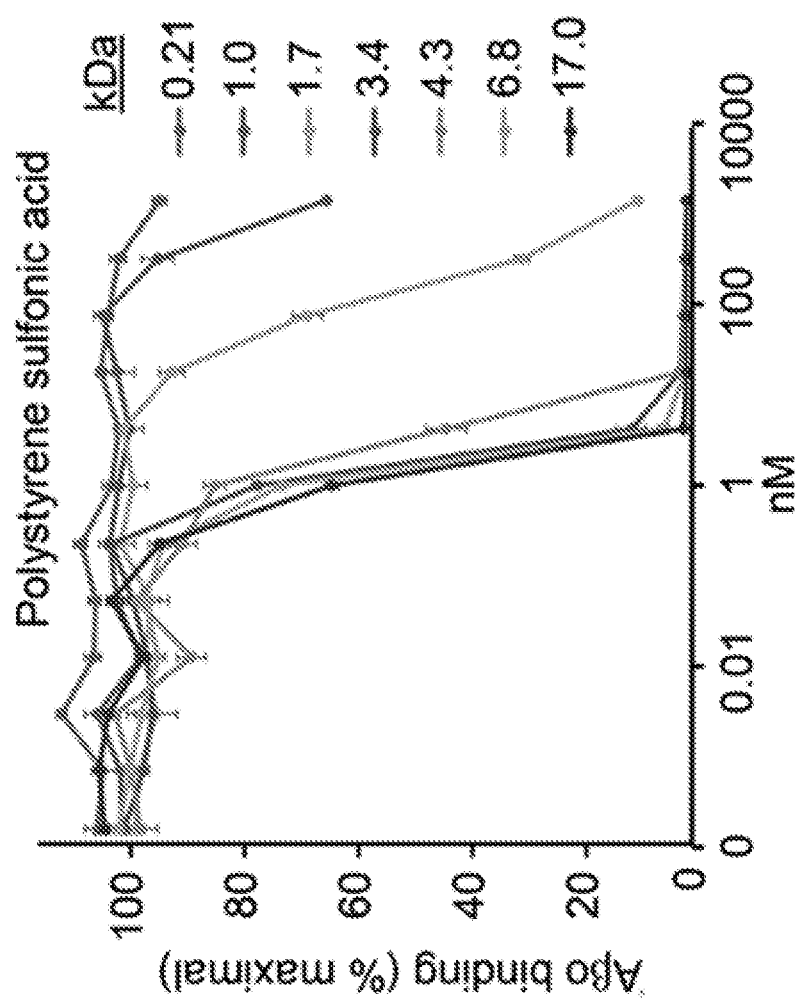
FIG. 22 is a line graph showing size-dependence of Aβo/PrP$^C$ inhibitory activity was assayed by PLISA, using polystyrene sulfonate polymers of specific average lengths. Activity positively correlated with size up to 3.4 kDa, when an IC$_{50}$ plateau of approximately 5 nM was reached. Data are mean+/−SEM, n=3 replicates per sample.

The efficacy of specific polymers contrasts with the inability to derive high-affinity small molecule inhibitors and suggests a minimum size limitation to potency. PLISA evaluation of specific molecular weights of polystyrene sulfonate (PSS) indicates roughly equivalent 1-10 nM IC$_{50}$ for species of 17 kDa, 6.8 kDa and 4.3 kDa, with potency decreasing dramatically at 1.7 kDa or smaller (FIG. 22). Without being bound by any theory, this inhibitor size threshold may relate to the minimum dimension required for simultaneous contact with both Aßo-binding domains at PrP 23-31 and 90-111, either intramolecularly or intermolecularly. Confirmation of this proposition awaits structural characterization.

Figure 25:
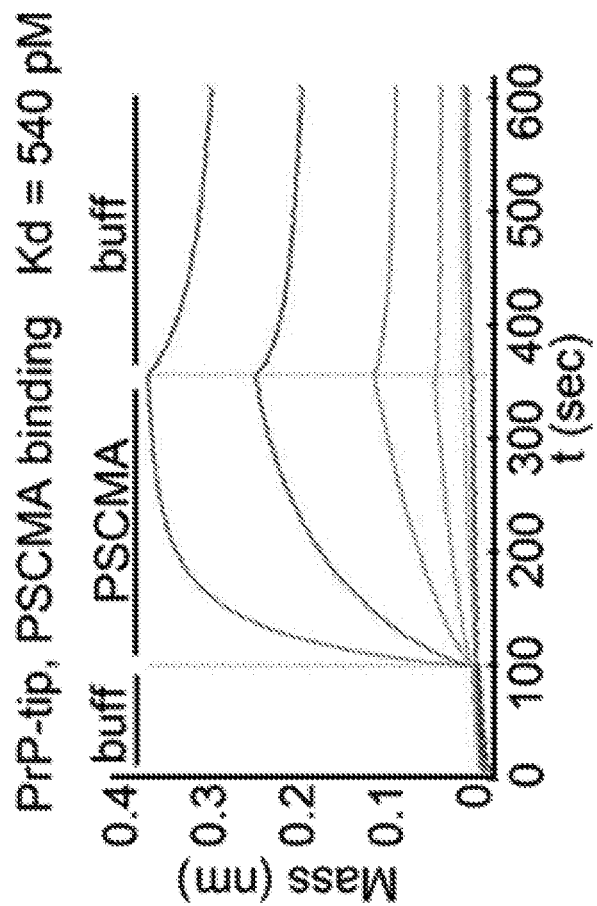
FIG. 25 is a line graph showing biolayer interferometric measurement of PSCMA binding to PrP$^C$-coated sensor tip. Association (100-360 sec) and dissociation (360-600 sec) traces of 3.4 kDa PSCMA in four-fold dilution steps from 1 µM top concentration, indicated a dissociation constant of 540 pM.
Figure 26:
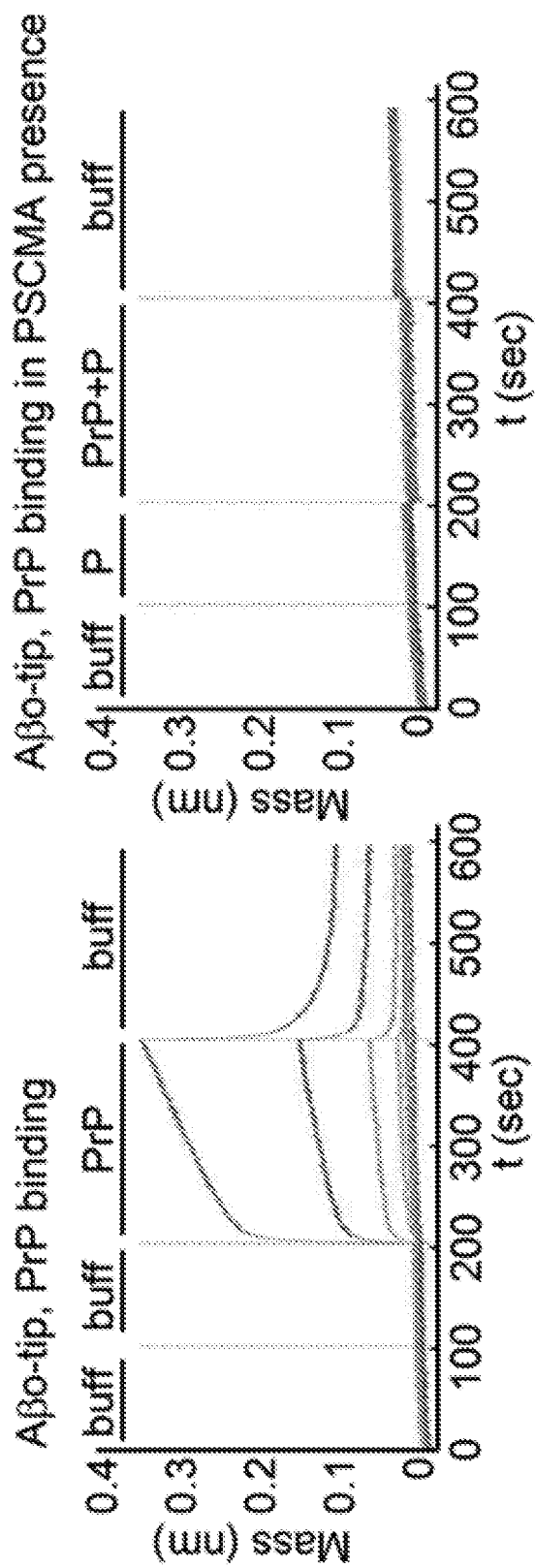
FIG. 26 is two sensograms showing a biolayer interferometric measurement of soluble full-length PrP$^C$ binding to Aβo-coated sensor tip in assay buffer alone (left sensorgram) or in the presence of PSCMA (P) (right sensorgram). Association (200-400 sec) and dissociation (400-600 sec) traces of PrP$^C$ in four-fold dilution steps from 500 nM top concentration, are completely inhibited by PSCMA (1 µM). PSCMA exhibits no affinity for Aβo (100-200 sec, right sensorgram) indicating clear specificity for PrP as a binding target.

PSCMA directly binds PrP$^C$, with an observed K$_D$ of 540 PM by BLI (FIG. 25). Concordantly, PSCMA affinity for Aßo is undetectable by BLI and, when co-applied with full-length PrP$^C$ in solution, completely blocks PrP$^C$ binding to an Aßo-coated BLI sensor (FIG. 26).

Figure 27:
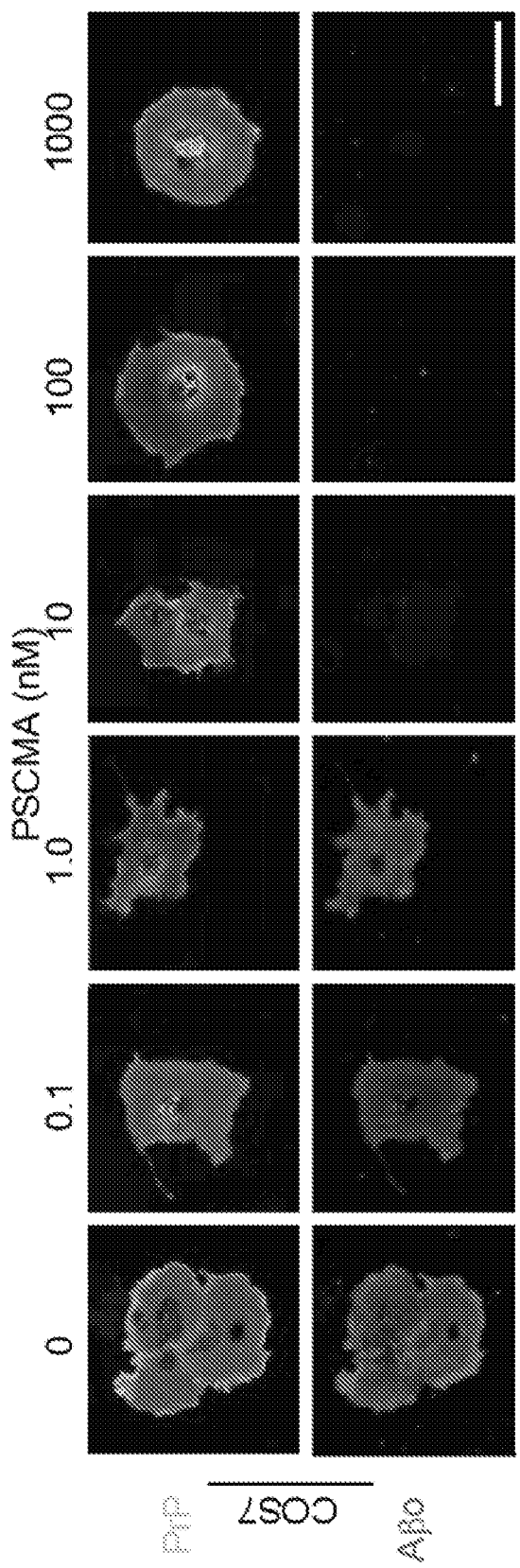
FIG. 27 is eight images showing PrP$^C$-transfected COS7 cells treated with the designated concentrations of PSCMA for 30 min at RT, followed by addition of 1.0 µM (monomer equivalent) biotinylated Aβo for 1 h, fixation and staining of PrP$^C$ and biotin, and quantified with ImageJ. Scale bar=10 µm.
Figure 28:
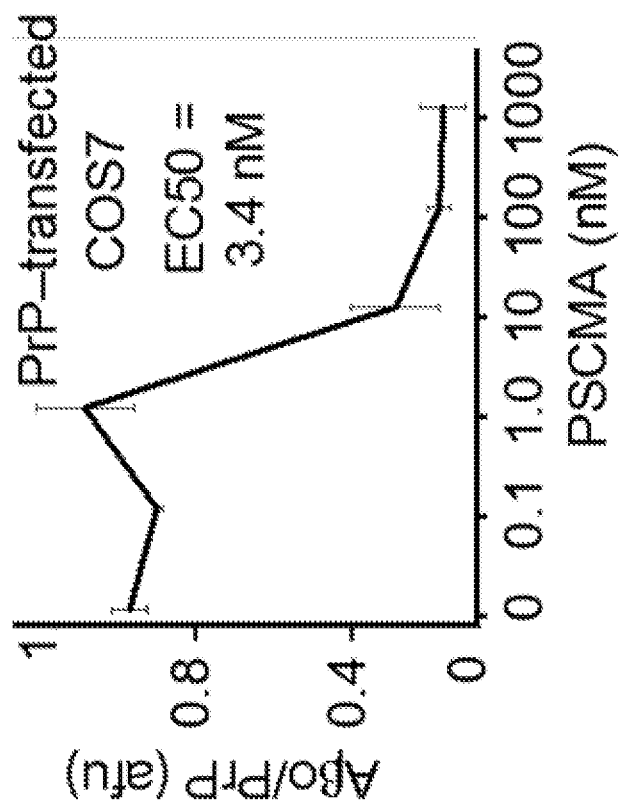
FIG. 28 is a line graph showing ImageJ quantification of Aβo signal for individual PrP-transfected cells in FIG. 29, expressed as the ratio of Aβo signal to PrP immunoreactivity. A PSCMA IC50 of 3.4 nM is indicated. n=3 wells per condition, 10 randomly selected cells per well. Data are mean+/−SEM.

Next, the activity of 3.4 kDa PSS or 17 kDa PSCMA was evaluated in cellular assays. Soluble Aßo interaction with cell membrane-associated PrP$^C$ is blocked by PSCMA with an IC$_{50}$ of 3.4 nM in PrP$^C$-transfected COS cells (FIG. 27)

and 24 nM in primary rat cortical neurons with endogenously expressed $PrP^C$ (FIG. 28).

Figure 29:
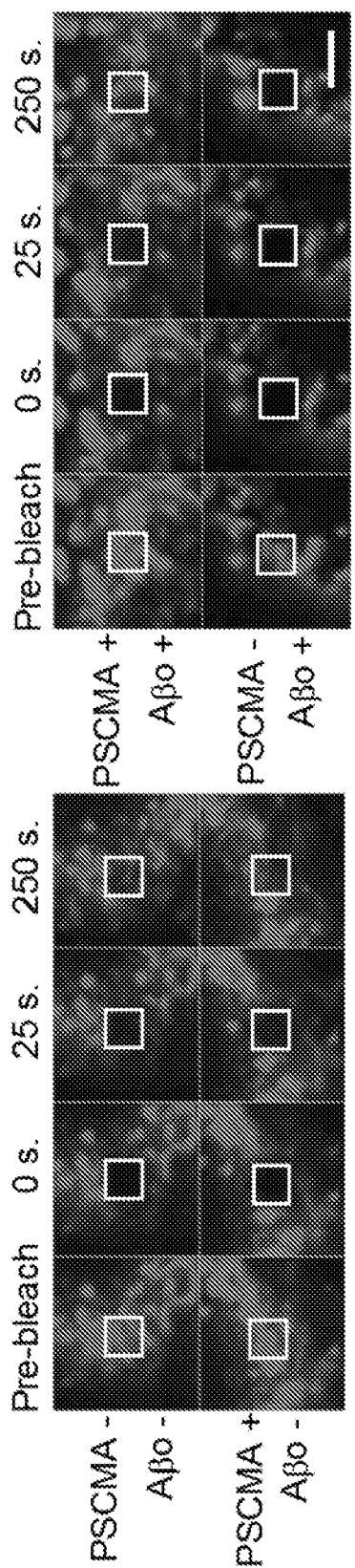
FIG. 29 is two panels of eight images each showing SNAP-tagged PrP$^C$-transfected COS7 cells treated with SNAP-Surface Alexa Fluor647 to fluorescently label cell-surface PrP. Cells were treated with vehicle 1 hr, 1.0 µM Aβo for 1 hr, 1.0 µM PSCMA for 1 hr., or PSCMA for 15 min. followed by Aβo for 1.0 hr. A 50 µM$^2$ square of fluorescent PrP was bleached with a burst of laser light, and recovery of PrP into the bleached area through lateral PrP diffusion in the plasma membrane monitored over 250 seconds. Scale bar=1 µM.
Figure 30:
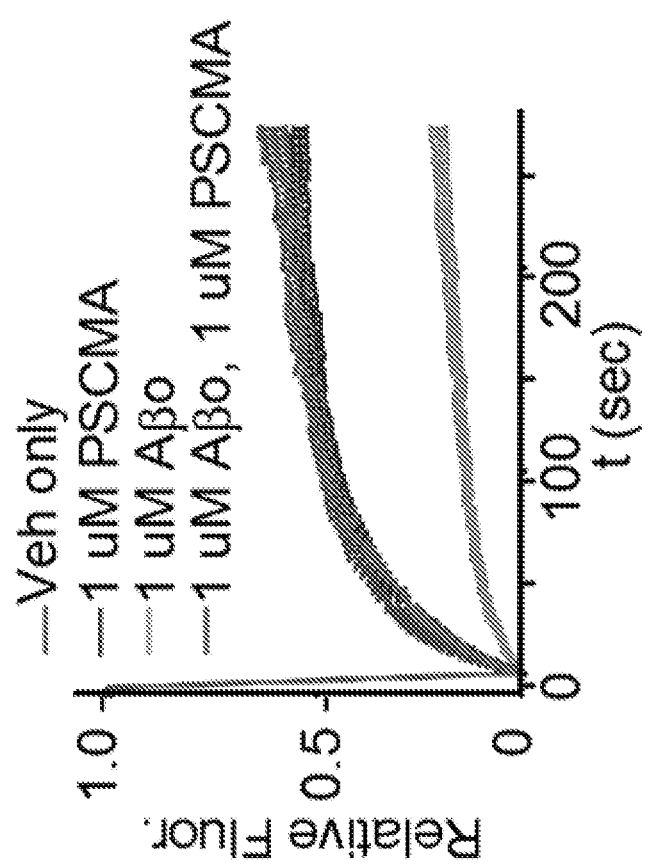
FIG. 30 is a line graph showing quantification of recovery in (C). Vehicle and PSCMA treatment fluorescence recovery curves were indistinguishable. Aβo treatment strongly inhibited PrP recovery kinetics, indicating arrested lateral mobility of PrP in the plasma membrane as a result of Aβo/PrP$^C$ complexation. PSCMA pre-treatment completely prevented Aβo-induced inhibition PrP recovery kinetics.

Upon binding of Aβo, the lateral movement of $PrP^C$ within the plasma membrane is greatly reduced as monitored by Fluorescence Recovery After Photobleaching (FRAP), with a shift from rapid to slow recovery from photobleaching. To investigate the ability of PSCMA to block Aβo-triggered immobilization of $PrP^C$ in a hydrogel with Aβo, a set of FRAP experiments in COS7 cells transiently transfected with a human PrP/N-terminus SNAP tag fusion construct was performed, enabling specific fluorescent labeling of $PrP^C$ on the cell surface. In these cells, cell-surface SNAP-Alexa Fluor647-$PrP^C$ exhibits rapid lateral translation within the plasma membrane, as indicated by recovery of fluorescent signal within the laser-bleached zone over 250 seconds. Treatment with 1 μM PSCMA had no measurable effect upon the kinetics of FRAP compared with vehicle control (FIG. 29, 30). PSCMA pre-treatment completely blocked the $PrP^C$ immobilizing action of Aβo treatment (FIG. 29, 30).

Figure 31:
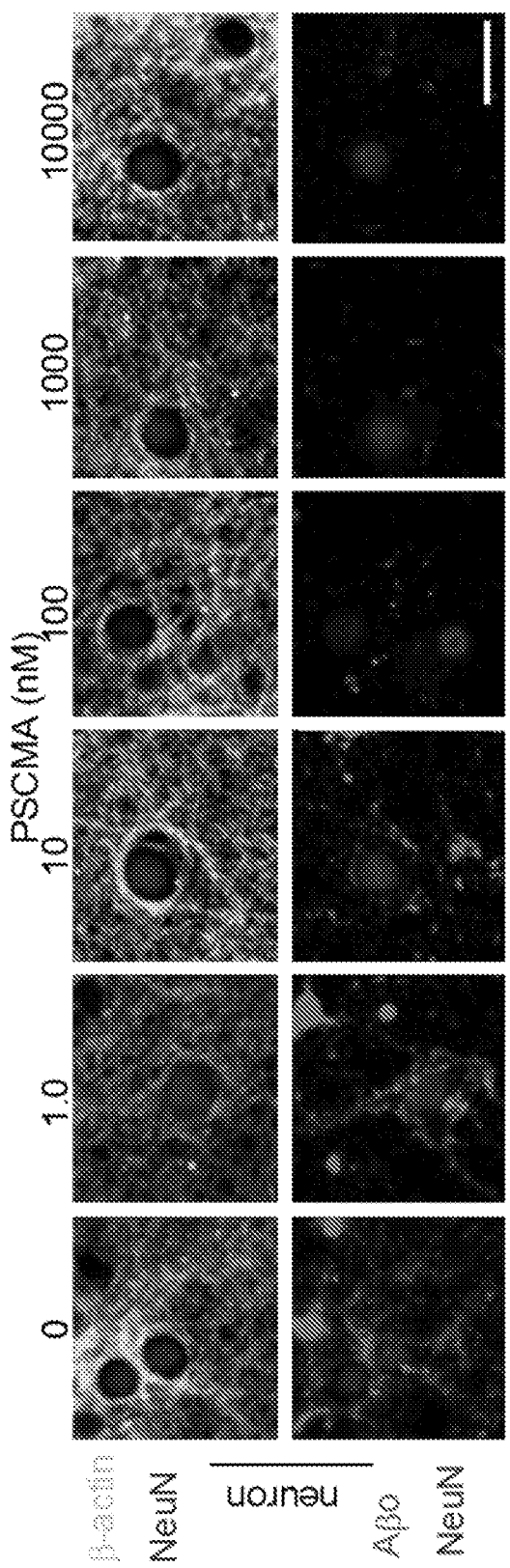
FIG. 31 is twelve images showing 21 DIV rat neurons treated with the designated concentrations of PSCMA for 30 min at RT, followed by addition of 1.0 µM (monomer equivalent) biotinylated Aßo for 1 hr, fixation and staining of NeuN, actin and biotin, and quantified with ImageJ. Scale bar=10 µm.
Figure 32:
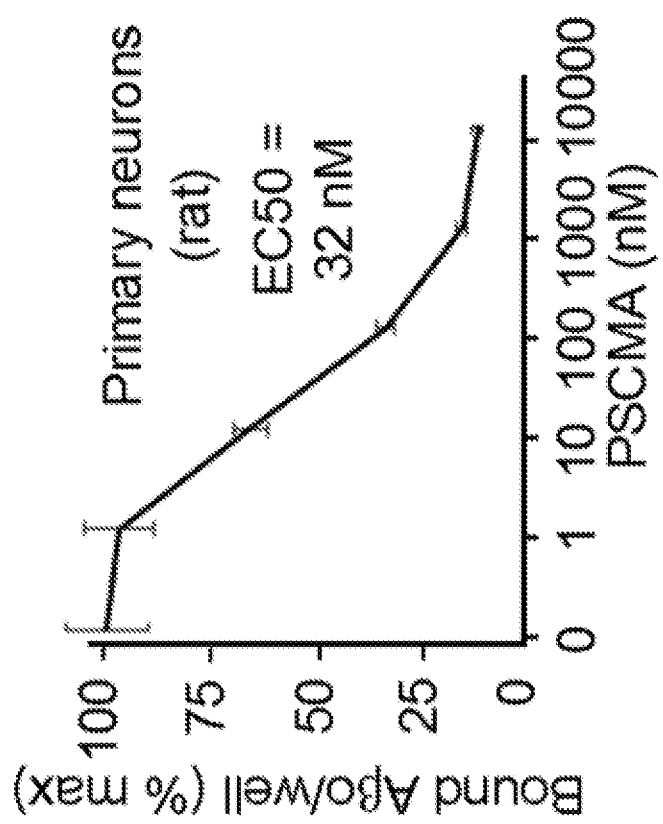
FIG. 32 is a line graph showing ImageJ quantification of wells in FIG. 31, expressed as total Aßo signal per well. The PSCMA $IC_{50}$ of 32 nM is indicated. n=3 wells per condition. Data are mean+/−SEM.
Figure 33:
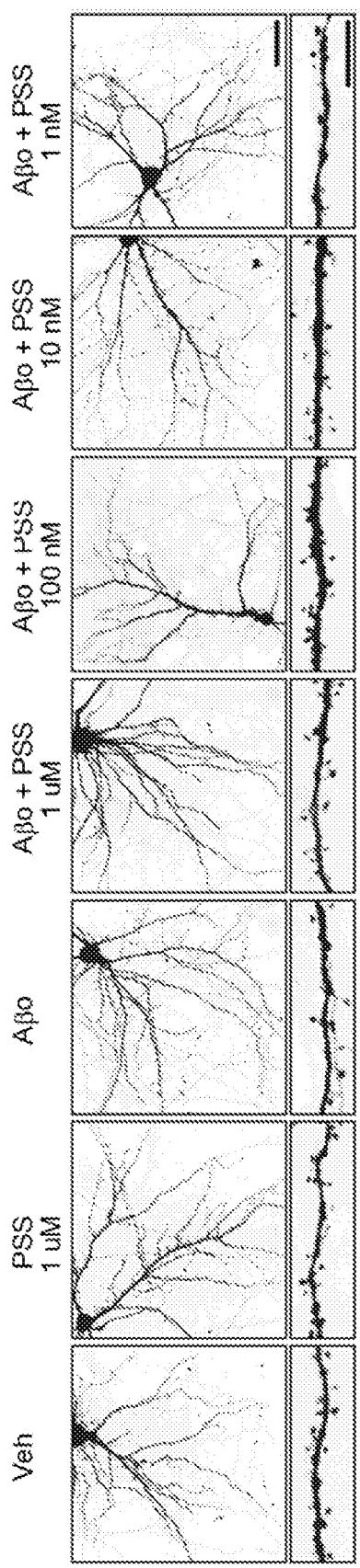
FIG. 33 is seven images showing 14 DIV mouse hippocampal neurons treated 4 days with vehicle or Aßo (1 µM)+/−the designated concentrations of polystyrene sulfonate (PSS). Scale bar=15 µm (top), 5 µm (bottom). Aßo induced a consistent reduction in spine density per µm dendrite length.
Figure 34:
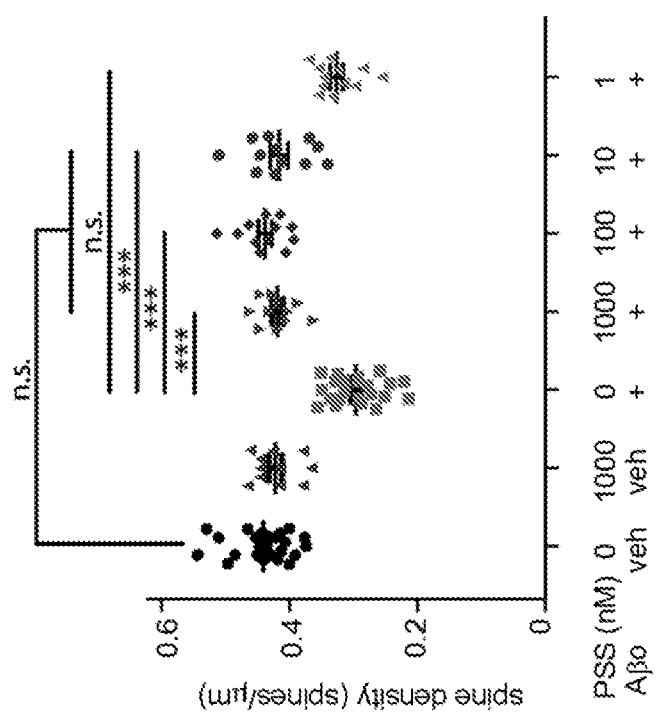
FIG. 34 is a scatter graph showing quantitation of dendritic spine density from experiments in FIG. 33. Co-administered PSS blocked Aßo action dose-dependently with an IC50 between 1-10 nM. n=3 dendrites per neuron, 5-7 neurons per coverslip, 4-8 coverslips per condition. Data are mean+/−SEM (***, P<0.001), one-way ANOVA with Dunnett's comparison.
Figure 34A:
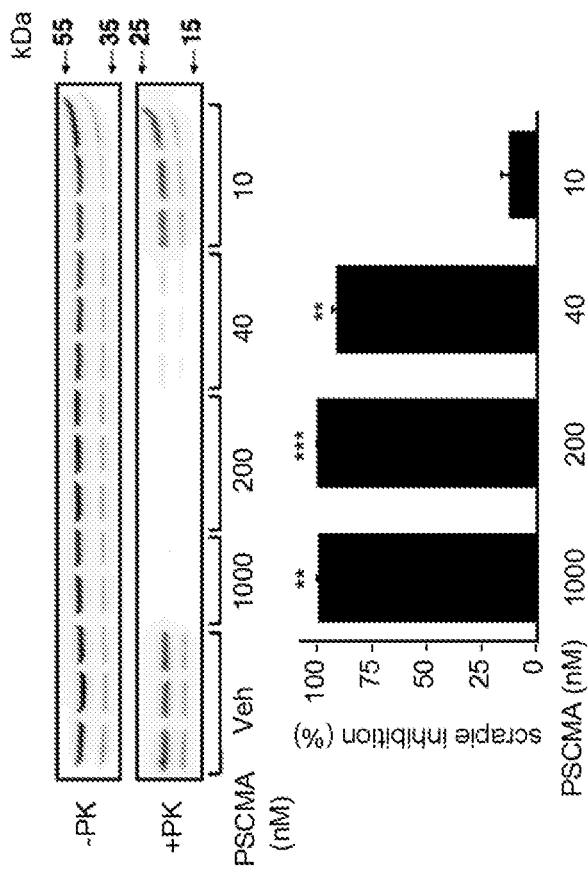
FIG. 34A is two images and a bar graph showing propagation of proteinase K-resistant $PrP^{Sc}$ prion in N2a cell culture is blocked by 48 hr application of PSCMA, with an EC50 between 10-40 nM, as revealed by $PrP^C$ immunoblot. Data are mean band densitometry+/−SEM, n=3 replicates per condition. (, P<0.01; *, P<0.001), one-way ANOVA with Tukey's corrected pairwise comparisons.

The $PrP^C$-mediated synaptotoxic action of Aβo was characterized in vitro in an Aβo-induced neuronal spine loss assay. PSS acts similarly to Z, inhibiting spine loss dose-dependently with an $IC_{50}$ between 1-10 nM (FIG. 31), closely matching its Aβo/$PrP^C$ inhibitory activity by PLISA (FIG. 22). Also paralleling Z, PSCMA exhibits pronounced activity in an N2A cell $PrP^{Sc}$ propagation assay, with an $IC_{50}$ between 10-40 nM. Thus, a common characteristic among pharmacologically active acidic polymers appears to be efficacy against both AD and TSE cellular pathophysiologies.

Example 6

Figure 35:
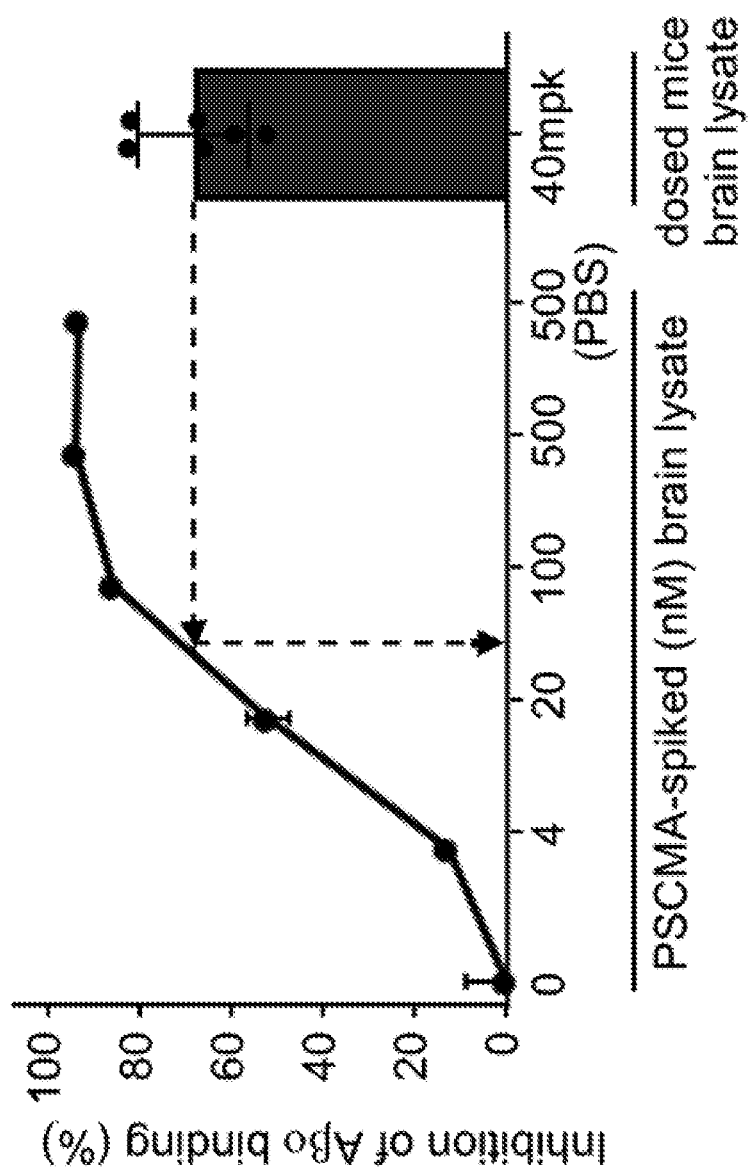
FIG. 35 is graph showing WT mice administered 40 mg/kg (mpk) PCMA by oral gavage BID for 10 days, followed by perfusion, brain lysis, extraction and PLISA assessment of Aßo/$PrP^C$ inhibitory activity. Data are mean+/−SEM, n=6 mice. Standard curve was made by spiking brain lysate from untreated mice with the designated concentrations of PSCMA, prior to identical processing as brains from treated mice. Orally-dosed mouse brain contains an average 40 nM PSCMA. Data are mean+/−SEM, n=3 replicates per sample.

Peripherally Administered PSCMA Enters the Brain and Rescues APP/PS1 AD Model Mice The ideal $PrP^C$ antagonist would be orally bioavailable and cross the BBB. High-affinity macromolecules (antibodies) targeting $PrP^C$ have been peripherally administered and shown to penetrate the brain at sufficient concentration to rescue model mice from AD behavioral and histo-pathology (Chung et al., 2010; Freir et al., 2011; Klyubin et al., 2014). Since the polymers with low nanomolar affinities, comparable to anti-$PrP^C$ antibodies, the ability of orally-administered PSCMA to reach the brain at $PrP^C$-inhibitory concentrations was explored. Adult wild type mice were treated by oral gavage with 20 kDa average PSCMA, followed by assessment of brain lysate for the presence of Aβo/$PrP^C$ inhibitory activity. Twice daily administration of 40 mg/kg for 10 days yielded brain bioactivity equivalent to about 40 nM PSCMA concentration (FIG. 35). Although this represents only ~2% of the 2 μM concentration expected from a single dose of a perfectly bioavailable compound, it is far above the PSCMA/$PrP^C$ $K_D$ of 540 PM and sufficiently high to evaluate in a disease model.

Figure 40:
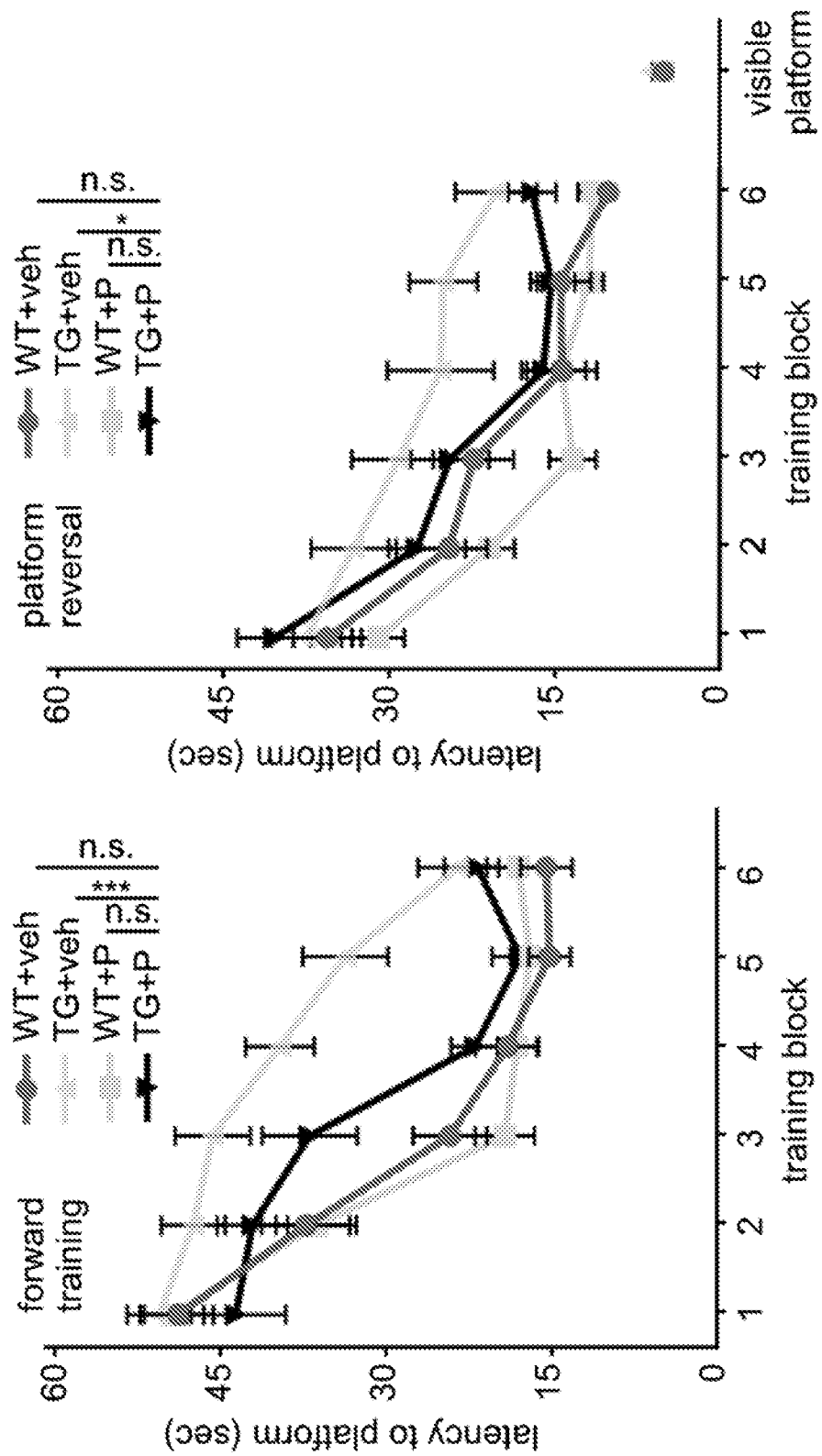
FIG. 40 is two line graphs showing that PSCMA-treated APP/PS1 mice are rescued from learning and memory deficits. After treating for four weeks BID by oral gavage with PSCMA, mice were evaluated for memory performance by Morris water maze. Latency to find the hidden platform is plotted as a function of trial block number. Statistical differences between groups are indicated in the Fig. Data are mean+/−SEM (*, P<0.05; ***, P<0.001). Two-way repeated measures ANOVA comparing each group to the transgenic group treated with PSCMA, with Dunnett's correction for multiple comparisons.
Figure 41:
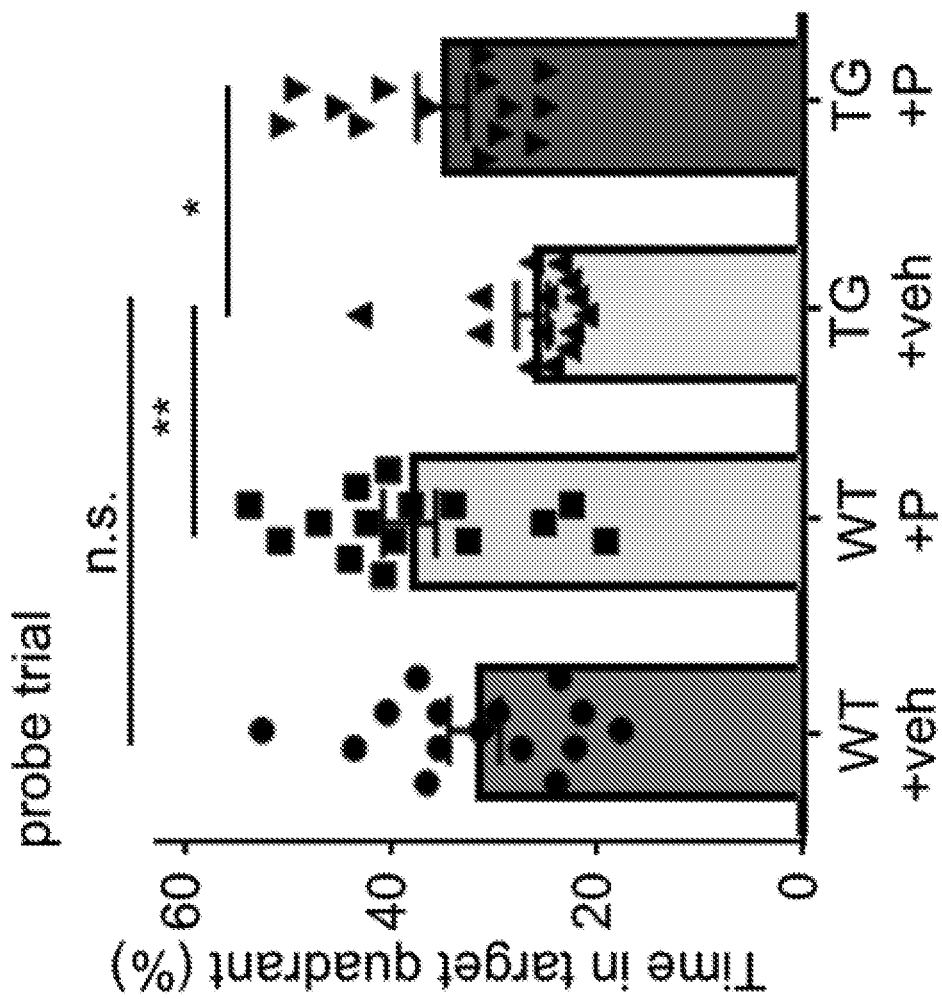
FIG. 41 is a bar graph showing that for the probe trial, percent time spent in the target quadrant after platform removal is indicated. Vehicle-treated transgenic animals spent significantly less time in the target quadrant compared to either drug-treated WT animals or drug-treated transgenic animals. Data are mean+/−SEM (*, P<0.05; **, P<0.01). One-way ANOVA with Dunnett's comparing to APP/PS1, Veh.
Figure 42:
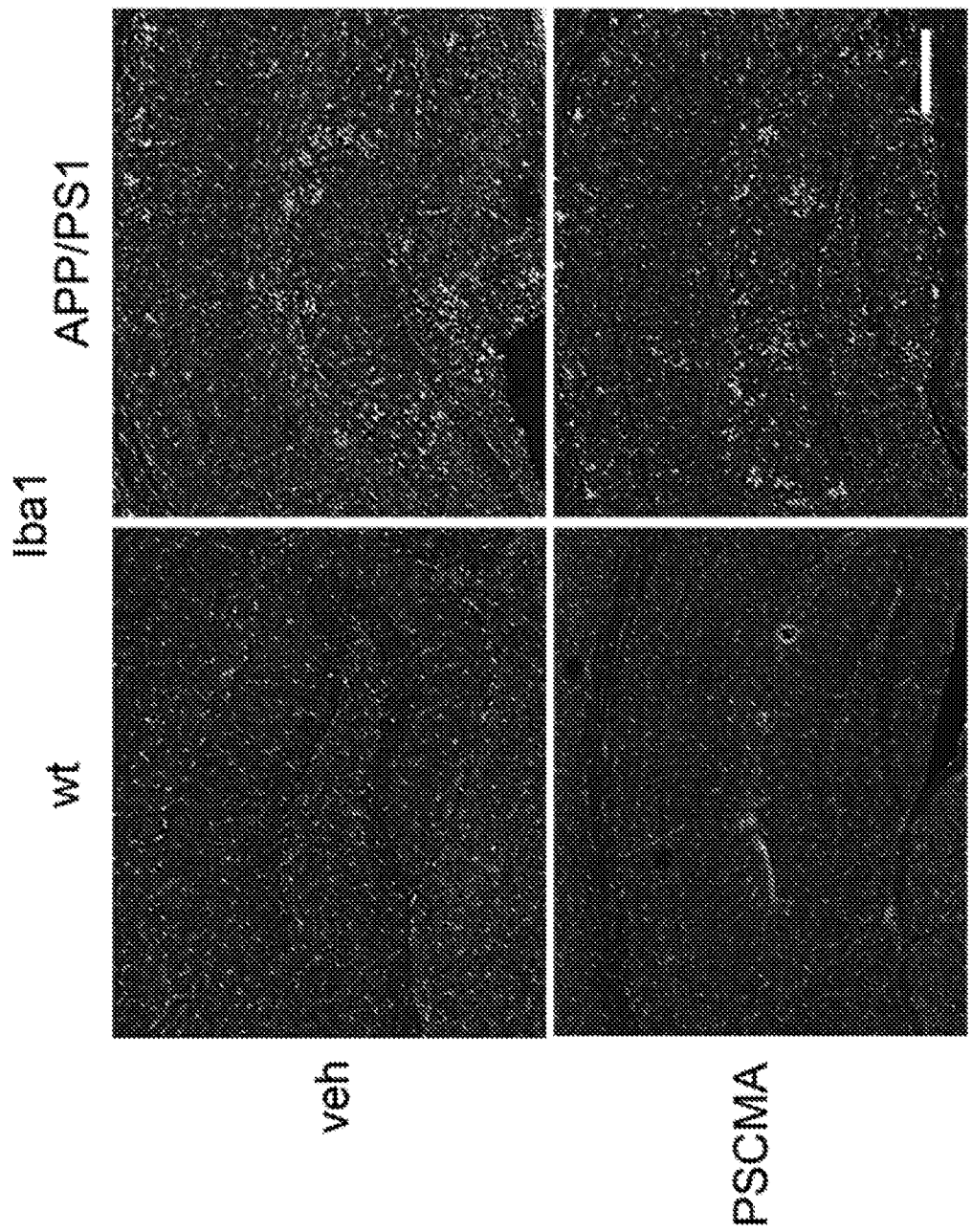
FIG. 42 is a panel of four images showing hippocampi stained with an antibody for the activated microglia marker Iba1 exhibit increased area occupied by immunoreactive puncta in APP/PS1 vs WT mice. Neither WT or APP/PS1 exhibit an effect of oral PSCMA treatment on Iba1 immunoreactive puncta. Scale bar=50 µm.
Figure 43:
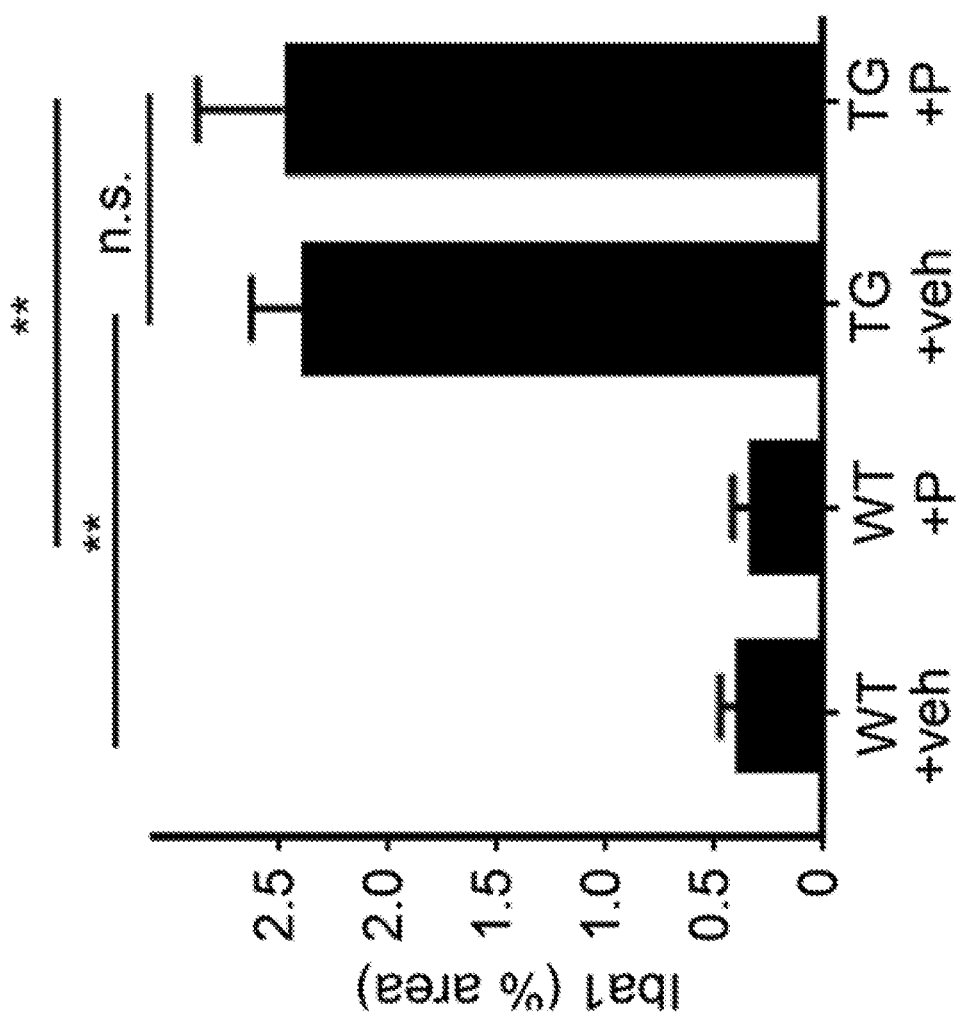
FIG. 43 is a bar graph showing quantitation of hippocampal area immunopositive for Iba1 puncta. A statistically significant eight-fold increase in Iba1 expression in APP/PS1 compared to WT is unaltered compared to APP/PS1 treated with PSCMA, indicating a lack of effect of PSCMA on microglial neuroinflammation. Data are mean+/−SEM, n=6 mice, average 2 images/mouse. (**, P<0.01 by one-way ANOVA with Tukey's post hoc multiple comparisons test).
Figure 44:
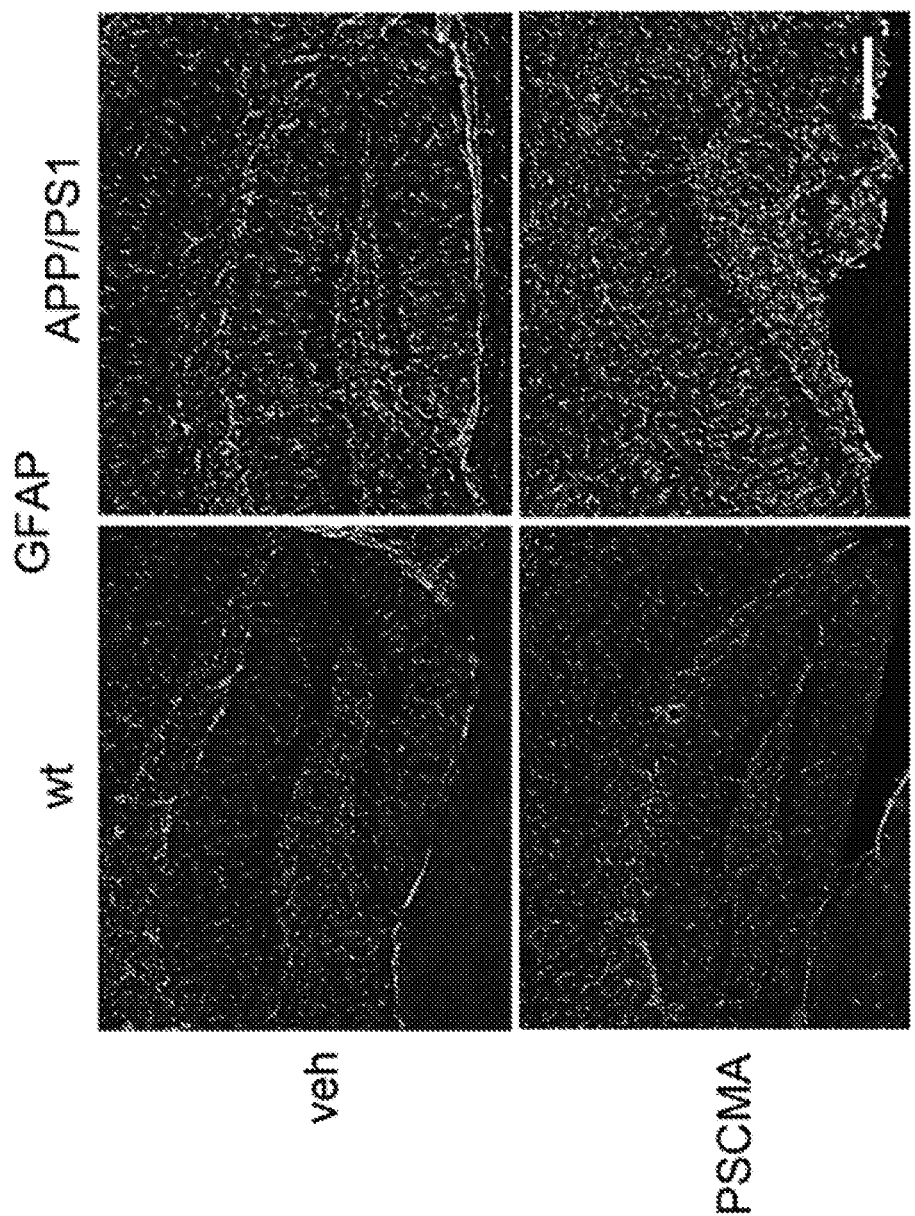
FIG. 44 is a panel of four images showing hippocampi stained with an antibody for the activated astrocyte marker GFAP exhibit increased area occupied by immunoreactive puncta in APP/PS1 vs WT mice. Neither WT or APP/PS1 exhibit an effect of oral PSCMA treatment on GFAP immunoreactive puncta. Scale bar=50 µm.
Figure 45:
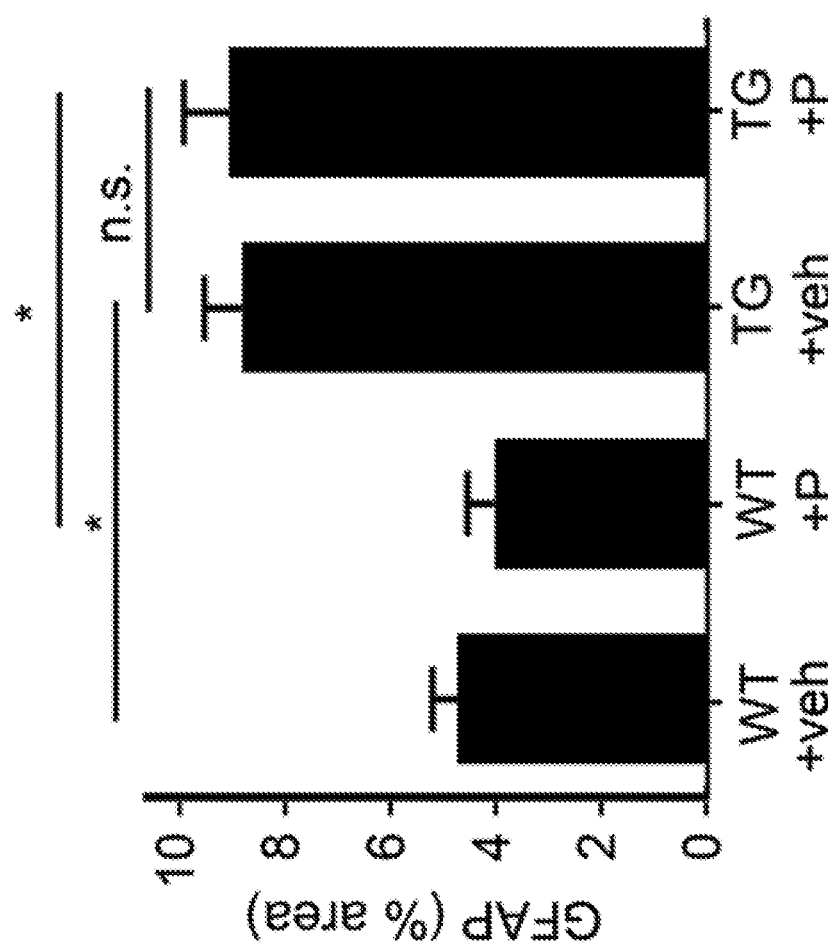
FIG. 45 is a bar graph showing quantitation of hippocampal area immunopositive for Iba1 puncta. A statistically significant two-fold increase in GFAP expression in APP/PS1 compared to WT is unaltered compared to APP/PS1 treated with PSCMA, indicating a lack of effect of PSCMA on astrocytic neuroinflammation. Data are mean+/−SEM, n=6 mice, average of 2 images/mouse. (**, P<0.01 by one-way ANOVA with Tukey's post hoc multiple comparisons test).
Figure 46:
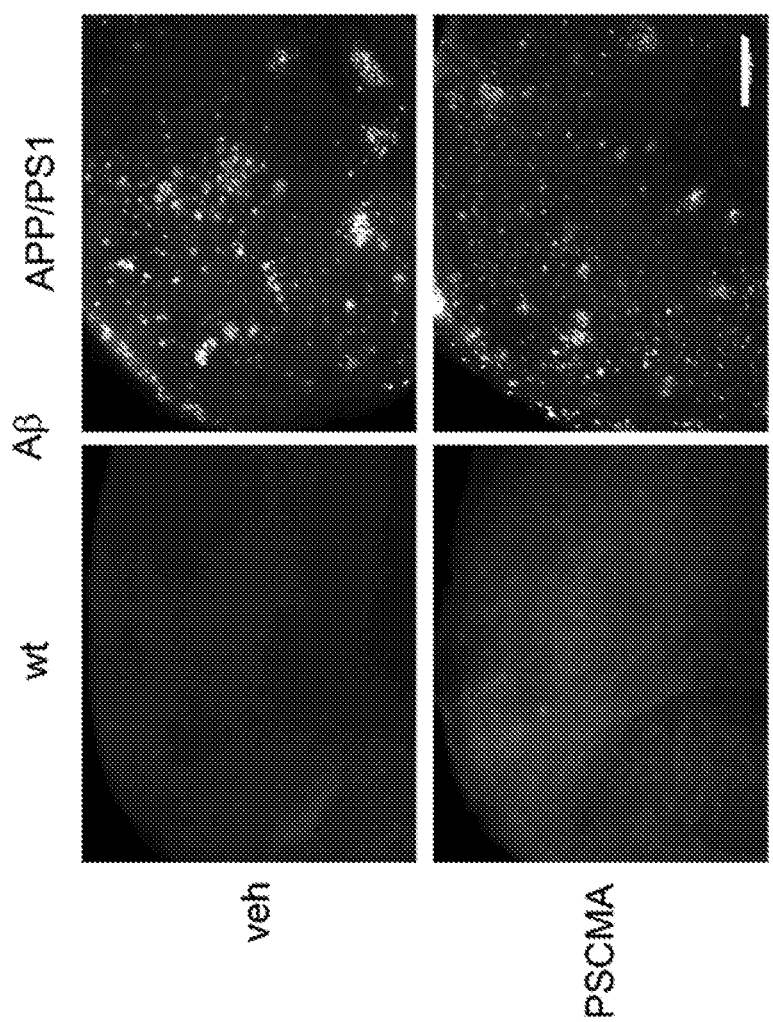
FIG. 46 is a panel of four images of cortical sections stained with thioflavin S exhibiting increased area occupied by Aß plaque load in APP/PS1 vs WT mice. Neither WT or APP/PS1 exhibit an effect of oral PSCMA treatment on Aß plaque load. Scale bar=500 µm.
Figure 47:
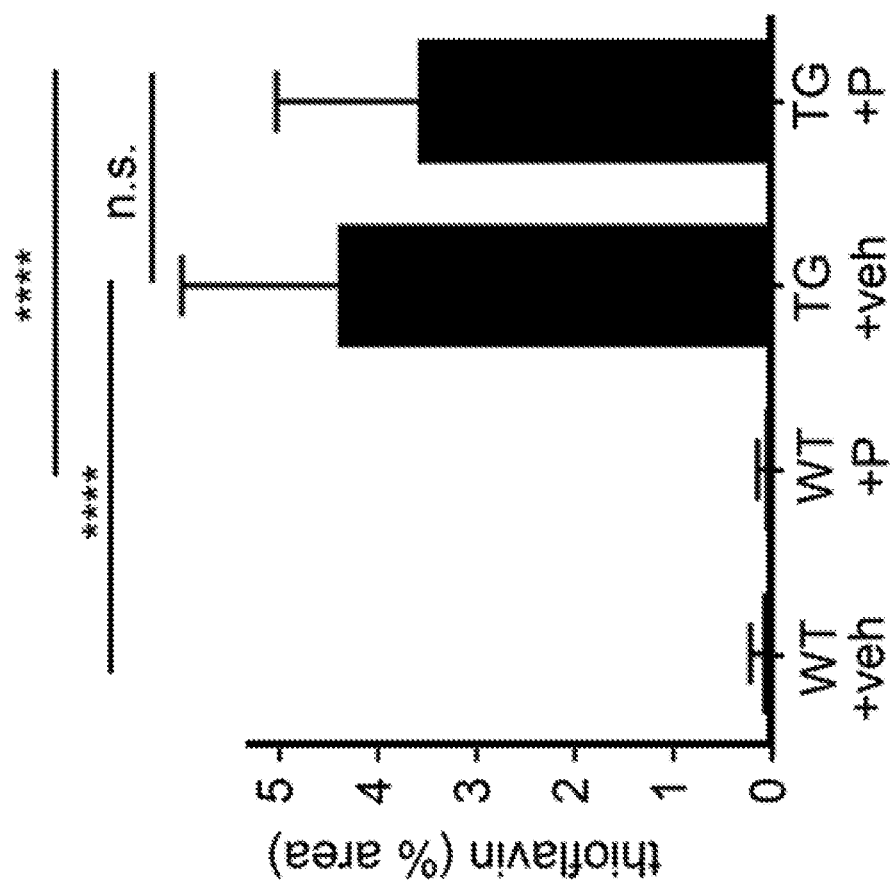
FIG. 47 is a bar graph showing quantitation of cortical area positive for thioflavin S detection of Aß plaque. A statistically significant increase in thioflavin S signal in APP/PS1 compared to WT is unaltered compared to APP/PS1 treated with PSCMA, indicating a lack of effect of PSCMA on Aß plaque load. Data are mean+/−SEM, n=6 mice, average of 2 images/mouse. (****, P<0.0001 by one-way ANOVA with Dunnett's multiple comparisons test).

To achieve estimated concentrations in the brain at a 10-fold excess over the PSCMA/PrP $K_D$, 3 mg/kg PSCMA twice daily (BID) by oral gavage to APP/PS1 mice for 30 days, followed by MWM spatial memory testing was administered. Treatment began at 12 months of age, after Aβ accumulation, synapse loss and learning/memory deficits are well established in this strain housed in our facility (Gimbel et al., 2010; Haas et al., 2016; Kaufman et al., 2015; Kostylev et al., 2015; Salazar et al., 2017; Um et al., 2013). This provides a therapeutic disease-modifying regime rather than a prophylactic experimental design. Mice remained on treatment throughput testing and were examined histologically after behavioral analysis (FIG. 36-41). Transgene-dependent behavioral impairment was evidenced by increased average swim latency to the hidden platform by APP/PS1 mice compared to age-, weight-, and sex-matched WT mice (FIG. 40). Oral PSCMA administration rescued mice from pre-existing phenotypic learning and memory impairment, as evidenced by a return of APP/PS1 swim latency to a duration indistinguishable from WT, in both forward trials (FIG. 40) and training trials performed after reversal of the submerged platform (FIG. 40). One day after the final learning swim, a probe trial in the absence of the hidden platform was conducted to test memory for the learned location. The APP/PS1 mice treated with vehicle spent significantly less time in the target quadrant than did APP/PS1 or WT mice treated with PSCMA (FIG. 41), indicating that PSCMA treatment corrected a pre-existing learning and memory deficit in the APP/PS1 mice.

Figure 36:
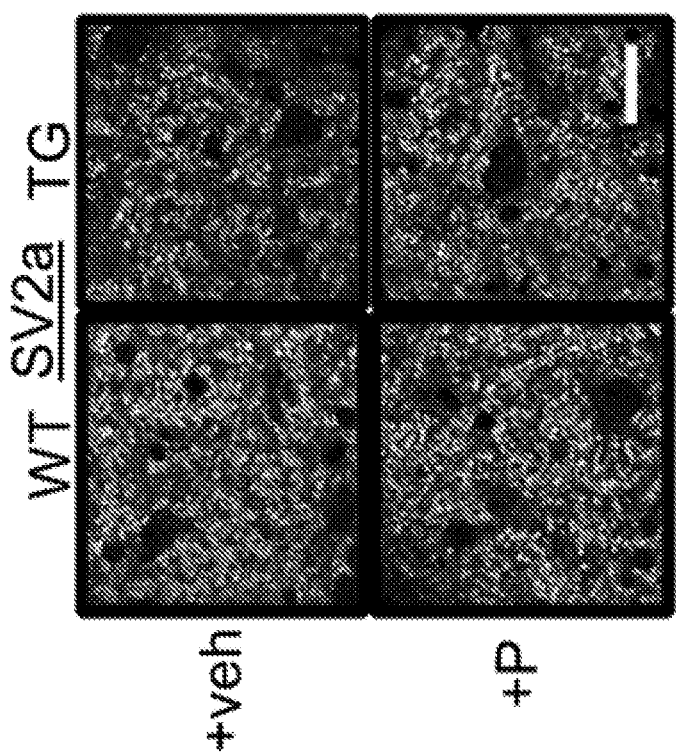
FIG. 36 is an image showing APP/PS1 transgenic and wild-type mice that were orally gavaged with vehicle (n=13 transgenic, 15 WT) or 3 mpk PSCMA BID (n=14 transgenic, 14 WT) for a total of 30 days prior to behavioral analysis. After behavioral testing on day 42, PFA-perfused brains were sectioned and immunostained for the presynaptic marker SV2A.
Figure 37:
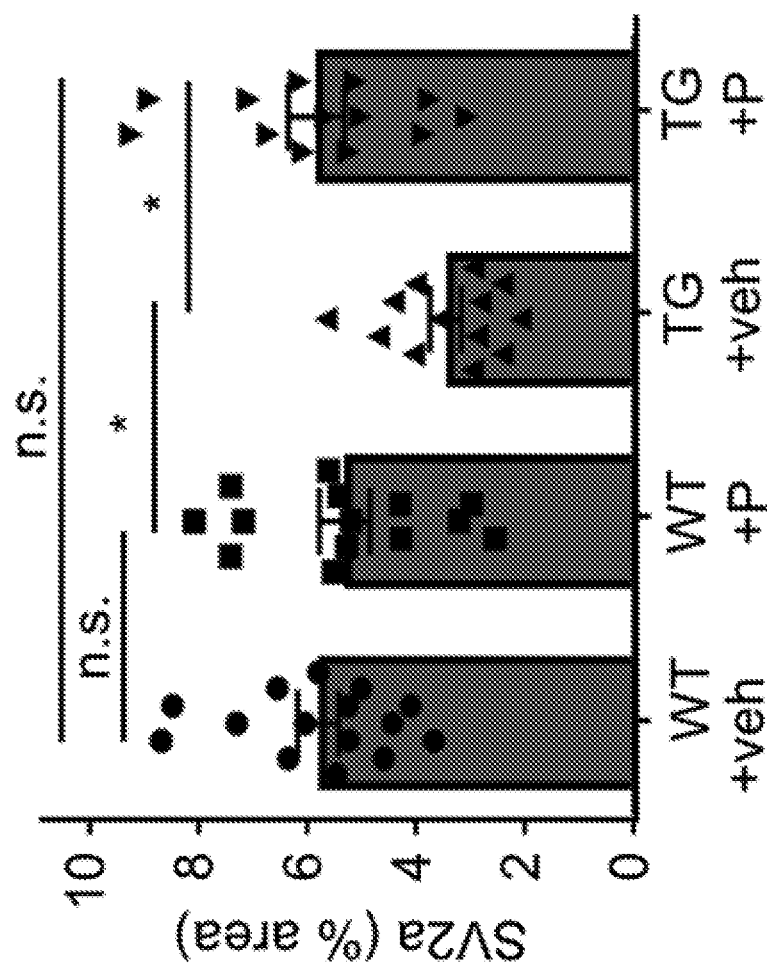
FIG. 37 is a bar graph showing synaptotoxicity-induced 42% reduction in SV2a immunoreactivity in the hippocampi of AD model mice was significantly improved by PSCMA treatment, which restored the hippocampal area occupied by SV2a, as determined by one-way ANOVA with Tukey's multiple comparisons test (*, P<0.05). Scale bar=10 µm.
Figure 38:
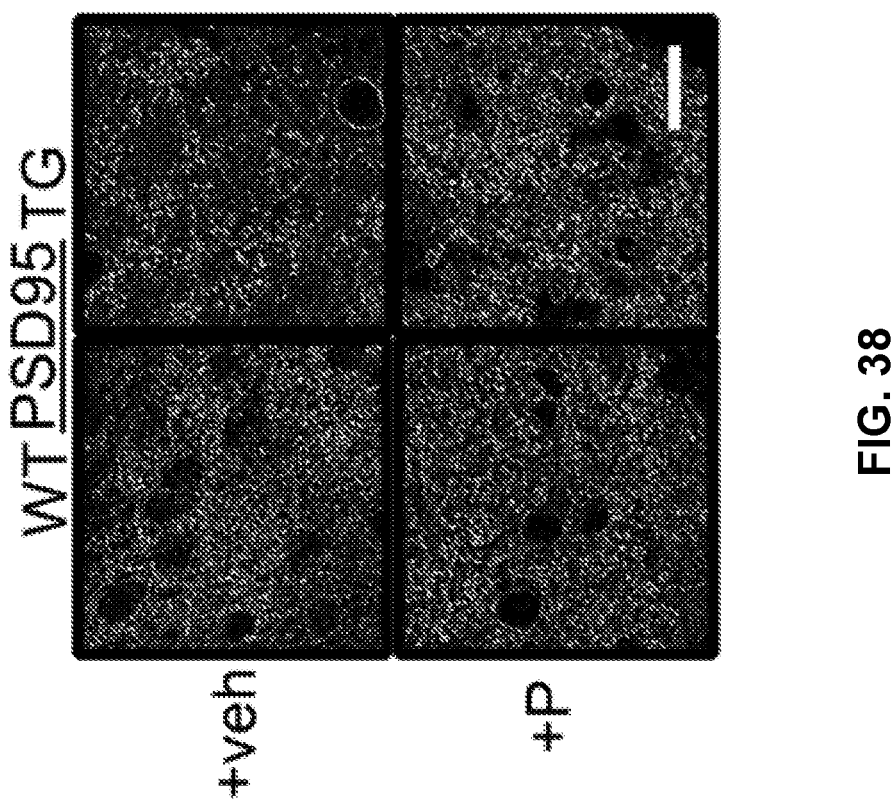
FIG. 38 is an image showing brains from the mice from FIG. 36 that were immunostained for the post-synaptic marker PSD95.
Figure 39:
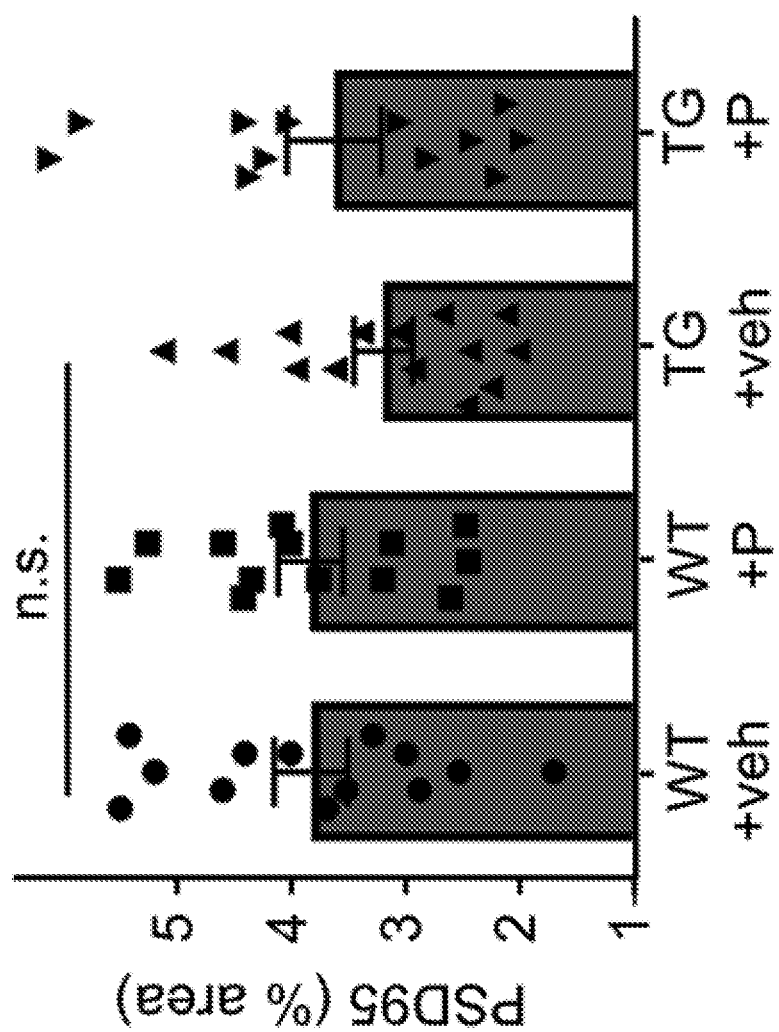
FIG. 39 is a bar graph showing a trend toward PSD95 area reduction in the hippocampus of vehicle-treated transgenic mice compared to WT, but it did not reach statistical significance, as determined by one-way ANOVA and Tukey's multiple comparisons test. Nevertheless, PSCMA reversed this trend. Scale bar=10 µm.

To determine whether behavioral recovery reflected repair of transgene-dependent synaptic damage, we examined hippocampal histological indicators of synaptic architecture. The presynaptic marker SV2a exhibited a 42% reduction in area occupied by immunoreactive puncta within the molecular layer of the dentate gyrus of APP/PS1 compared to WT mice (FIG. 36, 37). PSCMA treatment rescued APP/PS1 mice from synapse loss as indicated by the restoration of presynaptic SV2a immunoreactivity to wild type levels (FIG. 36, 37). Post-synaptic degeneration detected by PSD-95 staining showed a similar but non-significant statistical trend between transgenic and WT mice, with PSCMA countering the transgene-dependent deleterious trend (FIG. 38, 39).

Previous investigations of the role of the Aβo/$PrP^C$ axis in AD have shown restoration of learning and memory performance as well as synapse density by $PrP^C$ pathway blockade, while Aβ plaque load and neuroinflammatory hallmarks of astrogliosis and microgliosis persisted (Chung et al., 2010; Gimbel et al., 2010; Salazar et al., 2017; Um et al., 2013). Similar to these previous $PrP^C$-pathway-directed measures, the treatment with PSCMA did not alter Aβ plaque area in APP/PS1 mice (FIG. 42-47). In addition, there was no change in the elevated astrocytic GFAP and microglial Iba1 in APP/PS1 animals treated with PSCMA (FIG. 42-47). This is consistent with PSCMA selectively blocking $PrP^C$-mediated synaptic effects in APP/PS1 mice, without modulating Aβ metabolism or glial reaction to protein deposition.

REFERENCES

Aguzzi, A., and Altmeyer, M. (2016). Phase Separation: Linking Cellular Compartmentalization to Disease. Trends Cell Biol 26, 547-558.

Aimi, T., Suzuki, K., Hoshino, T., and Mizushima, T. (2015). Dextran sulfate sodium inhibits amyloid-beta oligomer binding to cellular prion protein. Journal of neurochemistry 134, 611-617.

Baertschi, S. W., Dorman, D. E., Occolowitz, J. L., Collins, M. W., Spangle, L. A., Stephenson, G. A., and Lorenz, L. J. (1997). Isolation and structure elucidation of the major degradation products of cefaclor formed under aqueous acidic conditions. J Pharm Sci 86, 526-539.

Banani, S. F., Lee, H. O., Hyman, A. A., and Rosen, M. K. (2017). Biomolecular condensates: organizers of cellular biochemistry. Nat Rev Mol Cell Biol 18, 285-298.

Brody, A. H., and Strittmatter, S. M. (2018). Synaptotoxic Signaling by Amyloid Beta Oligomers in Alzheimer's Disease Through Prion Protein and mGluR5. Adv Pharmacol 82, 293-323.

Caughey, B., and Raymond, G. J. (1993). Sulfated polyanion inhibition of scrapie-associated PrP accumulation in cultured cells. J Virol 67, 643-650.

Chung, E., Ji, Y., Sun, Y., Kascsak, R. J., Kascsak, R. B., Mehta, P. D., Strittmatter, S. M., and Wisniewski, T. (2010). Anti-PrP$^C$ monoclonal antibody infusion as a novel treatment for cognitive deficits in an Alzheimer's disease model mouse. BMC Neurosci 11, 130.

Citron, M., Westaway, D., Xia, W., Carlson, G., Diehl, T., Levesque, G., Johnson-wood, K., Lee, M., Seubert, P., Davis, A., et al. (1997). Mutant presenilins of Alzheimer's disease increase production of 42-residue amyloid β-protein in both transfected cells and transgenic mice. Nature medicine 3, 67-72.

Cleary, J. P., Walsh, D. M., Hofmeister, J. J., Shankar, G. M., Kuskowski, M. A., Selkoe, D. J., and Ashe, K. H. (2005). Natural oligomers of the amyloid-beta protein specifically disrupt cognitive function. Nat Neurosci 8, 79-84.

Colby, D. W., and Prusiner, S. B. (2011). Prions. Cold Spring Harb Perspect Biol 3, a006833.

Drummond, E., and Wisniewski, T. (2017). Alzheimer's disease: experimental models and reality. Acta Neuropathol 133, 155-175.

Ercanli, T., and Boyd, D. B. (2006). Exploration of the conformational space of a polymeric material that inhibits human immunodeficiency virus. J Chem Inf Model 46, 1321-1333.

Freir, D. B., Nicoll, A. J., Klyubin, I., Panico, S., Mc Donald, J. M., Risse, E., Asante, E. A., Farrow, M. A., Sessions, R. B., Saibil, H. R., et al. (2011). Interaction between prion protein and toxic amyloid beta assemblies can be therapeutically targeted at multiple sites. Nature communications 2, 336.

Garcia-Alloza, M., Robbins, E. M., Zhang-Nunes, S. X., Purcell, S. M., Betensky, R. A., Raju, S., Prada, C., Greenberg, S. M., Bacskai, B. J., and Frosch, M. P. (2006). Characterization of amyloid deposition in the APPswe/PS1dE9 mouse model of Alzheimer disease. Neurobiol Dis 24, 516-524.

Gimbel, D. A., Nygaard, H. B., Coffey, E. E., Gunther, E. C., Lauren, J., Gimbel, Z. A., and Strittmatter, S. M. (2010). Memory impairment in transgenic Alzheimer mice requires cellular prion protein. J Neurosci 30, 6367-6374.

Haas, L. T., Kostylev, M. A., and Strittmatter, S. M. (2014). Therapeutic molecules and endogenous ligands regulate the interaction between brain cellular prion protein (PrPC) and metabotropic glutamate receptor 5 (mGluR5). J Biol Chem 289, 28460-28477.

Haas, L. T., Salazar, S. V., Kostylev, M. A., Um, J. W., Kaufman, A. C., and Strittmatter, S. M. (2016). Metabotropic glutamate receptor 5 couples cellular prion protein to intracellular signalling in Alzheimer's disease. Brain 139, 526-546.

Haas, L. T., Salazar, S. V., Smith, L. M., Zhao, H. R., Cox, T. O., Herber, C. S., Degnan, A. P., Balakrishnan, A., Macor, J. E., Albright, C. F., et al. (2017). Silent Allosteric Modulation of mGluR5 Maintains Glutamate Signaling while Rescuing Alzheimer's Mouse Phenotypes. Cell Rep 20, 76-88.

Haas, L. T., and Strittmatter, S. M. (2016). Oligomers of Amyloid beta Prevent Physiological Activation of the Cellular Prion Protein-Metabotropic Glutamate Receptor 5 Complex by Glutamate in Alzheimer Disease. J Biol Chem 297, 17112-17121.

Hardy, J., and Selkoe, D. J. (2002). The amyloid hypothesis of Alzheimer's disease: progress and problems on the road to therapeutics. Science 297, 353-356.

Hobi, R., Hubscher, U., Neftel, K., Alteri, E., Poncioni, B., Walker, M. R., Woods-Cook, K., Schneider, P., and Lazdins, J. K. (2001). Anti-HIV-1 activity in vitro of ceftazidime degradation products. Antivir Chem Chemother 12, 109-118.

Hyman, A. A., Weber, C. A., and Julicher, F. (2014). Liquid-liquid phase separation in biology. Annu Rev Cell Dev Biol 30, 39-58.

Jankowsky, J. L., Fadale, D. J., Anderson, J., Xu, G. M., Gonzales, V., Jenkins, N. A., Copeland, N. G., Lee, M. K., Younkin, L. H., Wagner, S. L., et al. (2004). Mutant presenilins specifically elevate the levels of the 42 residue beta-amyloid peptide in vivo: evidence for augmentation of a 42-specific gamma secretase. Human molecular genetics 13, 159-170.

Kaufman, A. C., Salazar, S. V., Haas, L. T., Yang, J., Kostylev, M. A., Jeng, A. T., Robinson, S. A., Gunther, E. C., van Dyck, C. H., Nygaard, H. B., et al. (2015). Fyn inhibition rescues established memory and synapse loss in Alzheimer mice. Ann Neurol 77, 953-971.

Klyubin, I., Nicoll, A. J., Khalili-Shirazi, A., Farmer, M., Canning, S., Mably, A., Linehan, J., Brown, A., Wakeling, M., Brandner, S., et al. (2014). Peripheral administration of a humanized anti-PrP antibody blocks Alzheimer's disease Abeta synaptotoxicity. J Neurosci 34, 6140-6145.

Kostylev, M. A., Kaufman, A. C., Nygaard, H. B., Patel, P., Haas, L. T., Gunther, E. C., Vortmeyer, A., and Strittmatter, S. M. (2015). Prion-Protein-interacting Amyloid-beta Oligomers of High Molecular Weight Are Tightly Correlated with Memory Impairment in Multiple Alzheimer Mouse Models. J Biol Chem 290, 17415-17438.

Lauren, J., Gimbel, D. A., Nygaard, H. B., Gilbert, J. W., and Strittmatter, S. M. (2009). Cellular prion protein mediates impairment of synaptic plasticity by amyloid-beta oligomers. Nature 457, 1128-1132.

Lu, D., Giles, K., Li, Z., Rao, S., Dolghih, E., Gever, J. R., Geva, M., Elepano, M. L., Oehler, A., Bryant, C., et al. (2013). Biaryl amides and hydrazones as therapeutics for prion disease in transgenic mice. J Pharmacol Exp Ther 347, 325-338.

Morris, R. (1984). Developments of a water-maze procedure for studying spatial learning in the rat. Journal of neuroscience methods 11, 47-60.

Purro, S. A., Nicoll, A. J., and Collinge, J. (2018). Prion Protein as a Toxic Acceptor of Amyloid-beta Oligomers. Biol Psychiatry 83, 358-368.

Salazar, S. V., Gallardo, C., Kaufman, A. C., Herber, C. S., Haas, L. T., Robinson, S., Manson, J. C., Lee, M. K., and Strittmatter, S. M. (2017). Conditional Deletion of Prnp Rescues Behavioral and Synaptic Deficits after Disease Onset in Transgenic Alzheimer's Disease. J Neurosci 37, 9207-9221.

Schneider, L. S., Mangialasche, F., Andreasen, N., Feldman, H., Giacobini, E., Jones, R., Mantua, V., Mecocci, P., Pani, L., Winblad, B., et al. (2014). Clinical trials and late-stage drug development for Alzheimer's disease: an appraisal from 1984 to 2014. J Intern Med 275, 251-283.

Smith, L. M., and Strittmatter, S. M. (2017). Binding Sites for Amyloid-beta Oligomers and Synaptic Toxicity. Cold Spring Harb Perspect Med 7.

Smith, L. M., Zhu, R., and Strittmatter, S. M. (2018). Disease-modifying benefit of Fyn blockade persists after washout in mouse Alzheimer's model. Neuropharmacology 130, 54-61.

Sonati, T., Reimann, R. R., Falsig, J., Baral, P. K., O'Connor, T., Hornemann, S., Yaganoglu, S., Li, B., Herrmann, U.S., Wieland, B., et al. (2013). The toxicity of antiprion antibodies is mediated by the flexible tail of the prion protein. Nature 501, 102-106.

Um, J. W., Kaufman, A. C., Kostylev, M., Heiss, J. K., Stagi, M., Takahashi, H., Kerrisk, M. E., Vortmeyer, A., Wisniewski, T., Koleske, A. J., et al. (2013). Metabotropic glutamate receptor 5 is a coreceptor for Alzheimer abeta oligomer bound to cellular prion protein. Neuron 79, 887-902.

Um, J. W., Nygaard, H. B., Heiss, J. K., Kostylev, M. A., Stagi, M., Vortmeyer, A., Wisniewski, T., Gunther, E. C., and Strittmatter, S. M. (2012). Alzheimer amyloid-beta oligomer bound to postsynaptic prion protein activates Fyn to impair neurons. Nat Neurosci 15, 1227-1235.

Zhang, X., Lin, Y., Eschmann, N. A., Zhou, H., Rauch, J. N., Hernandez, I., Guzman, E., Kosik, K. S., and Han, S. (2017). RNA stores tau reversibly in complex coacervates. PLOS Biol 15, e2002183.

The entire disclosure of each of the patent documents and scientific articles referred to herein is incorporated by reference for all purposes.

The disclosure may be embodied in other specific forms without departing from the spirit or essential characteristics thereof. The foregoing embodiments are therefore to be considered in all respects illustrative rather than limiting the disclosure described herein. Scope of the disclosure is thus indicated by the appended claims rather than by the foregoing description, and all changes that come within the meaning and range of equivalency of the claims are intended to be embraced therein.

We claim:

1. A method of treating an amyloid-related disorder in a subject in need thereof, the method comprising administering to the subject a therapeutically effective amount of an anionic polymer, or a pharmaceutically acceptable salt thereof, wherein the anionic polymer comprises poly (4-styrenesulfonic acid-co-maleic acid), or the sodium salt thereof.

2. The method of claim 1, wherein the anionic polymer comprises about 100 to about 20,000 constitutional repeating units.

3. The method of claim 2, wherein the anionic polymer comprises about 100 to about 10,000 constitutional repeating units.

4. The method of claim 1, wherein the amyloid-related disorder is Alzheimer's disease, senile systemic amyloidosis, cerebral amyloid angiopathy, Parkinson's disease, rheumatoid arthritis, Huntington's disease, medullary thyroid cancer, cardiac arrhythmia (dysrhythmia), atherosclerosis, polactinoma, familial amyloid polyneuropathy, heredity non-neuropathic systemic amyloidosis (Ostertag type), Beta 2 microglobulin amyloidosis, Finnish type amyloidosis, lattice dystrophy, cerebral amyloid angiopathy (congophilic angiopathy), systemic AL amyloidosis, sporadic inclusion body myositis, phaeochromocytoma, osteomyelitis, multiple myeloma, type II diabetes, scrapie, bovine spongiform encephalitis, Creutzfeldt Jakob disease, Gerstmann Straussler Scheinker syndrome, fatal familial insomnia, kuru, a prion protein related disorder, memory impairment, localized amyloidosis, or systemic amyloidosis.

5. The method of claim 4, wherein the amyloid-related disorder is Alzheimer's disease.

6. The method of claim 1, further comprising administering to the subject a therapeutically effective amount of a second therapeutic agent to the subject selected from the group consisting of a cholinesterase inhibitor, an antioxidant Ginkobiloba extract, a nonsteroidal anti-inflammatory agent, a non-specific NMDA antagonist, carbidopa/levodopa, a dopamine agonist, a COMT inhibitor, an anticholinergic, a MAO inhibitor, a biguanide, a glucosidase inhibitor, insulin, a meglitinide, a sulfonylurea, a biguanide/glyburide combination, a thiozolidinedione, a PPAR-alpha agonist, a PPAR-gamma agonist, a PPAR alpha/gamma dual agonist, a SGLT2 inhibitor, an inhibitor of fatty acid binding protein (aP2), a glucagon-like peptide-1 (GLP-1), and a dipeptidyl peptidase IV (DP4) inhibitor.

7. The method of claim 1, wherein the subject is a human.

8. The method of claim 1, wherein the anionic polymer, or a pharmaceutically acceptable salt thereof, is administered to the subject as a pharmaceutical composition comprising one or more pharmaceutically acceptable carriers.

9. The method of claim 8, wherein the pharmaceutical composition comprises about 0.1% to about 1% w/v hydroxypropyl methylcellulose and about 0.05% to about 0.5% w/v polysorbate 80.

10. The method of claim 9, wherein the pharmaceutical composition comprises about 0.5% w/v hydroxypropyl methylcellulose and about 0.1% w/v polysorbate 80.

11. The method of claim 1, wherein the anionic polymer, or a pharmaceutically acceptable salt thereof, has a molecular weight of 3000 Da±2000 Da.

12. The method of claim 1, wherein the anionic polymer, or a pharmaceutically acceptable salt thereof, has a molecular weight of 4000 Da±3000 Da.

13. The method of claim 1, wherein the anionic polymer, or a pharmaceutically acceptable salt thereof, has a molecular weight of 5000 Da±3000 Da.

14. The method of claim 1, wherein the anionic polymer, or a pharmaceutically acceptable salt thereof, has a molecular weight of 6000 Da±4000 Da.

15. The method of claim 1, wherein the anionic polymer, or a pharmaceutically acceptable salt thereof, has a molecular weight of 8000 Da±5000 Da.

16. The method of claim 1, wherein the anionic polymer, or a pharmaceutically acceptable salt thereof, has a molecular weight of 10000 Da±6000 Da.

17. The method of claim 1, wherein the anionic polymer, or a pharmaceutically acceptable salt thereof, has a molecular weight of 15000 Da±10000 Da.

18. The method of claim 1, wherein the anionic polymer, or a pharmaceutically acceptable salt thereof, has a molecular weight of 20000 Da±15000 Da.

19. The method of claim 1, wherein the anionic polymer, or a pharmaceutically acceptable salt thereof, has a molecular weight of 30000 Da±20000 Da.

* * * * *